US007544519B2

(12) United States Patent  (10) Patent No.: US 7,544,519 B2
Hsu et al.  (45) Date of Patent: Jun. 9, 2009

(54) FHM A NOVEL MEMBER OF THE TNF LIGAND SUPERGENE FAMILY: MATERIALS AND METHODS FOR INTERACTION MODULATORS

(75) Inventors: Hailing Hsu, Moorpark, CA (US); Scott Kenneth Wooden, Thousand Oaks, CA (US); William James Boyle, Moorpark, CA (US)

(73) Assignee: Amgen Inc., Thousand Oaks, CA (US)

( * ) Notice: Subject to any disclaimer, the term of this patent is extended or adjusted under 35 U.S.C. 154(b) by 638 days.

(21) Appl. No.: 10/890,368

(22) Filed: Jul. 13, 2004

(65) Prior Publication Data

US 2004/0248324 A1    Dec. 9, 2004

Related U.S. Application Data

(60) Continuation of application No. 10/286,696, filed on Nov. 1, 2002, now Pat. No. 6,852,839, which is a division of application No. 09/632,287, filed on Aug. 3, 2000, now Pat. No. 6,521,422.

(60) Provisional application No. 60/147,294, filed on Aug. 4, 1999.

(51) Int. Cl.
*G01N 33/543* (2006.01)
*G01N 33/53* (2006.01)
*G01N 33/00* (2006.01)
(52) U.S. Cl. .................. 436/518; 436/7.1; 436/7.93
(58) Field of Classification Search ............ None
See application file for complete search history.

(56) References Cited

U.S. PATENT DOCUMENTS

| | | | |
|---|---|---|---|
| 5,312,733 | A | 5/1994 | MacLeod |
| 5,489,743 | A | 2/1996 | Robinson et al. |
| 5,605,690 | A | 2/1997 | Jacobs et al. |
| 5,843,789 | A | 12/1998 | Nomura et al. |
| 5,863,769 | A | 1/1999 | Young |
| 5,885,800 | A | 3/1999 | Emery et al. |
| 6,271,366 | B1 | 8/2001 | Kimura et al. |
| 6,274,339 | B1 | 8/2001 | Moore et al. |
| 6,599,719 | B2 | 7/2003 | Yu et al. |
| 6,627,199 | B1 | 9/2003 | Saris |
| 6,764,679 | B2 | 7/2004 | Ashkenazi et al. |
| 6,824,767 | B2 * | 11/2004 | Yu et al. ............. 424/85.1 |
| 2002/0111325 | A1 | 8/2002 | Li et al. |
| 2002/0150534 | A1 | 10/2002 | Yu et al. |
| 2002/0150583 | A1 * | 10/2002 | Gentz et al. ........... 424/178.1 |
| 2003/0027284 | A1 | 2/2003 | Yu et al. |
| 2003/0082736 | A1 | 5/2003 | Smith |
| 2003/0096355 | A1 | 5/2003 | Zhang |
| 2003/0129189 | A1 | 7/2003 | Yu et al. |
| 2003/0198640 | A1 | 10/2003 | Yu et al. |
| 2004/0013664 | A1 | 1/2004 | Gentz et al. |

FOREIGN PATENT DOCUMENTS

| | | |
|---|---|---|
| DE | 19809978 | 9/1999 |
| EP | 0648783 | 4/1995 |
| EP | 0861850 | 9/1998 |
| WO | WO-93/19777 | 10/1993 |
| WO | WO-94/06476 | 3/1994 |
| WO | WO-96/14328 | 5/1996 |
| WO | WO-96/37609 | 11/1996 |
| WO | WO-98/30694 | 7/1998 |
| WO | WO-98/35986 | 8/1998 |
| WO | WO-98/43998 | 10/1998 |
| WO | WO-99/03992 | 1/1999 |
| WO | WO-99/04001 | 1/1999 |
| WO | WO-99/06426 | 2/1999 |
| WO | WO-99/07738 | 2/1999 |
| WO | WO-99/11791 | 3/1999 |
| WO | WO-99/14330 | 3/1999 |
| WO | WO-99/20758 | 4/1999 |
| WO | WO-99/23105 | 5/1999 |
| WO | WO-99/26977 | 6/1999 |
| WO | WO-99/31128 | 6/1999 |
| WO | WO-99/35268 | 7/1999 |
| WO | WO-99/50413 | 10/1999 |
| WO | WO-99/51744 | 10/1999 |
| WO | WO-00/08139 | 2/2000 |
| WO | WO-00/18800 | 4/2000 |

OTHER PUBLICATIONS

Pitti et al., Nature. Dec. 17, 1998;396:699-703.*
Harlow et al., Antibodies, A Laboratory Manual. 1988. Cold Spring Harbor Laboratory, p. 241.*
Zhang et al: "Modulation of T-cell responses to alloantigens by TR6/DcR3," J. Clin. Invest. 107:1459-1468 (2003).
Aderka "The Potential Biological and Clinical Significance of the Soluble Tumor Necrosis Factor Receptors" Cytokine & Growth Factor Reviews, 7(3):231-240 (1996).
Aggarwal et al. "Characterization of Receptors for Human Tumor Necrosis Factor and their Regulation By Gamma Interferon" Nature, 318:665-667(1985).
Ausubel et al. eds., Transfection of DNA Into Eukaryotic Cells in Current Protocols in Molecular Biology, Section 9.1.1 9.1.3, John Wiley & Sons, New York 1996.
Baker et al. "Transducers of Life and Death: TNF Receptor Superfamily and Associated Proteins" Oncogene, 12(1):1-9 (1996).
Bamias et al. "Expression, Localization, and Functional Activity of TL1A, a Novel Th1-Polarizing Cytokine in Inflammatory Bowel Disease" J. of Immunol., 171:4868-4874 (2003).
Beyaert et al. Tumor Necrosis Factor and Lymphokines in: Cytokines eds. Anthony Mire Sluis and Robin Thorpe, Academic Press San Diego CA, 1998.

(Continued)

*Primary Examiner*—Manjunath Rao
*Assistant Examiner*—Cherie Woodward
(74) *Attorney, Agent, or Firm*—Marshall Gerstein & Borun LLP

(57) ABSTRACT

The present invention provides a purified polynucleotide encoding a novel polypeptide, designated Fhm, which belongs to the TNF gene superfamily; to purified Fhm polypeptide molecules; to antibodies that bind Fhm; to materials comprising such molecules; and to methods of using such molecules.

25 Claims, 2 Drawing Sheets

OTHER PUBLICATIONS

Browning et al. "Lymphotoxin Beta, a Novel Member of the TNF Family That Forms a Heteromeric Complex with Lymphotoxin on the Cell Surface" Cell, 72:847 856 (1993).

Bucay et al. "Osteoprotegerin-Deficient Mice Develop Early Onset Osteoporosis and Arterial Calcification" Genes & Development, 12:1260-1268 (1998).

Chen et al. "Quantification and Detection of DcR3, a Decoy Receptor in TNFR Family" J. of Immunol. Meth., 285:63-70 (2004).

Chew et al. "A Novel Secreted Splice Variant of Vascular Endothelial Cell Growth Inhibitor" FASEB J., 16:742-744 (2002).

Connolly et al. "In Vivo Inhibition of Fas Ligand-Mediated Killing by TR6, a Fas Ligand Decoy Receptor" Journal of Pharmacology and Experimental Therapeutics, 298(1):25-33 (2001).

Degli-Esposti "To Die or Not to Die—The Quest of the TRAIL Receptors" Journal of Leukocyte Biology, 65:535-542 (1999).

Degli-Esposti et al. "Cloning and Characterization of TRAIL-R3, a Novel Member of the Emerging TRAIL Receptor Family" J. Exp. Med. 186(7):1165-1170 (1997).

Degli-Esposti et al. "The Novel Receptor TRAIL-R4 Induces NF-kb and Protects Against TRAIL-Mediated Apoptosis, yet Retains and Incomplete Death Domain" Immunity, 7: 813-820 (1997).

Emery et al. "Osteoprotegerin is a Receptor for the Cytotoxic Ligand TRAIL" J. of Biol. Chem., 273(23):14363-14367 (1998).

Fernandez-Botran "Soluble Cytokine Receptors: Their Role In Immunoregulation" FASB J., 5:2567-2574 (1991).

Fisher, Production of Antibody in Radioimmunoassay in ; Manual of Clinical Immunology, 2d Ed. (Rose and Friedman, eds.) Amer. Soc. For Microbiol., Washington, D.C., 1980.

Gill et al. "Differential Expression of Light and Its Receptors in Human Placental Villi and Amniochorion Membranes" American Journal of Pathology, 161(6):2011-2017 (2002).

Griffith et al. "Functional Analysis of TRAIL Receptors Using Monoclonal Antibodies" J. of Immunol., 162(5):2597-2605 (1999).

Griffith et al. "Monocyte-Mediated Tumoricidal Activity via the Tumor Necrosis Factor-related Cytokine, TRAIL" J. Exp. Med. 189(8):1343-1354 (1999).

Griffith et al. "TRAIL: a Molecule with Multiple Receptors and Control Mechanisms" Curr. Opin. Immnunol. 10(5):559-563 (1998).

Hofmann "The Modular Nature of Apoptotic Signaling Proteins" CMLS, 55:1113-1128 (1999).

Hsu et al. "Enhanced Adhesion of Monocytes Via Reverse Signaling Triggered by Decoy Receptor 3" Experimental Cell Research, 292:241-251 (2004).

Kim et al. "Selective Induction of Tumor Necrosis Receptor factor 6/Decoy Receptor 3 Release by Bacterial Antigens in Human Monocytes and Myeloid Dendritic Cells" Infection and Immunity, 72(1):89-93 (2004).

Marsters et al. "A Novel Receptor for Apo2L/TRAIL Contains a Truncated Death Domain" Current Biology, 7(12):1003-1006 (1997).

McFarlane et al. "Identification and Molecular Cloning of Two Novel Receptors for the Cytotoxic Ligand TRAIL" J. Biol. Chem., 272(41): 25417-25420 (1997).

Meurs et al. "Tumor Suppressor Function of the Interferon-Induced Double-Stranded RNA-Activated Protein Kinase" Proc. Natl. Acad. Sci. USA, 90:232-236 (1993).

Migone et al. "TL1A is a TNF-Like Ligand for DR3 and TR6/DcR3 and Functions as a T Cell Costimulator" Immunity, 16:479-492 (2002).

Moult "The Current State of the Art in Protein Structure Prediction" Curr. Op. in Biotech., 7(4):422 427 (1996).

Naismith et al. "Modularity in the TNF-Receptor Family" TIBS 23:74-79 (1998).

Nophar et al. "Soluble Forms of Tumor Necrosis Factor Receptors (TNF Rs). The cDNA for the Type I TNF-R, Cloned Using Amino Acid Sequence Data of its Soluble Form, Encodes Both the Cell Surface and a Soluble Form of the Receptor" EMBO J., 9(10):3269-3278 (1990).

Orlinick et al. "TNF Related Ligands and Their Receptors" Cell Signal, 10(8):543-551 (1998).

Ouchterlony et al., Immunodiffusion and Immunoelectrophoresis in: Handbook of Experimental Immunology ed. D. Weir, Blackwell, 1973.

Pan et al. "An Antagonist Decoy Receptor and a Death Domain-Containing Receptor for TRAIL" Science, 277:815-818 (1997).

Pan et al. "The Receptor for the Cytotoxic Ligand TRAIL" Science, 276:111-113 (1997).

Pan et al. "TRUNDD, a New Member of the TRAIL Receptor Family that Antagonizes TRAIL Signalling" FEBS Letters 424:41-45 (1998).

Perry et al. "Characterization of Proximal Colonic Lymphoid Tissue in the Mouse" The Anatomical Record, 220:305-312 (1988).

Pitti et al. "Genomic Amplification of a Decoy Receptor for Fas Ligand in Lung and Colon Cancer" Nature, 396:699-703 (1998).

Porteu et al. "Human Neutrophil Elastase Releases a Ligand binding Fragment for the 75 kDa Tumor Necrosis Factor (TNF) Receptor" J. Biol. Chem., 266:18846-18853 (1991).

Schneider et al. "Characterization of Two Receptors for TRAIL", FEBS Lett. 416:329-334 (1997).

Sheridan et al. "Control of TRAIL-Induced Apoptosis by a Family of Signaling and Decoy Receptors" Science, 277:818-821 (1997).

Shi et al. "Death Decoy Receptor TR6/DcR3 Inhibits T Cell Chemotaxis In Vitro and In Vivo" J. of Immunol., 171:3407-3414 (2003).

Shi et al. "Mouse T Cells Receive Costimulatory Signals from Light, a TNF Family Member" Blood, 100(9):3279-3286 (2002).

Simonet et al. "Osteoprotegerin: A Novel Secreted Protein Involved in the Regulation of Bone Density" Cell, 89:309-319 (1997).

Smith et al. "Four New Members Expand the Interleukin 1 Superfamily" J. Bio. Chem., 275(2):1169-1175 (2000).

Smith et al. "The TNF Receptor Superfamily of Cellular and Viral Proteins: Activation, Costimulation, and Death" Cell, 76(6):959-962 (1994).

Tan et al. "Characterization of a Novel TNF-Like Ligand and Recently Described TNF Ligand and TNF Receptor Superfamily Genes and Their Constitutive and Inducible Expression in Hematopoietic and Non-hematopoietic Cells" Gene, 204:35-46 (1997).

Vaitukaitis et al. "A Method For Producing Specific Antisera With Small Doses of Immunogen" J. Clin. Endocrinol. Metab., 33:988-991 (1971).

Walczak et al. "TRAIL-R2: a Novel Apoptosis-Mediating Receptor for TRAIL" The EMBO Journal, 16(17): 5386-5397 (1997).

Wallach et al. "Soluble and Cell Surface Receptors for Tumor Necrosis Factor" Agents Actions Suppl., 35:51-57 (1991).

Wan et al. "A TNF Family Member Light Tranduces Costimulatory Signals into Human T Cells" J. of Immunol., 169:6813-6821 (2002).

Wan et al. "DcR3/TR6 Modulates Immune Cell Interactions," Journal of Cellular Biochemistry, 89:603-612 (2003).

Wang et al. "Cloning, Expression and Biological Activity of VEGI(151), a Non-Vascular endothelial Cell Growth Inhibitor" ACTA Biochimica et Biophysica Sinica, 32(5):485-489 (2000).

Wen et al. "TL1A-induced NF-kB Activation and c-IAP2 Production Prevent DR3-mediated Apoptosis in TF-1 Cells" J. Biol. Chem., 278(40):39251-39258 (2003).

Wu et al. "Clinical Significance of Detecting Elevated Serum DcR3/TR6/M68 in Malignant Tumor Patients" Int. J. Cancer, 105:724-732 (2003).

Wu et al. "DcR3/TR6 Effectively Prevents Islet Primary Nonfunction After Transplantation" Diabetes, 52:2279-2286 (2003).

Wu et al. "Killer/DR5 is a DNA Damage-Inducible p53-Regulated Death Receptor Gene" Nature Genetics, 17:141-143 (1997).

Wu et al. "Molecular Cloning and Functional Analysis of the Mouse Homologue of the Killer/DR5 Tumor Necrosis Factor-related Apoptosis-inducing Ligand (TRAIL) Death Receptor" Cancer Research, 59:2770-2775 (1999).

Yang et al. "Soluble Decoy Receptor 3 Induces Angiogenesis by Neutralization of TL1A, a Cytokine Belonging to Tumor Necrosis Factor Superfamily and Exhibiting Angiostatic Action" Cancer Research, 64:1122-1129 (2004).

Yu et al. "A Newly Identified Member of Tumor Necrosis Factor Receptor Superfamily (TR6) Suppresses Light-Mediated Apoptosis" J. of Biol. Chem., 274(20):13733-13736 (1999).

Yu et al. "Modulation of Endothelial Cell Growth Arrest and Apoptosis by Vascular Endothelial Growth Inhibitor" American Heart Association Circulation Research, 89:1161-1167 (2001).

Zhai et al. "Inhibition of Angiogenesis and Breast Cancer Xenograft Tumor Growth by Vegi, a Novel Cytokine of the TNF Superfamily," Int. J. Cancer, 82:131-136 (1999).

Zhai et al. "VEGI, a Novel Cytokine of the Tumor Necrosis Factor Family, is an Angiogenesis Inhibitor that Suppresses the Growth of Colon Carcinomas In Vivo" FASEB J., 13:181-189 (1999).

Zhang et al. "Light Sensitizes IFNγ-mediated Apoptosis of MDA-MB-231 Breast Cancer Cells Leading to Down-Regulation of Anti-Apoptosis Bcl-2 Family Members," Cancer Letters 195:201-210 (2003).

* cited by examiner

| | B | B/B' Loop | C' | C | | |
|---|---|---|---|---|---|---|
| | | | L-W | | Consensus | |
| | ---+PAAHLT---P--- | | | | | |
| 139- | EKKELRKVAHLTGKSN--- | | ---SRS-MPLEWEDTYGI--- | | Human FasL | (SEQ ID NO: 5) |
| 137- | EKKEPRSVAHLTGNPH--- | | ---SRS-IPLEWEDTYGT--- | | Mouse FasL | (SEQ ID NO: 6) |
| 136- | ETKKPRSVAHLTGNPR--- | | ---SRS-IPLEWEDTYGT--- | | Rat FasL | (SEQ ID NO: 7) |
| 116- | GDQNPQIAAHVISEASS--- | | ---KTT-SVLQWAEKGYY--- | | Human CD40L | (SEQ ID NO: 8) |
| 115- | GDEDPQIAAHVVSEANS--- | | ---NAA-SVLQWAKKGYY--- | | Mouse CD40L | (SEQ ID NO: 9) |
| 157- | GKPEAQPFAHLTINAASIP--- | | ---SGSHKVTLSSWYHDRGW--- | | Mouse OPGL | (SEQ ID NO: 10) |
| 158- | SKLEAQPFAHLTINATDIP--- | | ---SGSHKVSLSSWYHDRGW--- | | Human OPGL | (SEQ ID NO: 11) |
| 116- | ERGPQRVAAHITGTRGRSNTLSSPNSKNEKALGRKINSWESSRSGH--- | | | | Human TRAIL | (SEQ ID NO: 12) |
| 120- | GGRPQKVAAHITGITRRSNSALIPISKDGKTLGQKIESWESSRKGH--- | | | | Mouse TRAIL | (SEQ ID NO: 13) |
| 92- | RAPFKKSWAYLQVAKH--- | | ---LNK-TKLSWNKDG--- | | Human CD30L | (SEQ ID NO: 14) |
| 97- | STPSKKSWAYLQVSKH--- | | ---LNN-TKLSWNEDG--- | | Mouse CD30L | (SEQ ID NO: 15) |
| 82- | DLSPGLPAAHLIGAP--- | | ---LKGQ-GLGWETTKEQ--- | | Human LyTβ | (SEQ ID NO: 16) |
| 148- | DLNPELPAAHLIGAW--- | | ---MSGQ-GLSWEASQEE--- | | Mouse LyTβ | (SEQ ID NO: 17) |
| 57- | AHSTLKPAAHLIGDP--- | | ---SKQNS-LLWRANTDR--- | | Human TNFβ | (SEQ ID NO: 18) |
| 54- | THGILKPAAHLVGYP--- | | ---SKQNS-LLWRASTDR--- | | Mouse TNFβ | (SEQ ID NO: 19) |
| 82- | RTPSDKPVAHVVANP--- | | ---QAEGQ-LQWLNRRAN--- | | Human TNFα | (SEQ ID NO: 20) |
| 85- | QNSSDKPVAHVVANH--- | | ---QVEEQ-LEWLSQRAN--- | | Mouse TNFα | (SEQ ID NO: 21) |
| 89- | RADGDKPRAHLTVVRQTP--- | | ---TQHFKNQFPALHWEHELGL--- | | Human Fhm | (SEQ ID NO: 4) |

Figure 1 (1/2)

| | D | D/E Loop | E | | |
|---|---|---|---|---|---|
| | A-LS-GV-L-N-----LVV----GLYFIYSQV-F+GQ-CP-------V-L | | | Consensus | |
| 169- | VLLS-GVKYKK--GGLVINETGLYFVYSKVYFRGQSCN-------NLPL | | | Human FasL | (SEQ ID NO: 5) |
| 167- | ALIS-GVKYKK--GGLVINETGLYFVYSKVYFRGQSCN-------NQPL | | | Mouse FasL | (SEQ ID NO: 6) |
| 166- | ALIS-GVKYKK--GGLVINEAGLYFVYSKVYFRGQSCN-------SQPL | | | Rat FasL | (SEQ ID NO: 7) |
| 147- | TMSNNLVTLENG-KQLTVKRQGLYYIYAQVTFCSNREA----SSQAPF | | | Human CD40L | (SEQ ID NO: 8) |
| 146- | TMKSNLVMLENG-KQLTVKREGLYYVYTQVTFCSNREP----SSQRPF | | | Mouse CD40L | (SEQ ID NO: 9) |
| 193- | AKISN-MTLSNG-K-LRVNQDGFYYLYANICFRHHETS----GSVPTD | | | Mouse OPGL | (SEQ ID NO: 10) |
| 194- | AKISN-MTFSNG-K-LIVNQDGFYYLYANICFRHHETS----GDLATE | | | Human OPGL | (SEQ ID NO: 11) |
| 162- | SFLSN-LHLRNG-E-LVIHEKGFYYIYSQTYFRFQEE------IKENT | | | Human TRAIL | (SEQ ID NO: 12) |
| 166- | SFLNH-VLFRNG-E-LVIEQEGLYYIYSQTYFRFQEAEDASKMVSKD- | | | Mouse TRAIL | (SEQ ID NO: 13) |
| 290- | -ILH-GVRYQD--GNLVIQFPGLYFIICQLQFLVQ-CP------NNSVDL | | | Human CD30L | (SEQ ID NO: 14) |
| 125- | -TIH-GLIYQD--GNLIVQFPGLYFIVCQLQFLVQ-CS------NHSVDL | | | Mouse CD30L | (SEQ ID NO: 15) |
| 111- | AFLTSGTQFSDA-EGLALPQDGLYLYLCLVGYRGRAPPGGGDPQGRSV | | | Human LyTβ | (SEQ ID NO: 16) |
| 117- | AFLRSGAQFSPT-HGLALPQDGVYYLYCHVGYRGRTPPA-GRSRARSL | | | Mouse LyTβ | (SEQ ID NO: 17) |
| 86- | AFLQDGFSLSN--NSLLVPTSGIYFVYSQVVFSGKAYSPKATSSPLYL | | | Human TNFβ | (SEQ ID NO: 18) |
| 83- | AFLQDGFSLSN--NSLLIPTSGLYFVYSQVVFSGESCSPRAIPTPIYL | | | Mouse TNFβ | (SEQ ID NO: 19) |
| 111- | ALLANGVELRD--NQLVVPSEGLYLIYSQVLFKGQGCP---STHVLL | | | Human TNFα | (SEQ ID NO: 20) |
| 114- | ALLANGMDLKD--NQLVVPADGLYLIVSQVLFKGQGCP---DYVLL | | | Mouse TNFα | (SEQ ID NO: 21) |
| 126- | AFTKNRMNYTN--KFLLIPESGDYFIYSQVTFRGMTSECSEIRRAGRP | | | Human Fhm | (SEQ ID NO: 4) |

Figure 1 (2/2)

FHM A NOVEL MEMBER OF THE TNF LIGAND SUPERGENE FAMILY: MATERIALS AND METHODS FOR INTERACTION MODULATORS

RELATED APPLICATIONS

This application is a continuation of U.S. patent application Ser. No. 10/286,696, filed Nov. 1, 2002, now U.S. Pat. No. 6,852,839, which is a divisional of U.S. patent application Ser. No. 09/632,287, filed Aug. 3, 2000, now U.S. Pat. No. 6,521,422, which claims the benefit under 35 U.S.C. § 119(e) of U.S. Provisional Patent Application. No. 60/147,294, filed Aug. 4, 1999.

FIELD OF THE INVENTION

The present invention is in the field of recombinant genetics. In particular, the present invention relates to a novel receptor ligand, designated Fhm, belonging to the TNF ligand supergene family and nucleic acid molecules encoding the same. The invention also relates to vectors, host cells, anti-Fhm antibodies, and recombinant methods for producing Fhm polypeptides. The invention also relates to the use of the recombinant Fhm polypeptide to identify putative binding partners/receptors. In addition, provided for are methods and reagents for the diagnosis of diseases associated with abnormal Fhm or abnormal expression of its putative receptor, and methods and pharmaceutical compositions for the treatment of diseases associated with abnormal Fhm or abnormal expression of Fhm and/or its receptor. The invention also discloses pharmaceutical compositions for use in the treatment of these diseases.

BACKGROUND OF THE INVENTION

Technical advances in the identification, cloning, expression and manipulation of nucleic acid molecules have greatly accelerated the discovery of novel therapeutics based upon deciphering the human genome. Rapid nucleic acid sequencing techniques can now generate sequence information at unprecedented rates, and coupled with computational analyses, allow the assembly of overlapping sequences into entire genome and the identification of polypeptide-encoding regions. Comparison of a predicted amino acid sequence against a database compilation of known amino acid sequences can allow one to determine the extent of homology to previously identified sequence and/or structure landmarks. Cloning and expression of a polypeptide-encoding region of a nucleic acid molecule provides a polypeptide product for structural and functional analysis. Manipulation of nucleic acid molecules and encoded polypeptides to produce variants and derivatives thereof may confer advantageous properties on a product for use as a therapeutic.

However, in spite of the significant technical advances in genome research over the past decade, the potential for development of novel therapeutics based on the human genome is still largely unrealized. While a number of genes encoding potentially beneficial protein therapeutics, or those encoding polypeptides which may act as "targets" for therapeutic molecules, have been identified using recombinant DNA technology, the structure and function of a vast number of genes in the genome of mammals are yet unknown.

Identification and Characterization of TNF-Family of Ligands and Receptors

Tumor necrosis factor (TNF) was first identified in the serum of mice and rabbits which had been infected with *bacillus* of Calmette and Guerin(BCG) and which had been injected with endotoxin. TNF activity in the serum of these animals was recognized on the basis of its cytotoxic and anti-tumor activities. This TNF activity, referred to as TNF-α, is produced particularly by activated monocytes and macrophages, and has been implicated in normal growth processes as well as in a variety of diseases.

Following the discovery of TNF-α, independent research led to the identification of another cytokine associated with inflammatory responses lymphotoxin-α (LT-α), which was shown to be produced exclusively by lymphocytes. LT-α was subsequently shown to be 30% homologous with TNF-α, and was renamed TNF-β. It is now clear that TNF-α and TNF-β are members of a gene family that includes yet another member termed LT-β (Browning et al., *Cell* 72:847-856, 1993). The three genes are tightly linked within the MHC complex and show similar organization. Moreover, the biologically active forms of TNF-α and TNF-β are homotrimers and share many of the same biological activities including competing for the same cell-surface receptors (Agarwal et al., *Nature* 318:665-667, 1985). Two distinct but structurally homologous receptors have been identified, and each has been shown to bind both the ligands and mediate their effects.

However, it has been recognized that TNFs are only representative members of the rapidly expanding supergene family that includes TNF-α, TNF-β/lymphotoxin-α (LT-α), lymphotoxin-β (LT-β), FasL, CD40L, CD30L, CD27L, 4-1BBL, and TNF-related apoptosis-inducing ligand (TRAIL), RANKL, GITRL and TNF-2. See generally Orlinick et al., *Cell Signal*, 10(8):543-551 (1998). The distinctive but overlapping cellular responses induced by members of the TNF family of ligands following their interaction(s) with their cognate cell-surface receptors result in clearly defined developmental and regulatory changes in cells of the lymphoid, hematopoietic, and other lineages. For example, the TNF family of ligands are involved in growth regulation and differentiation of cells which are involved in inflammation, immune processes and hematopoiesis (Bayert, R. and Fiers, W., *Tumor Necrosis Factor and Lymphokines* in: Cytokines eds. Anthony Mire-Sluis and Robin Thorpe, Academic Press San Diego Calif., 1998). The TNF family of ligands activates the immune defenses against parasites, and act directly or indirectly as mediators in immune reactions and inflammatory processes. However, administration of TNF and/or other members of the TNF family can also be accompanied by harmful phenomena such as shock and tissue damage (Bayert, R. and Fiers, W., supra). The main physiological role of the TNF family of ligands is the activation of first-line reaction of an organism to microbial, parasitic, viral infections, or to mechanical stress and cancer. For example, TNF-related apoptosis-inducing ligand (TRAIL) has been demonstrated to induce apoptosis of a number of different types of cancer cells as well as virally infected cells.

Furthermore, a number of observations have also led to the conclusion that the TNF family of ligands are also involved in a variety of pathological conditions including cachexia, toxic shock syndrome, inflammatory diseases such as rheumatoid and osteoarthritis, and in lethality resulting from graft-versus-host reaction (GVHR) rapid necrosis of tumors, apoptosis, immunostimulation and resistance to parasites and viruses. (Bayert, R. and Fiers, W., supra).

Like other cytokines, the members of the TNF family of ligands act via specific cell-surface receptors. The receptors, with two exceptions, are type 1 membrane-associated proteins. Sequence homology amongst them is almost entirely confined to their extracellular domains. For example, two TNF receptors have been cloned which differ in size and in binding affinity (Bayert, R. and Fiers, W., supra). Both receptors bind TNF-α and TNF-β and are membrane associated proteins. The two receptors consist of extracellular domains which bind TNF (and are homologous for 28%), single transmembrane domains, and intracellular domains which are totally different from each other and which do not contain any recognizable structural motifs that have been associated with any particular function. Based on similarities in their extracellular domains, these receptors belong to a receptor gene superfamily that includes the low-affinity nerve growth factor (NGF) receptor, the Fas antigen, the human B-lymphocyte activation molecule CD40, CD27, 4-1BB, PV-T2, CD30, TNFR-RP, TRAIL-R, PV-A53R, RANK, GITR, and the OX40 antigen found on activated T-cells (Smith et al., *Cell,* 76(6):959-962, 1994; Baker and Reddy, *Oncogene,* 12(1):1-9, 1996).

In addition to the membrane associated receptor molecules described above, a number the receptors belonging to the TNF-receptor supergene family exist as soluble ligand binding proteins. Many of the soluble forms of the transmembrane receptors were subsequently identified as containing only the extracellular ligand binding domain(s) of the receptors. For example, a soluble form of TNF receptor has been found in urine and serum (See U.S. Pat. No. 5,843,789 and Nophar et al., *EMBO J.,* 9(10):3269-3278, 1990), and has been shown to arise by proteolytic cleavage of cell surface TNF-receptors (Wallach et al., *Agents Actions Suppl.,* 35:51-57 1991). These soluble forms of receptor molecules have been implicated in the modulation of TNF activity by not only interfering with TNF binding to its receptor, but also by stabilizing the TNF structure and preserving its activity, thus prolonging some of its effects (Aderka et al, *Cytokine & Growth Factor Reviews,* 7(3):231-240, 1996).

The activity of members of the TNF family of ligands is tightly regulated at the levels of secretion and receptor expression. Additional regulatory mechanisms are provided by action of specific inhibitory proteins present on cell surfaces and in biological fluids. While some of these inhibitory proteins have been identified as soluble forms of receptor molecules, the identity of many of these cytokine regulatory proteins are as yet unknown. However, abnormalities in the production of these substances might contribute to the pathophysiology of a variety of diseases including immune and neoplastic diseases. Besides their role in regulating cytokine activity in vivo, these regulatory molecules hold significant potential for therapeutic use as very specific inhibitors/anti-cytokine agents, and as indicators in diagnosis and assessment of immune function and growth parameters in a variety of autoimmune and malignant diseases.

Because of the important role of the TNF family of ligands (and their receptors) in health and disease, a need exists to identify, isolate, and characterize additional members of the family, for use in diagnosing and treating disease and pathological conditions.

SUMMARY OF THE INVENTION

The present invention relates to a novel serine/threonine kinase family and uses thereof. More specifically, the present invention relates to novel Fhm nucleic acid molecules and encoded polypeptides, and uses thereof.

The invention provides for an isolated nucleic acid molecule comprising a nucleotide sequence selected from the group consisting of:
(a) the nucleotide sequence set forth in SEQ ID NO: 3;
(b) a nucleotide sequence encoding the polypeptide set forth in SEQ ID NO: 4;
(c) a nucleotide sequence which hybridizes under moderately or highly stringent conditions to the complement of (a) or (b), wherein the encoded polypeptide has an activity of the polypeptide set forth in SEQ ID NO: 3; and
(d) a nucleotide sequence complementary to any of (a) through (c).

The invention also provides for an isolated nucleic acid molecule comprising a nucleotide sequence selected from the group consisting of:
(a) a nucleotide sequence encoding a polypeptide that is at least about 70, 75, 80, 85, 90, 95, 96, 97, 98, or 99 percent identical to the polypeptide set forth in 4, wherein the polypeptide has an activity of the encoded polypeptide set forth in SEQ ID NO: 4 as determined using a computer program selected from the group consisting of GAP, BLASTP, BLASTN, FASTA, BLASTA, BLASTX, BestFit, and the Smith-Waterman algorithm;
(b) a nucleotide sequence encoding an allelic variant or splice variant of the nucleotide sequence set forth in SEQ ID NO: 3, wherein the encoded polypeptide has an activity of the polypeptide set forth in SEQ ID NO: 4;
(c) a nucleotide sequence of SEQ ID NO: 3, (a), or (b) encoding a polypeptide fragment of at least about 25 amino acid residues, wherein the polypeptide has an activity of the polypeptide set forth in SEQ ID NO: 4;
(d) a nucleotide sequence encoding a polypeptide that has a substitution and/or deletion of 1 to 251 amino acid residues set forth in any of SEQ ID NOS: 3-4 wherein the encoded polypeptide has an activity of the polypeptide set forth in SEQ ID NO: 4;
(e) a nucleotide sequence of SEQ ID NO: 3, or (a)-(d) comprising a fragment of at least about 16 nucleotides;
(f) a nucleotide sequence which hybridizes under moderately or highly stringent conditions to the complement of any of (a)-(e), wherein the encoded polypeptide has an activity of the polypeptide set forth in SEQ ID NO:4; and
(g) a nucleotide sequence complementary to any of (a)-(e).

The invention further provides for an isolated nucleic acid molecule comprising a nucleotide sequence selected from the group consisting of:
(a) a nucleotide sequence encoding a polypeptide set forth in SEQ ID NO: 4 with at least one conservative amino acid substitution, wherein the encoded polypeptide has an activity of the polypeptide set forth in SEQ ID NO: 4;
(b) a nucleotide sequence encoding a polypeptide set forth in SEQ ID NO: 4 with at least one amino acid insertion, wherein the encoded polypeptide has an activity of the polypeptide set forth in SEQ ID NO: 4;
(c) a nucleotide sequence encoding a polypeptide set forth in SEQ ID NO: 4 with at least one amino acid deletion, wherein the encoded polypeptide has an activity of the polypeptide set forth in SEQ ID NO: 4;
(d) a nucleotide sequence encoding a polypeptide set forth in SEQ ID NO: 4 which has a C- and/or N-terminal truncation, wherein the encoded polypeptide has an activity of the polypeptide set forth in SEQ ID NO: 4;
(e) a nucleotide sequence encoding a polypeptide set forth in SEQ ID NO: 4 with at least one modification selected from the group consisting of amino acid substitutions, amino acid insertions, amino acid deletions, C-terminal truncation, and N-terminal truncation, wherein the polypeptide has an activity of the encoded polypeptide set forth in SEQ ID NO: 4;

(f) a nucleotide sequence of (a)-(e) comprising a fragment of at least about 16 nucleotides;

(g) a nucleotide sequence which hybridizes under moderately or highly stringent conditions to the complement of any of (a)-(f), wherein the encoded polypeptide has an activity of the polypeptide set forth in SEQ ID NO: 4; and (h) a nucleotide sequence complementary to any of (a)-(e).

The invention also provides for an isolated polypeptide comprising the amino acid sequence selected from the group consisting of:

(a) the mature amino acid sequence set forth in SEQ ID NO: 4 comprising a mature amino terminus at residue 1, and optionally further comprising an amino-terminal methionine;

(b) an amino acid sequence for an ortholog of SEQ ID NO: 4, wherein the polypeptide has an activity of the polypeptide set forth in SEQ ID NO: 4;

(c) an amino acid sequence that is at least about 70, 75, 80, 85, 90, 95, 96, 97, 98, or 99 percent identical to the amino acid sequence of SEQ ID NO: 4, wherein the polypeptide has an activity of the polypeptide set forth in SEQ ID NO: 4 as determined using a computer program selected from the group consisting of GAP, BLASTP, BLASTN, FASTA, BLASTA, BLASTX, BestFit, and the Smith-Waterman algorithm;

(d) a fragment of the amino acid sequence set forth in SEQ ID NO: 4 comprising at least about 25 amino acid residues, wherein the polypeptide has an activity of the polypeptide set forth in SEQ ID NO: 4;

(e) an amino acid sequence for an allelic variant or splice variant of either the amino acid sequence set forth in SEQ ID NO: 4, or at least one of (a)-(c) wherein the polypeptide has an activity of the polypeptide set forth in SEQ ID NO: 4.

The invention further provides for an isolated polypeptide comprising the amino acid sequence selected from the group consisting of:

(a) the amino acid sequence set forth in SEQ ID NO: 4 with at least one conservative amino acid substitution, wherein the polypeptide has an activity of the polypeptide set forth in SEQ ID NO: 4;

(b) the amino acid sequence set forth in SEQ ID NO: 4 with at least one amino acid insertion, wherein the polypeptide has an activity of the polypeptide set forth in SEQ ID NO: 4;

(c) the amino acid sequence set forth in SEQ ID NO: 4 with at least one amino acid deletion, wherein the polypeptide has an activity of the polypeptide set forth in SEQ ID NO: 4;

(d) the amino acid sequence set forth in SEQ ID NO: 4 which has a C- and/or N-terminal truncation, wherein the polypeptide has an activity of the polypeptide set forth in SEQ ID NO: 4; and (e) the amino acid sequence set forth in SEQ ID NO: 4, with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NO: 4.

Also provided are fusion polypeptides comprising the polypeptide sequences of (a)-(e) above of the preceding paragraphs.

The present invention also provides for an expression vector comprising the isolated nucleic acid molecules set forth herein, recombinant host cells comprising recombinant nucleic acid molecules set forth herein, and a method of producing a Fhm polypeptide comprising culturing the host cells and optionally isolating the polypeptide so produced.

A transgenic non-human animal comprising a nucleic acid molecule encoding a Fhm polypeptide is also encompassed by the invention. The Fhm nucleic acid molecules are introduced into the animal in a manner that allows expression and increased levels of the Fhm polypeptide, which may include increased circulating levels. The transgenic non-human animal is preferably a mammal.

Also provided are derivatives of the Fhm polypeptides of the present invention.

Additionally provided are selective binding agents such as antibodies and peptides capable of specifically binding the Fhm polypeptides of the invention. Such antibodies and peptides may be agonistic or antagonistic.

Pharmaceutical compositions comprising the nucleotides, polypeptides, or selective binding agents of the present invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents. The invention also provides for devices to administer a Fhm polypeptide encapsulated in a membrane.

The Fhm polypeptides and nucleic acid molecules of the present invention may be used to treat, prevent, ameliorate, diagnose and/or detect diseases and disorders, including those recited herein. Expression analysis in biological, cellular or tissue samples suggests that Fhm polypeptide may play a role in the diagnosis and/or treatment of TNF-related diseases including, but not limited to, acquired-immunodeficiency syndrome (AIDS), anemia, autoimmune diseases, cachexia, cancer, cerebral malaria, diabetes mellitus, disseminated intravascular coagulopathy, erythryoid sick syndrome, hemorrhagic shock, hepatitis, insulin resistance, leprosy, leukemia, lymphoma, meningitis, multiple sclerosis, myocardial ischaemia, obesity, rejection of transplanted organs, rheumatoid arthritis, septic shock syndrome, stroke, adult respiratory distress syndrome (ARDS), tuberculosis, and a number of viral diseases. This expression can de detected with a diagnostic agent such as Fhm nucleotide.

The invention encompasses diagnosing a pathological condition or a susceptibility to a pathological condition in a subject caused by or resulting from abnormal levels of Fhm polypeptide comprising determining the presence or amount of expression of the Fhm polypeptide in a sample; and comparing the level of said polypeptide in a biological, tissue or cellular sample from either normal subjects or the subject at an earlier time, wherein susceptibility to a pathological condition is based on the presence or amount of expression of the polypeptide.

The present invention also provides a method of assaying test molecules to identify a test molecule which binds to a Fhm polypeptide. The method comprises contacting a Fhm polypeptide with a test molecule and to determine the extent of binding of the test molecule to the polypeptide. The method further comprises determining whether such test molecules are agonists or antagonists of a Fhm polypeptide. The present invention further provides a method of testing the impact of molecules on the expression of Fhm polypeptide or on the activity of Fhm polypeptide.

Methods of regulating expression and modulating (i.e. increasing or decreasing) levels of a Fhm polypeptide are also encompassed by the invention. One method comprises administering to an animal a nucleic acid molecule encoding a Fhm polypeptide. In another method, a nucleic acid molecule comprising elements that regulate or modulate the expression of a Fhm polypeptide may be administered.

Examples of these methods include gene therapy, cell therapy, and anti-sense therapy as further described herein.

Surprisingly, a Fhm polypeptide was highly expressed in a wide range of primary human tumors. Therefore, the present polypeptide, and its useful nucleid acid intermediates, have demonstrated utility in differentiating transformed cells from the background.

In another aspect of the present invention, the Fhm polypeptides may be used for identifying receptors or binding partners thereof ("Fhm receptors" or "Fhm binding partners"). Various forms of "expression cloning" have been extensively used to clone receptors for protein or co-factors. See, for example, Simonsen and Lodish, *Trends in Pharmacological Sciences*, 15: 437-441, 1994, and Tartaglia et al., *Cell*, 83:1263-1271, 1995. The isolation of the Fhm receptor(s) or Fhm binding partner(s) is useful for identifying or developing novel agonists and antagonists of the Fhm polypeptide-signaling pathway.

Such agonists and antagonists include soluble Fhm ligand(s), anti-Fhm selective binding agents (such as Fhm antibodies and derivatives thereof), small molecules, peptides or derivatives thereof capable of binding Fhm polypeptides, or antisense oligonucleotides, any of which can be used for potentially treating one or more diseases or disorders, including those recited herein.

In certain embodiments, a Fhm polypeptide agonist or antagonist may be a protein, peptide, carbohydrate, lipid, or small molecular weight molecule which interacts with Fhm polypeptide to regulate its activity.

In another aspect of the present invention, the Fhm polypeptides may be used for identifying receptors thereof ("Fhm receptors"). Various forms of "expression cloning" have been extensively used for cloning to clone receptors for protein ligands. See for example, H. Simonsen and H. F. Lodish, *Trends in Pharmacological Sciences*, vol. 15, 437-44115:437-44, 1994, and Tartaglia et al., *Cell*, 83:1263-1271, 1995. The isolation of the Fhm receptor(s) is useful for identifying or developing novel agonists and antagonists of the Fhm polypeptide-signaling pathway. Such agonists and antagonists include soluble Fhm receptor(s), anti-Fhm receptor selective receptor-selective binding agents (such as antibodies and derivatives thereof), small molecules, and antisense oligonucleotides, any of which can be used for treating one or more of the diseases or disorders, including those recited herein.

DESCRIPTION OF THE FIGURE

FIG. 1 presents an alignment of the predicted amino acid sequence of Fhm polypeptide (SEQ ID NO: 4) is aligned with the corresponding regions of human FasL, mouse FasL, rat FasL, human CD40L, mouse CD40L, mouse OPGL, human OPGL, human TRAIL, mouse TRAIL, human CD30L, human CD30L, human LyT-β, mouse LyT-β, human TNF-β, mouse TNF-β, human TNF-α and mouse TNF-α. (SEQ ID NOS: 5-21) using the Pileup program (Wisconsin GCG Program Package ver. 8.1).

DETAILED DESCRIPTION OF THE INVENTION

The section headings herein are for organizational purposes only and are not to be construed as limiting the subject matter described therein.

Definitions

The terms "Fhm gene", "Fhm nucleic acid molecule", or "Fhm polynucleotide" refer to a nucleic acid molecule comprising or consisting essentially of a nucleotide sequence as set forth in SEQ ID NO: 3, comprising or consisting essentially of a nucleotide sequence encoding the polypeptide as set forth in SEQ ID NO: 4, or nucleic acid molecules related thereto. "Related" nucleic acid molecules comprise or consist essentially of a nucleotide sequence that is about 70 percent identical to the nucleotide sequence as shown in SEQ ID NO: 3, or comprise or consist essentially of a nucleotide sequence encoding a polypeptide having an amino acid sequence that is about 70 percent identical to the amino acid sequence set forth in SEQ ID NO: 4. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 3, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NO: 4. Related nucleic acid molecules also include fragments of the above Fhm nucleic acid molecules which are at least about 10 contiguous nucleotides, or about 15, or about 20, or about 25, or about 50, or about 75, or about 100, or greater than about 100 contiguous nucleotides. Related nucleic acid molecules also include fragments of the above Fhm nucleic acid molecules which encode a polypeptide of at least about 25 amino acid residues, or about 50, or about 75, or about 100, or greater than about 100 amino acid residues. Related nucleic acid molecules also include a nucleotide sequence encoding a polypeptide comprising or consisting essentially of a substitution and/or a deletion of one to 251 amino acid residues compared to the polypeptide in SEQ ID NO: 4. Related Fhm ligand nucleic acid molecules include those molecules which comprise nucleotide sequences which hybridize under moderate or highly stringent conditions as defined herein with any of the above nucleic acid molecules. In preferred embodiments, the related nucleic acid molecules comprise sequences which hybridize under moderate or highly stringent conditions with the sequence as shown in SEQ ID NO:3, or with a molecule encoding a polypeptide, which polypeptide comprises the amino acid sequence as shown in SEQ ID NO:4, or with a nucleic acid fragment as defined above, or with a nucleic acid fragment encoding a polypeptide as defined above. It is also understood that related nucleic acid molecules include allelic or splice variants of any of the above nucleic acids, and include sequences which are complementary to any of the above nucleotide sequences.

The term "Fhm polypeptide allelic variant" refers to one of several possible naturally occurring alternate forms of a gene occupying a given locus on a chromosome of an organism or a population of organisms.

The term "Fhm polypeptide splice variant" refers to a nucleic acid molecule, usually RNA, which is generated by alternative processing of intron sequences in an RNA transcript of Fhm polypeptide amino acid sequence set forth in SEQ ID NO: 4.

The term "expression vector" refers to a vector which is suitable for use in a host cell and contains nucleic acid sequences which direct and/or control the expression of inserted heterologous nucleic acid sequences. Expression includes, but is not limited to, processes such as transcription, translation, and RNA splicing, if introns are present.

The term "Fhm polypeptide" refers to a polypeptide comprising the amino acid sequence of SEQ ID NO: 4, and related polypeptides. Related polypeptides includes: Fhm allelic variants, Fhm splice variants, Fhm fragments, Fhm derivatives, Fhm-substitution, -deletion, and/or insertion variants, Fhm fusion polypeptides, and Fhm orthologs. Fhm polypeptides may be mature polypeptides, as defined herein, and may or may not have an amino terminal methionine residue, depending on the method by which they are prepared.

The term Fhm polypeptide fragment refers to a peptide or polypeptide that comprises less than the full length amino acid sequence of a Fhm polypeptide as set forth in SEQ ID NO: 4. Such a fragment may arise, for example, from a truncation at the amino terminus (with or without a leader sequence), a truncation at the carboxy terminus, and/or an internal deletion of the amino acid sequence (wherein the resulting polypeptide is at lease 6 amino acids or more in length). Fhm fragments may result from alternative RNA splicing or from in vivo protease activity.

In preferred embodiments, truncations comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such Fhm polypeptide fragments may optionally comprise an amino terminal methionine residue. It will be appreciated that such fragments can be used, for example, to generate antibodies to Fhm polypeptides.

The term "Fhm polypeptide variants" refers to Fhm polypeptides comprising amino acid sequences which contain one or more amino acid sequence substitutions, deletions (such as internal deletions and/or Fhm fragments), and/or additions (such as internal additions and/or Fhm fusion polypeptides) as compared to the Fhm polypeptide amino acid sequence set forth in SEQ ID NO: 4 (with or without leader sequences). Variants may be naturally occurring (e.g., Fhm polypeptide allelic variants, Fhm polypeptide orthologs or Fhm splice variants) or artificially constructed. Such Fhm-polypeptide variants may be prepared from the corresponding nucleic acid molecules encoding said variants, which have a DNA sequence that varies accordingly from the DNA sequences for wild type Fhm-receptor polypeptides as set forth in SEQ ID NO: 3.

The term "Fhm fusion polypeptide" "Fhm fusion polypeptide" refers to a fusion of one or more amino acids (such as a heterologous peptide or polypeptide) at the amino or carboxy terminus of the polypeptide as set forth in SEQ ID NO: 4, Fhm polypeptide allelic variants, Fhm polypeptide orthologs, Fhm polypeptide splice variants, or Fhm polypeptide variants having one or more amino acid deletions, substitutions or internal additions as compared to the Fhm polypeptide amino acid sequence set forth in SEQ ID NO: 4.

The term "Fhm polypeptide derivatives" refers to Fhm polypeptides, variants, or fragments thereof, that have been chemically modified, as for example, by covalent attachment of one or more water soluble polymers, N-linked or O-linked carbohydrates, sugars, phosphates, and/or other such molecules. Such modifications may be introduced into the molecule by reacting targeted amino acid residues of the purified or crude protein with an organic derivatizing agent that is capable of reacting with selected side chains or terminal residues. The resulting covalent derivatives are also useful in programs directed at identifying residues important for biological activity. The derivatives are modified in a manner that is different from naturally occurring Fhm polypeptide either in the type or location of the molecules attached to the polypeptide. Derivatives further include deletion of one or more chemical groups naturally attached to the Fhm polypeptide.

The terms "biologically active Fhm polypeptides", "biologically active Fhm polypeptide fragments", "biologically active Fhm polypeptide variants", and "biologically active Fhm polypeptide derivatives" refer to Fhm polypeptides having at least one activity characteristic of a Fhm polypeptide comprising the amino acid sequence of SEQ ID NO: 4, such as the ability to bind to one or more members of the TNF-receptor super gene (protein) family in biological assays. Immunogenic fragments of Fhm polypeptides are those capable of inducing in a host animal antibodies directed to the Fhm fragment.

The term "Fhm polypeptide ortholog" refers to a polypeptide from another species that corresponds to a Fhm polypeptide amino acid sequence set forth as SEQ ID NO: 4. For example, mouse and human Fhm polypeptides are considered orthologs of each other.

The term "mature Fhm polypeptide" refers to a Fhm polypeptide lacking a leader sequence. A mature Fhm polypeptide may also include other modifications of a polypeptide such as proteolytic processing of the amino terminus (with or without a leader sequence) and/or the carboxy terminus, cleavage of a smaller polypeptide from a larger precursor, N-linked and/or O-linked glycosylation, and the like.

The term "antigen" refers to a molecule or a portion of a molecule capable of being bound by a selective binding agent, such as an antibody, and additionally capable of being used in an animal to produce antibodies capable of binding to an epitope of that each antigen. An antigen may have one or more epitopes.

The term "mutein" refers to a mutant protein, polypeptide, variants, analogs or fragments of Fhm polypeptide. Muteins of Fhm may be prepared by deletion, insertion, substitution, point mutation, truncation, addition, transposition, PCR amplification, site-directed mutagenesis or other methods known in the art.

The terms "effective amount" and "therapeutically effective amount" refer to the amount of a Fhm polypeptide (or Fhm antagonist) necessary to support an observable change in the level of one or more biological activities of one or more members of the TNF-receptor gene family as set forth above, to bring about a meaningful patient benefit, i.e. treatment, healing, prevention, or amelioration of a condition. When applied to an individual active ingredient, administered alone, the term refers to that ingredient alone. When applied to a combination, the term refers to combined amounts of active ingredients that result in therapeutic effect, when administered in combination, serially or simultaneously. The Fhm polypeptides that have use in practicing the present invention may be naturally occurring full length polypeptides, or truncated polypeptides or variant homologs or analogs or derivatives or peptide fragments. Illustrative analogs include those in which one or more divergent amino acids between two species are substituted with the divergent amino acid from another species. Divergent amino acids may also be substituted with any other amino acid whether it be a conservative or a non-conservative amino acid.

The term "identity", as known in the art, refers to a relationship between the sequences of two or more polypeptide molecules or two or more nucleic acid molecules, as determined by comparing the sequences. In the art, "identity" also means the degree of sequence relatedness nucleic acid molecules or polypeptides sequences, as the case may be, as determined by the match between strings of two or more nucleotide or two or more amino acid sequences. "Identity" measures the percent of identical matches between the smaller of two or more sequences with gap alignments (if any) addressed by particular a mathematical model of computer program (i.e., "algorithms"). The term "similarity" is a related concept, but in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% (15/20). Therefore, in cases where there are conservative substitutions, the degree of percent similarity between two polypeptide sequences will be higher than the percent identity between those two sequences.

The term "isolated nucleic acid molecule" refers to a nucleic acid molecule of the invention that (1) has been separated from at least about 50 percent of proteins, lipids, carbohydrates or other materials with which it is naturally found when total DNA is isolated from the source cells, (2) is not linked to all or a portion of a polynucleotide to which the "isolated" isolated nucleic acid molecule "molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated from at least about 50 percent of polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The terms "nucleic acid sequence" or "nucleic acid molecule" refer to a DNA or RNA sequence. The term encompassesterms encompass molecules formed from any of the known base analogs of DNA and RNA such as, but not limited to 4-4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil.

5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" "non-naturally occurring" or "non-native" as used herein refers to a material that is not found in nature or that has been structurally modified or synthesized by man.

The term "operably linked" "operably linked" is used herein to refer to an arrangementa method of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably linked" "operably linked" to the coding sequence.

The term "pharmaceutically acceptable carrier" or "physiologically acceptable carrier" as used herein refers terms "pharmaceutically acceptable carrier" or "physiologically acceptable carrier" as used herein refer to one or more formulation materials suitable for accomplishing or enhancing the delivery of the Fhm polypeptide, Fhm nucleic acid molecule or Fhm selective binding agent as a pharmaceutical composition.

The term "selective binding agent" refers to a molecule or molecules having specificity for an Fhm polypeptide. As used herein, the terms, "specific" and "specificity" refer to the ability of the selective binding agents to bind to human Fhm polypeptides and not to bind to human non-Fhm polypeptides. It will be appreciated, however, that the selective binding agents may also bind orthologs of the polypeptide as set forth in SEQ ID NO: 4, that is, interspecies versions thereof, such as mouse and rat polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., Virology, 52:456, 1973; Sambrook et al., Molecular Cloning, a Laboratory Manual, Cold Spring Harbor Laboratories, New York, 1989; Davis et al., Basic Methods in Molecular Biology, Elsevier, 1986; and Chu et al., Gene, 13:197, 1981. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, it may be maintained transiently as an episomal element without being replicated, or I may replicate independently as a plasmid. A cell is considered to have been stably transformed when the DNA is replicated with the division of the cell.

The term "vector" is used to refer to any molecule (e.g., nucleic acid, plasmid, or virus) used to transfer coding information to a host cell.

Relatedness of Nucleic Acid Molecules and/or Polypeptides

It is understood that related nucleic acid molecules include allelic or splice variants of the nucleic acid molecule of SEQ ID NO: 3, and include sequences which are complementary to any of the above nucleotide sequences. Related nucleic acid molecules also include a nucleotide sequence encoding a polypeptide comprising or consisting essentially of a substitution, modification, addition and/or a deletion of one or more amino acid residues compared to the polypeptide in SEQ ID NO: 4.

Fragments include molecules which encode a polypeptide of at least about 25 amino acid residues, or about 50, or about 75, or about 100, or greater than about 100, amino acid residues of the polypeptide of SEQ ID NO: 4.

In addition, related Fhm nucleic acid molecules include those molecules which comprise nucleotide sequences which hybridize under moderately or highly stringent conditions as defined herein with the fully complementary sequence of the nucleic acid molecule of SEQ ID NO: 3, or of a molecule encoding a polypeptide, which polypeptide comprises the amino acid sequence as shown in SEQ ID NO: 4, or of a nucleic acid fragment as defined herein, or of a nucleic acid fragment encoding a polypeptide as defined herein. Hybridization probes may be prepared using the Fhm sequences provided herein to screen cDNA, genomic or synthetic DNA libraries for related sequences. Regions of the DNA and/or amino acid sequence of Fhm polypeptide that exhibit significant identity to known sequences are readily determined using sequence alignment algorithms as described herein, and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual,* 2nd Ed., Cold Spring Harbor Laboratory, (Cold Spring Harbor, N.Y. 1989); and Anderson et al., *Nucleic Acid Hybridization: a Practical approach,* Ch. 4, IRL Press Limited (Oxford, England). Limited, Oxford, England More stringent conditions (such as higher temperature, lower ionic strength, higher formamide, or other denaturing agent) may also be used; however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate (NaDodSO4 or SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4,6,8-7.4; however, at typical ionic strength conditions, the rate of hybridization is nearly independent of pH. See Anderson et al., *Nucleic Acid Hybridization: a Practical Approach,* Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$Tm(° C.)=81.5+16.6(\log[Na+])+0.41(\% G+C)-600/N-0.72(\% \text{ formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately" stringent conditions" " refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$T_m=2° C. \text{ per A-T base pair}+4° C. \text{ per G-C base pair}$$

*The sodium ion concentration in 6× salt sodium citrate (SSC) is 1 M. See Suggs et al., *Developmental Biology Using Purified Genes,* p. 683, Brown and Fox (eds.) (1981). High stringency washing conditions for oligonucleotides are usually at a temperature of 0-5° C. below the Tm of the oligonucleotide in 6×SSC, 0.1% SDS.

In another embodiment, related nucleic acid molecules comprise or consist of a nucleotide sequence that is about 70 percent (70%) identical to the nucleotide sequence as shown in SEQ ID NO: 3, or comprise or consist essentially of a nucleotide sequence encoding a polypeptide that is about 70 percent (70%) identical to the polypeptide as set forth in SEQ ID NO: 4. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 3, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NO:4.

Differences in the nucleic acid sequence may result in conservative and/or non-conservative modifications of the amino acid sequence relative to the amino acid sequence of SEQ ID NO: 4.

Conservative modifications to the amino acid sequence of SEQ ID NO: 4 (and corresponding modifications to the encoding nucleotides) will produce Fhm polypeptides having functional and chemical characteristics similar to those of a naturally occurring Fhm polypeptide. In contrast, substantial modifications in the functional and/or chemical characteristics of Fhm polypeptides may be accomplished by selecting substitutions in the amino acid sequence of SEQ ID NO: 4 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: trp, Tyr, Phe.

Non-conservative substitutions may involve the exchange of a member of one of these classes for a member from another class. Such substituted residues may be introduced into regions of the human Fhm polypeptide that are homologous with non-human Fhm polypeptide orthologs, or into the non-homologous regions of the molecule.

In making such changes, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.*, 157:105-131, 1982. It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5);(−2.5) and tryptophan (−3.4). In making changes based upon similar hydrophilicity values, the substitution of amino acids whose hydrophilicity values are within ±2 is preferred, those which are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the Fhm polypeptide, or to increase or decrease the affinity of the Fhm polypeptides described herein.

Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in SEQ ID NO: 4 using well known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an Fhm polypeptide to such similar polypeptides: With such a comparison, one can identify residues and portions of the molecules that are conserved among similar polypeptides. It will be appreciated that changes in areas of an Fhm polypeptide that are not conserved relative to such similar polypeptides would be less likely to adversely affect the biological activity and/or structure of the Fhm polypeptide.

One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in an Fhm polypeptide that correspond to amino acid residues that which are important for activity or structure in similar polypeptides. One skilled in the art may opt for chemically similar amino acid substitutions for such predicted important amino acid residues of Fhm polypeptides.

One skilled in the art can also analyze the three-dimensional structure and amino acid sequence in relation to that structure in similar polypeptides. In view of such information, one skilled in the art may predict the alignment of amino acid residues of an Fhm polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays know to those skilled in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. (See Moult J., *Curr. Op. in Biotech.,* 7(4):422-427, 1996. Chou et al., *Biochemistry,* 13(2):222-245, 1974; Chou et al., *Biochemistry,* 113(2):211-222, 1974; Chou et al., *Adv. Enzymol. Relat. Areas Mol. Biol.,* 47:45-148, 1978; Chou et al., *Ann. Rev. Biochem.,* 47:251-276 and Chou et al., *Biophys. J,* 26:367-384, 1979). Moreover, computer programs are currently available to assist with predicting secondary structure. One method of predicting secondary structure is based upon homology modeling. For example, two polypeptides or proteins which have a sequence identity of greater than 30%, or similarity greater than 40% often have similar structural topologies. The recent growth of the protein structural data base (PDB) has provided enhanced predictability of secondary structure, including the potential number of folds within a polypeptide's or protein's structure. See Holm et al., *Nucl. Acid. Res.,* 27(1):244-247, 1999. It has been suggested (Brenner et al., *Curr. Op. Struct. Biol.,* 7(3): 369-376, 1997) that there are a limited number of folds in a given polypeptide or protein and that once a critical number of structures have been resolved, structural prediction will become dramatically in more accurate.

Additional methods of predicting secondary structure include "threading" (Jones, D., *Curr. Opin. Struct. Biol.,* 7(3): 377-87, 1997; Sippl et al., *Structure,* 4(1):15-9, 1996), "profile analysis" (Bowie et al., *Science,* 253:164-170, 1991); Gribskov et al., *Meth. Enzym.,* 183:146-159, 1990; Gribskov et al., *Proc. Nat. Acad. Sci.,* 84(13):4355-4358 1987), and "evolutionary linkage" (See Home, supra, and Brenner, supra).

Preferred Fhm polypeptide variants include glycosylation variants wherein the number and/or type of glycosylation sites has been altered compared to the amino acid sequence set forth in SEQ ID NO: 4. In one embodiment, Fhm polypeptide variants comprise a greater or a lesser number of N-linked glycosylation sites than the amino acid sequence set forth in SEQ ID NO: 4. An N-linked glycosylation site is characterized by the sequence: Asn-X-Ser or Asn-X-Thr, wherein the amino acid residue designated as X may be any amino acid residue except proline. The substitution(s) of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

Additional preferred Fhm variants include cysteine variants, wherein one or more cysteine residues are deleted from or substituted for another amino acid (e.g., serine) as compared to the amino acid sequence set forth in SEQ ID NO: 4. Cysteine variants are useful when Fhm polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In addition, the polypeptide comprising the amino acid sequence of SEQ ID NO: 4 or an Fhm polypeptide variant may be fused to a homologous polypeptide to form a homodimer or to a heterologous polypeptide to form a heterodimer. Heterologous peptides and polypeptides include, but are not limited to: an epitope to allow for the detection and/or isolation of an Fhm fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in SEQ ID NO: 4 or an Fhm polypeptide variant.

Fusions can be made either at the amino terminus or at the carboxy terminus of the polypeptide comprising the amino acid sequence set forth in SEQ ID NO: 4 or an Fhm polypeptide variant. Fusions may be direct with no linker or adapter molecule, or indirect using a linker or adapter molecule. A linker or adapter molecule may be one or more amino acid residues, typically up to from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO: 4 or an Fhm polypeptide variant is fused to one or more domains of an Fc region of human IgG. Antibodies comprise two functionally independent parts, a variable domain known as "Fab", which binds antigens, and a constant domain known as "Fc", which is involved in effector functions such as complement activation and attack by phagocytic cells. An Fc has a long serum half-life, whereas an Fab is short-lived. (Capon et al., Nature, 337:525-31, 1989). When constructed together with a therapeutic protein, an Fc domain can provide longer half-life or incorporate such functions as Fc receptor binding, protein A binding, complement fixation and perhaps even placental transfer. Id. Table II summarizes the use of certain Fc fusions known in the art.

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcg2a | IL-10 | anti-inflammatory; transplant rejection | Zheng et al. (1995), J. Immunol., 154: 5590-5600 |
| IgG1 | TNF receptor | septic shock | Fisher et al. (1996), N. Engl. J. Med., 334: 1697-1702; Van Zee et al., (1996),J. Immunol., 156: 2221-2230 |
| IgG, IgA, IgM, or IgE (excluding the first domain) | TNF receptor | inflammation, autoimmune disorders | U.S. Pat. No. 5,808,029, issued Sep. 15, 1998 |
| IgG1 | CD4 receptor | AIDS | Capon et al. (1989), Nature 337: 525-531 |
| IgG1, IgG3 | N-terminus of IL-2 | anti-cancer, antiviral | Harvill et al. (1995), Immunotech., 1: 95-105 |
| IgG1 | C-terminus of OPG | osteoarthritis; bone density | WO 97/23614, published Jul. 3, 1997 |
| IgG1 | N-terminus of leptin | anti-obesity | PCT/US 97/23183, filed Dec. 11, 1997 |
| Human Ig Cgl | CTLA-4 | autoimmune disorders | Linsley (1991), J. Exp. Med., 174: 561-569 |

In one example, all or a portion of the human IgG hinge, CH2 and CH3 regions may be fused at either the N-terminus or C-terminus of the Fhm polypeptides using methods known to the skilled artisan. The resulting Fhm fusion polypeptide may be purified by use of a Protein A affinity column. Peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduce aggregation, etc.

Identity and similarity of related nucleic acid molecules and polypeptides can be readily calculated by known methods. Such methods include, but are not limited to, those described in *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of sequence Data*, Part 1, Griffin, A. M., and Griffin, H. G., eds., Humana Press, New Jersey, 1994; *Sequence Analysis in Molecular Biology*, von Heinje, G., Academic Press, 1987; *Sequence Analysis Primer*, Gribskov, M. and Devereux, J., eds., M. Stockton Press, New York, 1991; and Carillo et al., *SIAM J. Applied Math.* 48:1073, 1988.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., *Nucl. Acid. Res.*, 12:387, 1984; Genetics Computer Group, University of Wisconsin, Madison, Wis.), BLASTP, BLASTN, and FASTA (Altschul et al., *J. Mol. Biol.*, 215:403-410, 1990). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually $\frac{1}{10}$ times the gap opening penalty), as well as a comparison matrix such as PAM 250 or BLOSUM 62 are used in conjunction with the algorithm. A standard comparison matrix (see Dayhoff et al., *Atlas of Protein Sequence and Structure*, vol. 5, supp.35(3), 1978 for the PAM 250 comparison matrix; Henikoff et al., *Proc. Natl. Acad. Sci. USA*, 89:10915-10919, 1992 for the BLOSUM 62 comparison matrix) is also used by the algorithm.

Preferred parameters for polypeptide sequence comparison include the following:

| | |
|---|---|
| Algorithm: | Needleman and Wunsch, J. Mol. Biol. 48: 443-453 (1970), |
| Comparison matrix: | BLOSUM 62 from Henikoff and Henikoff, Proc. Natl. Acad. Sci. USA 89: 10915-10919 (1992). |
| Gap Penalty: | 12 |
| Gap Length Penalty: | 4 |
| Threshold of Similarity: | 0 |

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:

| | |
|---|---|
| Algorithm: | Needleman and Wunsch, J. Mol Biol. 48: 443-4, 1970 |
| Comparison matrix: | matches = +10, mismatch = 0 |
| Gap Penalty: | 50 |
| Gap Length Penalty: | 3 |

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between pairs of sequences (in which case GAP or BestFit are generally preferred) or between one sequence and a large database of sequences (in which case FASTA or BLASTA are preferred).

Synthesis

It will be appreciated by those skilled in the art the nucleic acid and polypeptide molecules described herein may be produced by recombinant and other means.

Nucleic Acid Molecules

The nucleic acid molecules encode a polypeptide comprising the amino acid sequence of an Fhm polypeptide and can readily be obtained in a variety of ways including, without limitation, chemical synthesis, cDNA or genomic library screening, expression library screening and/or PCR amplification of cDNA.

Recombinant DNA methods used herein are generally, those set forth in Sambrook et al. (*Molecular Cloning: A Laboratory Manual*, Cold Spring Harbor Laboratory Press, Cold Spring Harbor, N.Y. (1989)) and/or Ausubel et al., eds., (*Current Protocols in Molecular Biology*, Green Publishers Inc. and Wiley and Sons, NY (1994)).

The present invention provides for nucleic acid molecules as described herein and methods for obtaining such molecules. Where a gene encoding Fhm polypeptide has been identified from one species, all or a portion of that gene may be used as a probe to identify orthologs or related genes from the same species. The probes or primers may be used to screen cDNA libraries from various tissue sources believed to express the Fhm polypeptide In addition, part or all of a nucleic acid molecule having the sequence as set forth in SEQ ID NO: 3 may be used to screen a genomic library to identify and isolate a gene encoding Fhm. Typically, conditions of moderate or high stringency will be employed for screening to minimize the number of false positives obtained from the screen.

Nucleic acid molecules encoding the amino acid sequence of Fhm polypeptides may also be identified by expression cloning, which employs the detection of positive clones based upon a property of the expressed protein. Typically, nucleic acid libraries are screened by the binding of an antibody or other binding partner (e.g., receptor or ligand) to cloned proteins which are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence which encodes the amino acid sequence of an Fhm polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an Fhm polypeptide can be inserted into an expression vector. By introducing the expression vector into an appropriate host, the encoded Fhm polypeptide may be produced in large amounts.

Another method for obtaining a suitable nucleic acid sequence is the polymerase chain reaction (PCR). In this method, cDNA is prepared from poly(A)+RNA or total RNA using the enzyme reverse transcriptase. Two primers, typically complementary to two separate regions of cDNA (oligonucleotides) encoding the amino acid sequence of an Fhm polypeptide, are then added to the cDNA along with a polymerase such as Taq polymerase, and the polymerase amplifies the cDNA region between the two primers.

Another means of preparing a nucleic acid molecule encoding the amino acid sequence of Fhm polypeptide is by chemical synthesis using methods well known to the skilled artisan such as those described by Engels et al., *Angew. Chem. Intl. Ed.*, 28:716-734, 1989. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a Fhm polypeptide will be several hundred nucleotides in length. Nucleic acids larger than about 100 nucleotides can be synthesized as several fragments using these methods. The fragments can then be ligated together to form the full-length nucleotide sequence of a Fhm polypeptide. Usually, the DNA fragment encoding the amino terminus of the polypeptide will have an ATG, which encodes a methionine residue. This methionine may or may not be present on the mature form of the Fhm polypeptide, depending on whether the polypeptide produce din the host cell is designed to be secreted from the cell. Other methods known to the skilled artisan may be used as well.

In certain embodiments, nucleic acid variants contain codons which have been altered for the optimal expression of a Fhm polypeptide in a given host cell. Particular codon alterations will depend upon the Fhm polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh. cod" for codon preference of highly expressed bacterial genes may be used and are provided by the University of Wisconsin Package Version 9.0, Genetics Computer Group, Madison, Wis. Other useful codon frequency tables include "Celegans_high.cod", "Celegans_low.cod", "Drosophila_high.cod", "Human_high.cod", "Maize_high.cod", and "Yeast_high. cod".

In other embodiments, nucleic acid molecules encode Fhm variants with conservative amino acid substitutions as defined above, Fhm variants comprising an addition and/or a deletion of one or more N-linked or O-linked glycosylation sites, or Fhm polypeptide fragments as described above. In addition, nucleic acid molecules may encode any combination of Fhm variants, fragments, and fusion polypeptides described herein provided that DNA's modified in this way code for polypeptides capable of finding one or more members of TNF supergene family of ligands and receptors.

Vectors and Host Cells

A nucleic acid molecule encoding the amino acid sequence of a Fhm polypeptide may be inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a Fhm polypeptide may be amplified/expressed in prokaryotic, yeast, insect (baculovirus systems), and/or eukaryotic host cells. Selection of the host cell will depend in part on whether the Fhm polypeptide is to be post-translationally modified (e.g., glycosylated and/or phosphorylated). If so, yeast, insect, or mammalian host cells are preferable. For a review of expression vectors see Meth. Enz. vol. 185 D.V. Goeddel ed., Academic Press, San Diego Calif., 1990.

Typically, expression vectors used in any of the host cells will contain sequences for plasmid maintenance and for cloning and expression of exogenous nucleotide sequences. Such sequences, collectively referred to as "flanking sequences" (in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag" sequence, i.e., an oligonucleotide molecule located at the 5' or 3' end of the Fhm polypeptide coding sequence; the oligonucleotide molecule encodes polyHis (such as hexaHis), or another "tag" such as FLAG, HA (hemaglutinin influenza virus) or myc for which commercially available antibodies exist. Optionally, the Fhm gene can also be fused in frame at the N-terminal for example to an IgG Fc region. This tag is typically fused to the polypeptide upon expression of the polypeptide, and can serve as a means for affinity purification of the Fhm polypeptide from the host cell although it may also prolong the circulatory half life of a Fhm polypeptide. Affinity purification can be accomplished, for example, by column chromatography using antibodies against the tag as an affinity matrix. Optionally, the tag can subsequently be removed from the purified Fhm polypeptide by various means such as using certain peptidases for cleavage.

Flanking sequences may be homologous (i.e., from the same species and/or strain as the host cell), heterologous (i.e, from a species other than the host cell species or strain), hybrid (i.e., a combination of flanking sequences from more than one source), or synthetic, or the flanking sequence may be native sequences which normally function to regulate Fhm expression. As such, the source of flanking sequences may be any prokaryotic or eukaryotic organism, any vertebrate or invertebrate organism, or any plant, provided that a flanking sequence is functional in, and can be activated by, the host cell machinery.

The flanking sequences useful in the vectors of this invention may be obtained by any of several methods well known in the art. Typically, flanking sequences useful herein other than the sequences flanking the Fhm gene will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with suitable oligonucleotide and/or flanking sequence fragments from the same or another species.

Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other method known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of the Fhm polypeptide. If the vector of choice does not contain an origin of replication site, one may be chemically synthesized based on a known sequence, and ligated into the vector. For example, the origin of replication from the plasmid pBR322 (Product No. 303-3s, New England Biolabs, Beverly, Mass.) is suitable for most Gram-negative bacteria and various origins (e.g., SV40, polyoma, adenovirus, vesicular stomatitis virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding regions and serves to terminate transcription. Usually, a transcription termination sequence in prokaryotic cells is a G-C rich fragment followed by a poly T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene which will be expressed. Amplification is the process wherein genes which are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure which only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes Fhm. As a result, increased quantities of Fhm are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the Fhm polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct the secretion of Fhm polypeptide out of the host cell where it is synthesized. Typically, a nucleotide sequence encoding the signal sequence is positioned in the coding region of the Fhm nucleic acid molecule, or directly at the 5' end of the Fhm polypeptide coding region. Many signal sequences have been identified, and any of those that are functional in the selected host cell may be used in conjunction with the Fhm gene or cDNA. Therefore, a signal sequence may be homologous (naturally occurring) or heterologous to the Fhm gene or cDNA, and may be homologous or heterologous to the Fhm gene or cDNA. Additionally, a signal sequence may be chemically synthesized using methods described herein. In most cases, the secretion of an Fhm polypeptide from the host cell via the presence of a signal peptide will result in the removal of the signal peptide from the Fhm polypeptide.

The signal sequence may be a component of the vector, or it may be a part of Fhm nucleic acid molecule that is inserted into the vector. The native Fhm DNA encodes a signal sequence at the amino terminus of the protein that is cleaved during post-translational processing of the molecule to form the mature Fhm protein product. Included within the scope of this invention are Fhm nucleotides with the native signal sequence as well as Fhm nucleotides wherein the native signal sequence is deleted and replaced with a heterologous signal sequence. The heterologous signal sequence selected should be one that is recognized and processed, i.e., cleaved by a signal peptidase, by the host cell. For prokaryotic host cells that do not recognize and process the native Fhm signal sequence, the signal sequence is substituted by a prokaryotic signal sequence selected, for example, from the group of the alkaline phosphatase, penicillinase, or heat-stable enterotoxin II leaders. For yeast secretion, the native Fhm signal sequence may be substituted by the yeast invertase, alpha factor, or acid phosphatase signal sequences. For mammalian cell expression the native signal sequence of the Fhm polypeptide is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add presequences, which also may affect glycosylation. The final protein product may have, in the −1 position (relative to the first amino acid of the mature protein), one or more additional amino acid residues incident to expression, which may not have been totally removed. For example, the final protein product may have one or two amino acids found in the peptidase cleavage site, attached to the N-terminus. Alternatively, use of some enzyme cleavage sites may result in a slightly truncated form of the desired Fhm polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the Fhm gene, especially where the gene used is a full length genomic sequence or a fragment thereof. Where the intron is not naturally occurring within the gene (as for most cDNAs), the intron(s) may be obtained from another source. The position of the intron with respect to flanking sequences and the Fhm gene is generally important, as the intron must be transcribed to be effective. Thus, when an Fhm cDNA molecule is being transcribed, the preferred position for the intron is 3' to the transcription start site, and 5' to the polyA transcription termination sequence. Preferably, the intron or introns will be located on one side or the other (i.e., 5' or 3') of the cDNA such that it does not interrupt the this coding sequence. Any intron from any source, including viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector.

The expression and cloning vectors of the present invention will each typically contain a promoter that is recognized by the host organism and operably linked to the molecule encoding the Fhm polypeptide.

Promoters are untranscribed sequences located upstream (5') to the start codon of a structural gene (generally within about 100 to 1000 bp) that control the transcription and translation of a particular molecule, such as that encoding Fhm. Promoters are conventionally grouped into one of two classes, inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continuous gene production; that is, there is little or no control over gene expression. A large number of promoters, recognized by a variety of potential host cells, are well known. A suitable promoter is operably linked to the DNA encoding Fhm by removing the promoter from the source DNA by restriction enzyme digestion and inserting the desired promoter sequence into the vector. The native Fhm promoter sequence may be used to direct amplification and/or expression of Fhm encoding nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include, but are not limited to the beta-lactamase and lactose promoter systems; alkaline phosphatase, a tryptophan (trp) promoter system; and hybrid promoters such as the tac promoter. Other known bacterial promoters and also suitable. Their sequences have been published, thereby enabling one skilled in the art to ligate them to the desired DNA sequence(s), using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowl pox virus, adenovirus (such as Adenovirus 2), bovine papilloma virus, avian sarcoma virus, cytomegalovirus, retrovirus, hepatitis-B virus, herpes virus and most preferably Simian Virus 40 (SV40). Other suitable mammalian promoters include heterologous mammalian promoters, e.g., heat-shock promoters and the actin promoter.

Additional promoters which may be of interest in controlling Fhm transcription include, but are not limited to, the SV40 early promoter region (Bernoist and Chambon, *Nature*, 290:304-310, 1981); the CMV promoter; the promoter contained in the 3' long terminal repeat (LTR) of Rous sarcoma virus (RSV) (Yamamoto, et al., Cell, 22:787-797, 1980); the herpes thymidine kinase (TK) promoter (Wagner et al, *Proc. Natl. Acad. Sci. U.S.A.*, 78:144-1445, 1981); the regulatory sequences of the metallothionine gene (Brinster et al., *Nature*, 296:39-42, 1982); prokaryotic expression vectors such as the beta-lactamase promoter (Villa-Kamaroff, et al., *Proc. Natl. Acad. Sci. U.S.A.*, 75:3727-3731, 1978); or the tac promoter (DeBoer, et al., *Proc. Natl. Acad. Sci. U.S.A.*, 80:21-25, 1983). Also of use are the following animal transcriptional control regions, which exhibit tissue specificity and have been utilized in transgenic animals: the elastase I gene control region which is active in pancreatic acinar cells (Swift et al., *Cell*, 38:639-646, 1984; Ornitz et al., *Cold Spring Harbor Symp. Quant. Biol.* 50:399-409, 1986; MacDonald, *Hepatology*, 7:425-515, 1987); the insulin gene control region which is active in pancreatic beta cells (Hanahan, *Nature*, 315:115-122, 1985); the immunoglobulin gene control region which is active in lymphoid cells (Grosschedl et al., *Cell*, 38:647-658, 1984; Adames et al., *Nature*, 318:533-538, 1985; Alexander et al., *Mol. Cell. Biol.*, 7:1436-1444, 1987); the mouse mammary tumor virus control region which is active in testicular, breast, lymphoid and mast cells (Leder et al., *Cell*, 45:485-495, 1986), the albumin gene control region which is active in liver (Pinkert et al., *Genes and Devel.*, 1:268-276, 1987); the alphafetoprotein gene control region which is active in liver (Krumlauf et al., *Mol. Cell. Biol.*, 5:1639-1648, 1985; Hammer et al., *Science*, 235:53-58, 1987); the alpha 1-antitrypsin gene control region which is active in the liver (Kelsey et al., *Genes and Devel.*, 1:161-171, 1987); the beta-globin gene control region which is active in myeloid cells (Mogram et al., *Nature*, 315:338-340, 1985; Kollias et al., *Cell*, 46:89-94, 1986); the myelin basic protein gene control region which is active in oligodendrocyte cells in the brain (Readhead et al., *Cell*, 48:703-712, 1987); the myosin light chain-2 gene control region which is active in skeletal muscle (Sani, *Nature*, 314:283-286, 1985); and the gonadotropic releasing hormone gene control region which is active in the hypothalamus (Mason et al., *Science*, 234:1372-1378, 1986).

An enhancer sequence may be inserted into the vector to increase the transcription of a DNA encoding a Fhm polypeptide of the present invention by higher eukaryotes. Enhancers are cis-acting elements of DNA, usually about 10-300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-fetoprotein and insulin). Typically, however, an enhancer from a virus will be used. The SV40 enhancer, the cytomegalovirus early promoter enhancer, the polyoma enhancer, and adenovirus enhancers are exemplary enhancing elements for the activation or upregulation of eukaryotic promoters. While an enhancer may be spliced into the vector at a position 5' or 3' to Fhm nucleic acid molecules, it is typically located at a site 5' from the promoter.

Expression vectors of the invention may be constructed from a starting vector such as a commercially available vector. Such vectors may or may not contain all of the desired flanking sequences. Where one or more of the desired flanking sequences set forth above are not already present in the vector, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen Company, Carlsbad, Calif.), pBSII (Stratagene Company, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII; Invitrogen), pDSR-alpha (PCT Publ. No. WO 90/14364) and pFastBacDual (Gibco-Brl Grand Island, N.Y.).

Additional suitable vectors include, but are not limited to, cosmids, plasmids or modified viruses, but it will be appreciated that the vector system must be compatible with the selected host cell. Such vectors include, but are not limited to plasmids such as Bluescript® plasmid derivatives (a high copy number ColE1-based phagemid, Stratagene Cloning Systems Inc., La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.).

After the vector has been constructed and a nucleic acid molecule encoding an Fhm polypeptide has been inserted into the proper site of the vector, the completed vector may be inserted into a suitable host cell for amplification and/or polypeptide expression. The transformation of an expression vector for an Fhm polypeptide into a selected host cell may be accomplished by well-known methods such as transfection, infection, calcium chloride, electroporation, microinjection, lipofection or the DEAE-dextran method or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (yeast, insect, or vertebrate cells). The host cell, when cultured under appropriate conditions, synthesizes an Fhm polypeptide which can subsequently be collected from the culture medium (if the host cell secretes it into the medium) or directly from the host cell producing it (if it is not secreted). The selection of an appropriate host cell will depend upon various factors, such as desired expression levels, polypeptide modifications that desirable or necessary for activity, (such as glycosylation or phosphorylation), and ease of folding into a biologically active molecule.

Yeast and mammalian cells are preferred hosts of the present invention. The use of such hosts provides substantial advantages in that they can also carry out post-translational peptide modifications including glycosylation. A number of recombinant DNA strategies exist which utilize strong promoter sequences and high copy number of plasmids which can be utilized for production of the desired proteins in these hosts.

Yeast recognize leader sequences on cloned mammalian gene products and secrete peptides bearing leader sequences (i.e., pre-peptides). Mammalian cells provide post-translational modifications to protein molecules including correct folding or glycosylation at correct sites.

Mammalian cells which may be useful as hosts include cells of fibroblast origin such as VERO or CHO-K1, and their derivatives. For a mammalian host, several possible vector systems are available for the expression of the desired Fhm protein. A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene which has a high level of expression. Alternatively, promoters from mammalian expression products, such as actin, collagen, myosin, etc., may be employed. Transcriptional initiation regulatory signals may be selected which allow for repression or activation, so that expression of the genes can be modulated. Useful signals are regulatory signals which are temperature-sensitive so that by varying the temperature, expression can be repressed or initiated, or are subject to chemical regulation, e.g., metabolite.

As is widely known, translation of eukaryotic mRNA is initiated at the codon which encodes the first methionine. For this reason, it is preferable to ensure that the linkage between a eukaryotic promoter and a DNA sequence which encodes the desired receptor molecule does not contain any intervening codons which are capable of encoding a methionine (i.e., AUG). The presence of such codons results either in the formation of a fusion protein (if the AUG codon is in the same reading frame as the desired receptor molecule encoding DNA sequence) or a frame-shift mutation (if the AUG codon is not in the same reading frame as the desired Fhm protein encoding sequence).

The expression of the Fhm proteins can also be accomplished in procarvotic cells. Preferred prokaryotic hosts include bacteria such as *E. coli, Bacillus, Streptomyces, Pseudomonas, Salmonella, Serratia*, etc. The most preferred prokaryotic host is *E. coli*. Bacterial hosts of particular interest include *E. coli* K12 strain 294 (ATCC 31446), *E. coli* X1776 (ATCC 31537), *E. coli* W3110 (F$^-$, lambda$^-$, prototrophic (ATCC 27325)), and other enterobacteria (such as *Salmonella typhimurium* or *Serratia marcescens*), and various *Pseudomonas* species. The prokaryotic host must be compatible with the replicon and control sequences in the expression plasmid.

To express the desired Fhm protein in a prokaryotic cell (such as, for example, *E. coli, B. subtilis, Pseudomonas, Streptomyces*, etc.), it is necessary to operably link the desired receptor molecule encoding sequence to a functional prokaryotic promoter. Such promoters may be either constitutive or, more preferably, regulatable (i.e., inducible or derepressible). Examples of constitutive promoters include the int promoter of bacteriophage λ, and the bla promoter of the β-lactamase gene of pBR322, etc. Examples of inducible prokaryotic promoters include the major right and left promoters, of bacteriophage λ ($P_L$ and $P_R$), the trp, recA, lacZ, lacI, gal, and tac promoters of *E. coli*, the α-amylase (Ulmanen et al., *J. Bacteriol.* 162:176-182, 1985), the σ-28-specific promoters of *B. subtilis* (Gilma et al., *Gene* 32:11-20, 1984), the promoters of the bacteriophages of *Bacillus* (Gryczan, T. J., In: *The Molecular Biology of the Bacilli*, Academic Press, Inc., New York, 1982), and *Streptomyces* promoters (Ward et al., *Mol. Gen. Genet.* 203:468-478 1986). Prokaryotic promoters are reviewed by Glick, (*J. Ind. Microbiol.* 1:277-282, 1987); Cenatiempo, *Biochimie* 68:505-516, 1986); and Gottesman, *Ann. Rev. Genet.* 18:415-442 1984).

Proper expression in a prokaryotic cell also requires the presence of a ribosome binding site upstream from the gene-encoding sequence. Such ribosome binding sites are disclosed, for example, by Gold et al. (*Ann. Rev. Microbiol.* 35:365-404, 1981).

The desired Fhm protein encoding sequence and an operably linked promoter may be introduced into a recipient prokaryotic or eukaryotic cell either as a non-replicating DNA (or RNA) molecule, which may either be linear or, more preferably, a closed covalent circular molecule. Since such molecules are incapable of autonomous replication, the expression of the desired receptor molecule may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may complement an auxotrophy in the host (such as leu21, or ura3, which are common yeast auxotrophic markers), biocide resistance, e.g., antibiotics, or heavy metals, such as copper, or the like. The selectable marker gene can either be directly linked to the DNA gene sequences to be expressed, or introduced into the same cell by co-transfection.

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include, for e.g. the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Any of a series of yeast gene expression systems can also be utilized. Examples of such expression vectors include the yeast 2-micron circle, the expression plasmids YEP13, YVP and YRP, etc., or their derivatives. Such plasmids are well known in the art (Botstein, et al., *Miami Wntr. Skimp.* 19:265-274 (1982); Broach, In: *The Molecular Biology of the Yeast Saccharomyces: Life Cycle and Inheritance*, Cold Spring Harbor Laboratory, Cold Spring Harbor, N.Y., p. 445-470 (1981); Broach, *Cell* 28:203-204 1982).

For a mammalian host, several possible vector systems are available for expression. One class of vectors utilize DNA elements which provide autonomously replicating extra-chromosomal plasmids, derived from animal viruses such as bovine papilloma virus, polyoma virus, adenovirus, or SV40 virus. A second class of vectors relies upon the integration of the desired gene sequences into the host chromosome. Cells which have stably integrated the introduced DNA into their chromosomes may be selected by also introducing one or more markers which allow selection of host cells which contain the expression vector. The marker may provide for prototropy to an auxotrophic host, biocide resistance, e.g., antibiotics, or heavy metals, such as copper or the like. The selectable marker gene can either be directly linked to the DNA sequences to be expressed, or introduced into the same cell by co-transformation. Additional elements may also be needed for optimal synthesis of mRNA. These elements may include splice signals, as well as transcription promoters, enhancers, and termination signals. The cDNA expression vectors incorporating such elements include those described by Okayama, *Mol. Cell. Biol.* 3:280 1983, and others. Preferred eukaryotic vectors include PWLNEO, PSV2CAT, POG44, PXTl, pSG, pSVK3, pBPV, pMSG, pSVL (Pharmacia).

Preferred prokaryotic vectors include plasmids such as those capable of replication in *E. coli* such as, for example, pBR322, ColE1, pSC101, pACYC 184, πVX, pQE70, pQE60, pQE9, pBG, pD10, Phage script, psix 174, pbmescript SK, pbsks, pNH$_8$A, pNHIBa, pNH$_{18}$A, pNH$_{46}$A (SL rare gone), ptrc99a, pKK223-3, pKK233-3, pDR540, pRIT5. Such plasmids are, for example, disclosed by Maniatis, T., et al. (In: *Molecular Cloning, A Laboratory Manual*, Cold Spring Harbor Press, Cold Spring Harbor, N.Y. (1982)). *Bacillus* plasmids include pC194, pC221, pT127, etc. Such plasmids are disclosed by Gryczan, T. (In: *The Molecular Biology of the Bacilli*, Academic Press, New York (1982), pp. 307-329). Suitable *Streptomyces* plasmids include pISJ101 (Kendall, et al., *J. Bacteriol.* 169:4177-4183 1987), and *Streptomyces* bacteriophages such as φC31 (Chater, et al., In: *Sixth International Symposium on Actinomycetales Biology*, Akademiai Kaido, Budapest, Hungary, 1986, pp 45-541). *Pseudomonas* plasmids are reviewed by John, et al. (*Rev. Infect. Dis.* 8:693-704, 1986, and Izaki, K. (*Jpn. J. Bacteriol.* 33:729-742 1978). However, any other plasmid or vector may be used as long as they are replicable and viable in the host cell.

Once the vector or DNA sequence containing the constructs has been prepared for expression, the DNA constructs may be introduced into an appropriate host. Various techniques may be employed, such as a protoplast fusion, calcium phosphate precipitation, electroporation or other conventional techniques. After the fusion, the cells are grown in media and screened for appropriate activities. Expression of the sequence results in the production of the Fhm protein.

Suitable host cells or cell lines may be mammalian cells, such as Chinese hamster ovary cells (CHO; ATCC No. CCL61), CHO DHFR cells (Urlaub et al. *Proc. Natl. Acad. Sci. U.S.A*, 97: 4216-4220,1980) human embryonic kidney (HEK), 293 or 293T cells (ATCC No. CRL 1573), or 3T3 cells (ATCC No. CRL920). The selection of suitable mammalian host cells and methods for transformation, culture, amplification, screening, product production and purification are known in the art. Other suitable mammalian cell lines, are the monkey COS-1 (ATCC No. CRL 1650) and COS-7 (ATCC No. CRL 1651) cell lines, and the CV-1 (ATCC No. CCL70) cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominant acting selection gene. Other suitable mammalian cell lines include, but are not limited to, mouse neuroblastoma N2A cells, HeLa, mouse L-929 cells, 3T3 lines derived from Swiss, Balb-c or NIH mice, BHK or HaK hamster cell lines, which are available from the ATCC. Each of these cell lines is known by and available to those skilled in the art of protein expression.

Similarly useful as host cells suitable for the present invention are bacterial cells. For example, the various strains of *E. coli* (e.g., HB101, DH5α (ATCC No. 33694), DH10, and MC1061 (ATCC No. 53330)) are well-known as host cells in the field of biotechnology. Various strains of *B. subtilis*, *Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast strains include, for example, *Saccharomyces cerevisiae* and *Pichia pastoris*.

Additionally, where desired, insect cell systems may be utilized in the methods of the present invention. Such systems are described for example in Kitts et al. (*Biotechniques*, 14:810-817, 1993), Lucklow (*Curr. Opin. Biotechnol.*, 4:564-572, 1993) and Lucklow et al. (*J. Virol.*, 67:4566-4579, 1993). Preferred insect cells are Sf-9 and Hi5 (Invitrogen, Carlsbad, Calif.).

One may also use transgenic animals to express glycosylated Fhm polypeptides. For example, one may use a transgenic milk-producing animal (e.g. a cow or goat) and obtain the present glycosylated polypeptide in the animal milk. One may also use plants to produce Fhm polypeptides; however, in general, the glycosylation occurring in plants is different from that produced in mammalian cells, and may result in a glycosylated product which is not suitable for human therapeutic use.

Polypeptide Production

Host cells comprising an Fhm polypeptide expression vector (i.e., transformed or transfected) may be cultured using standard media well known to the skilled artisan. The media will usually contain all nutrients necessary for the growth and survival of the cells. Suitable media for culturing *E. coli* cells include for example, Luria Broth (LB) and/or Terrific Broth (TB). Suitable media for culturing eukaryotic cells are Rosewell Park Memorial Media 1640 (RPMI 1640), Minimal Essential Media (MEM), Dulbecco's Modified Eagles Media (DMEM), all of which may be supplemented with serum and/or growth factors as indicated by the particular cell line being cultured. A suitable medium for insect cultures is Grace's medium supplemented with yeastolate, lactalbumin hydrolysate and/or fetal calf serum as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth media include ampicillin, tetracycline and neomycin. The amount of Fhm polypeptide produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If a Fhm polypeptide has been designed to be secreted from the host cells, the majority of polypeptide may be found in the cell culture medium. If however, the Fhm polypeptide is not secreted from the host cells, it will be present in the cytoplasm and/or nucleus (for eukaryotic host cells) or in the cytosol (bacterial host cells).

The intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a Fhm polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The Fhm polypeptide in its now soluble form can then be analyzed using gel electrophoresis, immunoprecipitation or the like. If it is desired to isolate the Fhm polypeptide, isolation may be accomplished using standard methods such as those described herein and in Marston et al. (*Meth. Enz.,* 182:264-275 1990).

In some cases, a Fhm polypeptide may not be biologically active upon isolation. Various methods for "refolding" or converting the polypeptide to its tertiary structure and generating disulfide linkages, can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/ oxidation solution will also contain a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol(DTT)/dithiane DTT, 2-mercaptoethanol($\beta$ME)/dithio-$\beta$(ME). A cosolvent is necessary to increase the efficiency of the refolding, and the more common reagents used for this purpose include glycerol, polyethylene glycol of various molecular weights, arginine and the like.

If inclusion bodies are not formed to a significant degree upon expression of a Fhm polypeptide, then the polypeptide will be found primarily in the supernatant after centrifugation of the cell homogenate. The polypeptide and may be further isolated from the supernatant using methods such as those described herein.

The purification of an Fhm polypeptide from solution can be accomplished using a variety of techniques. If the polypeptide has been synthesized such that it contains a tag such as Hexahistidine (Fhm polypeptide/hexaHis) or other small peptide such as FLAG (Eastman Kodak Co., New Haven, Conn.) or myc (Invitrogen, Carlsbad, Calif.) at either its carboxyl or amino terminus, it may be purified in a one-step process by passing the solution through an affinity column where the column matrix has a high affinity for the tag.

For example, polyhistidine binds with great affinity and specificity to nickel, thus annickel; thus affinity column of nickel (such as the Qiagen® nickel columns) can be used for purification of Fhm polypeptide/polyHis. See for example, Ausubel et al., eds., *Current Protocols in Molecular Biology,* Section 10.11.8, John Wiley & Sons, New York 1993.

Additionally, the Fhm polypeptide may be purified through the use of a monoclonal antibody which is capable of specifically recognizing and binding to the Fhm polypeptide.

Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

Fhm polypeptides, fragments, and/or derivatives thereof may also be prepared by chemical synthesis methods (such as solid phase peptide synthesis) using techniques known in the art, such as those set forth by Merrifield et al., (*J. Am. Chem. Soc.,* 85:2149, 1963), Houghten et al. (*Proc Natl Acad. Sci. USA,* 82:5132, 1985), and Stewart and Young (*Solid Phase Peptide Synthesis,* Pierce Chemical Co., Rockford, Ill., 1984).

Such polypeptides may be synthesized with or without a methionine on the amino terminus. Chemically synthesized Fhm polypeptides or fragments may be oxidized using methods set forth in these references to form disulfide bridges. Chemically synthesized Fhm polypeptides, fragments or derivatives are expected to have comparable biological activity to the corresponding Fhm polypeptides, fragments or derivatives produced recombinantly or purified from natural sources, and thus may be used interchangeably with recombinant or natural Fhm polypeptide.

Another means of obtaining Fhm polypeptide is via purification from biological samples such as source tissues and/or fluids in which the Fhm polypeptide is naturally found. Such purification can be conducted using methods for protein purification as described above. The presence of the Fhm polypeptide during purification may be monitored, for example, using an antibody prepared against recombinantly produced Fhm polypeptide or peptide fragments thereof.

A number of additional methods for producing nucleic acids and polypeptides are known in the art, and the methods can be used to produce polypeptides having specificity for Fhm. See for example, Roberts et al., *Proc. Natl. Acad. Sci. USA,* 94:12297-12303, 1997, which describes the production of fusion proteins between an mRNA and its encoded peptide. See also Roberts, *Curr. Opin. Chem. Biol.* 3:268-273, 1999.

Additionally, U.S. Pat. No. 5,824,469 describes methods of obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those which exhibit a predetermined biological function. From that subpopulation, oligonucleotides capable of carrying out the desired biological function are isolated. U.S. Pat. Nos. 5,763,192, 5,814,476, 5,723,323, and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in PCT/US98/20094 (WO99/15650) filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell which is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive IL-17 like protein expression libraries, which can subsequently be used for high throughput phenotypic screening in a variety of assays, such as biochemical assays, cellular assays, and whole organism assays (e.g., plant, mouse, etc.).

Proteins, Polypeptides, Fragments, Variants and Muteins of Fhm:

Polypeptides of the invention include isolated Fhm polypeptides and polypeptides related thereto including fragments, variants, fusion polypeptides, and derivatives as defined hereinabove.

Fhm fragments of the invention may result from truncations at the amino terminus (with or without a leader sequence), truncations at the carboxy terminus, and/or deletions internal to the polypeptide. Most deletions and insertions, and substitutions in particular, are not expected to produce radical changes in the characteristics of the Fhm protein. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the Fhm-encoding nucleic acid, expression of the variant nucleic acid in recombinant cell culture, and, optionally, purification from the cell culture, for example, by immunoaffinity adsorption on a polyclonal anti-Fhm antibody column (to absorb the variant by binding it to at least one remaining immune epitope). In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such Fhm polypeptides fragments may optionally comprise an amino terminal methionine residue.

Fhm polypeptide variants of the invention include one or more amino acid substitutions, additions and/or deletions as compared to SEQ ID NO: 4. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, as defined above, or non-conservative or any combination thereof. More particularly, Fhm variants may comprise the amino acid sequence set out as SEQ ID NO: 4, wherein one or more amino acids from the group consisting of amino acids 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41.42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176 up to 251 is substituted with another amino acid. The variants may have additions of amino acid residues either at the carboxy terminus or at the amino terminus (with or without a leader sequence).

Preferred Fhm polypeptide variants include glycosylation variants wherein the number and/or type of glycosylation sites has been altered compared to native Fhm polypeptide. In one embodiment, Fhm variants comprise a greater or a lesser number of N-linked glycosylation sites. A N-linked glycosylation site is characterized by the sequence: Asn-X-Ser or Thr, where the amino acid residue designated as X may be any type of amino acid except proline. Substitution(s) of amino acid residues to create this sequence provides a potential new site for addition of a N-linked carbohydrate chain. Alternatively, substitutions to eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created.

One skilled in the art will be able to determine suitable variants of the native Fhm polypeptide using well known techniques. For example, one may be able to predict suitable areas of the molecule that may be changed without destroying biological activity. Also, one skilled in the art will realize that even areas that may be important for biological activity or for structure may be subject to conservative amino acid substitutions without destroying the biological activity or without adversely affecting the polypeptide structure.

For predicting suitable areas of the molecule that may be changed without destroying activity, one skilled in the art may target areas not believed to be important for activity. For example, when similar polypeptides with similar activities from the same species or from other species are known, one skilled in the art may compare the amino acid sequence of Fhm polypeptide to such similar polypeptides. After making such a comparison, one skilled in the art would be able to determine residues and portions of the molecules that are conserved among similar polypeptides. One skilled in the art would know that changes in areas of the Fhm molecule that are not conserved would be less likely to adversely affect biological activity and/or structure. One skilled in the art would also know that, even in relatively conserved regions, one could have likely substituted chemically similar amino acids for the naturally occurring residues while retaining activity (e.g. conservative amino acid residue substitutions).

Also, one skilled in the art may review structure-function studies identifying residues in similar polypeptides that are important for activity or structure. In view of such a comparison, one skilled in the art can predict the importance of amino acid residues in Fhm that correspond to amino acid residues that are important for activity or structure in similar polypeptides. One skilled in the art may opt for chemically similar amino acid substitutions for such predicted important amino acid residues of Fhm.

If available, one skilled in the art can also analyze the crystal structure and amino acid sequence in relation to that structure in similar polypeptides. In view of that information, one skilled in the art may be able to predict the alignment of amino acid residues of Fhm polypeptide with respect to its three dimensional structure. One skilled in the art may choose not to make radical changes to amino acid residues predicted to be on the surface of the protein, since such residues may be involved in important interactions with other molecules.

Moreover, one skilled in the art can generate test variants containing a single amino acid substitution at each amino acid residue. The variants can be screened using activity assays disclosed in this application. Such variants are used to gather information about suitable variants. For example, if one discovered that a change to a particular amino acid residue resulted in destroyed activity, variants with such a change would be avoided. Thus, based on information gathered from such experiments, when attempting to find additional acceptable variants, one skilled in the art can determine the amino acids where further substitutions should be avoided either alone or in combination with other mutations.

Fhm polypeptide analogs of the invention can be determined by comparing the amino acid sequence of Fhm polypeptide with related family members. Exemplary Fhm polypeptide related family members include, but are not limited to, the TNF-α, TNK-β, LyT-β, FasL, CD40L, CD30L, OPGL, and TRAIL. This comparison can be accomplished by using a Pileup alignment (Wisconsin GCG Program Package) or an equivalent (overlapping) comparison with multiple family members within conserved and non-conserved regions.

As shown in FIG. 1, the predicted amino acid sequence of Fhm polypeptide (SEQ ID NO: 4) is aligned with the corresponding regions of human FasL, mouse FasL, rat FasL, human CD40L, mouse CD40L, mouse OPGL, human OPGL, human TRAIL, mouse TRAIL, human CD30L, human CD30L, human LyT-β, mouse LyT-β, human TNF-β, mouse TNF-β, human TNF-α and mouse TNF-α. (SEQ ID NOS: 5-21). Other Fhm polypeptide analogs can be determined using these or other methods known to those of skill in the art. These overlapping sequences provide guidance for conservative and non-conservative amino acids substitutions resulting in additional Fhm analogs. It will be appreciated that these amino acid substitutions can consist of naturally occurring or non-naturally occurring amino acids. For example, as depicted in FIG. 1, alignment of the B/B' loop and D/E loop of these ligands indicates potential Fhm analogs may have the Val residue at position 153 substituted with a Ile, Met, Leu, Phe, Ala or Norleucine residue, the Tyr residue at position 147 may be substituted with, or the Phe residue at position 154 may be substituted with Leu, Val, Ile, Ala, or Tyr residue. Further, the Ser residue at position 151 may be substituted with Thr, Ala, or Cys, the Gly residue at 145 may be substituted with Pro or Ala, and the Tyr at position 150 may be substituted with Trp, Phe, Thr or Ser.

Fhm fusion polypeptides of the invention comprise Fhm polypeptides, fragments, variants, or derivatives fused to one or more heterologous peptides or proteins. Heterologous peptides and proteins include, but are not limited to, an epitope to allow for detection and/or isolation of a Fhm fusion polypeptide, a transmembrane receptor protein or a portion thereof, such as an extracellular domain, or a transmembrane, a ligand or a portion thereof which binds to a transmembrane receptor protein, an enzyme or portion thereof which is catalytically active, a protein or peptide which promotes oligomerization, such as leucine zipper domain, and a protein or peptide which increase stability, such as an immunoglobulin constant region. A Fhm polypeptide may be fused to itself or to a fragment, variant, or derivative thereof. Fusions may be made either at the amino terminus or at the carboxy terminus of a Fhm polypeptide, and may be direct with no linker or adapter molecule or may be through a linker or adapter molecule, such as one or more amino acid residues up to about 20 amino acids residues, or up to about 50 amino acid residues. Alternatively, the Fhm fusion protein may comprise one or two Fhm polypeptides covalently linked to one or two TNF ligand polypeptide(s), or a member of the TNF ligand family or a cytokine receptor such as interleukin-1 (IL-1) polypeptide. The ligands preferably are produced as fusion proteins using recombinant DNA technology. A linker or adapter molecule may also be designed with a cleavage site for a DNA restriction endonuclease or for proteolytic cleavage to allow for separation and subsequent folding of the fused moieties.

Also envisioned as a part of the invention are circularly permuted structural analogs of the Fhm polypeptide.

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., *Proc. Natl. Acad. Sci. U.S.A.* 76:3218-3222, 1979; Teather & Erfle, *J. Bacteriol.* 172:3837-3841, 1990; Schimming et al., *Eur. J. Biochem.* 204:13-19, 1992; Yamiuchi and Minamikawa, *FEBS Lett* 260:127-130, 1991; MacGregor et al., *FEBS Lett.* 378:263-266, 1996). The first in vitro application of this type of rearrangement to proteins was described by Goldenberg and Creighton (*J. Mol. Biol.* 165:407-413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain.

This approach has been applied to proteins which range in size from 58 to 462 amino acids (Goldenberg & Creighton, *J. Mol. Biol.* 165:407-413, 1983; Li & Coffino, *Mol. Cell. Biol.* 13:2377-2383, 1993). The proteins examined have represented a broad range of structural classes, including proteins that contain predominantly α-helix (interleukin-4; Kreitman et al., *Cytokine* 7:311-318, 1995), predominantly β-sheet (interleukin-1; Horlick et al., *Protein Eng.* 5:427-431, 1992), or mixtures of the two (yeast phosphoribosyl anthranilate isomerase; Luger et al., *Science* 243:206-210, 1989).

In a preferred embodiment, a Fhm polypeptide, fragment, variant and/or derivative is fused to an Fc region of human IgG. In one example, a human IgG hinge, $CH_2$ and CH3 region may be fused at either the N-terminus or C-terminus of the Fhm polypeptides using methods known to the skilled artisan. In another example, a portion of a hinge regions and CH2 and CH3 regions may be fuse. The Fhm Fc-fusion polypeptide so produced may be purified by use of a Protein A affinity column (Pierce, Rockford, Ill.). In addition, peptide and proteins fused to an Fc region have been found to exhibit a substantially greater half-life in vivo than the unfused counterpart. Also, a fusion to an Fc region allows for dimerization/multimerization of the fusion polypeptide. The Fc region may be naturally occurring Fc region, or may be altered to improve certain qualities such as therapeutic qualities, circulation time, reduce aggregation, etc.

Fhm polypeptide derivatives are also included in the scope of the present invention. Covalent modifications of the Fhm proteins of the present invention are included within the scope of this invention. Variant Fhm proteins may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with α-haloacetates (and corresponding amines), such as chloroacetic acid or chloroacetamide, to give carboxymethyl or carbocyamidomethyl derivatives. Cysteinyl residues also are derivatized by reaction with bromotrifluoroacetone, α-bromo-β(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, orchloro-7-nitrobenzo-2-oxa-1,3-diazole.

Histidyl residues are derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylissurea; 2,4 pentanedione; and transaminase catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine Epsilon-amino group.

The specific modification of tyrosyl residues per se has been studied extensively, with particular interest in introducing spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides ($R^1$) such as 1-cyclohexyl-3-(2-morpholinyl-(4-ethyl) carbodiimide or 1-ethyl-3 (4 azonia 4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the Fhm protein(s)/polypeptide to water-insoluble support matrixes or surfaces for use in the method for cleaving the Fhm protein-fusion polypeptide to release and recover the cleaved polypeptide. Commonly used crosslinking agents include, e.g., 1,1-bis(diazoacetyl)-2-phenylethane, glutaraldehyde, N-hydroxysuccinimide esters, for example, esters with 4-azidosalicylic acid, homo-bifunctional imidoesters, including disuccinimidyl esters such as 3,3'-dithiiobis(succinimidylpropioonate), and bifunctional maleimides such as bix-N-maleimido-1,8-octane. Derivatizing agents such as methyl-3-[p-azidophenyl) dithio]propioimidate yield photoactivatable intermediates that are capable of forming cross links in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247, 642; 4,229,537; and 4,330,440, incorporated herein by reference, are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or theonyl residues, methylation of the α-amino groups of lysine, arginine, and histidine side chains (T. E. Creighton, *Proteins: Structure and Molecule Properties*, W.H. Freeman & Co., San Francisco, pp. 79-86,1983), acetylation of the N-terminal amine, and, in some instances, amidation of the C-terminal carboxyl groups. Such derivatives are chemically modified Fhm polypeptide compositions in which Fhm polypeptide is linked to a polymer. The polymer selected is typically water soluble so that the protein to which it is attached does not precipitate in an aqueous environment, such as a physiological environment. The polymer selected is usually modified to have a single reactive group, such as an active ester for acylation or an aldehyde for alkylation, so that the degree of polymerization may be controlled as provided for in the present methods. The polymer may be of any molecular weight, and may be branched or unbranched. Included within the scope of the Fhm polypeptide polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 k kDa to about 100 kDa (the term "about" indicating that in preparations of a water soluble polymer, some molecules will weigh more, some less, than the stated molecular weight). The average molecular weight of each polymer is between about 5 kDa and 5 kDa, about 50 kDa, more preferably between about 12 kDa to about 40 kDa and most preferably between about 20 kDa to about 35 kDa.

Suitable water soluble polymers or mixtures thereof include, but are not limited to, N-linked or O-linked carbohydrates, sugars, phosphates, carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran, of, for example about 6 kD), cellulose; cellulose; other carbohydrate-based polymers, poly-(N-vinyl pyrrolidone) polyethylene glycol, propylene glycol homopolymers, a polypropylene oxide/ethylene oxide copolymer, polyoxyethylated polyols (e.g., glycerol) and polyvinyl alcohol. Also encompassed by the present invention are bifunctional crosslinking molecules which may be used to prepare covalently attached multimers of the polypeptide comprising the amino acid sequence of SEQ ID NO: 4 or an Fhm polypeptide variant.

In general, chemical derivatization may be performed under any suitable condition used to react a protein with an activated polymer molecule. Methods for preparing chemical derivatives of polypeptides will generally comprise the steps of (a) reacting the polypeptide with the activated polymer molecule (such as a reactive ester or aldehyde derivative of the polymer molecule) under conditions whereby the polypeptide comprising the amino acid sequence of SEQ ID NO: 4, or an Fhm polypeptide variant becomes attached to one or more polymer molecules, and (b) obtaining the reaction product(s). The optimal reaction conditions will be determined based on known parameters and the desired result. For example, the larger the ratio of polymer molecules:protein, the greater the percentage of attached polymer molecule. In one embodiment, the Fhm polypeptide derivative may have a single polymer molecule moiety at the amino terminus. (See, e.g., U.S. Pat. No. 5,234,784).

A particularly preferred water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol. PEG is a linear or branched neutral polyether, available in a broad range of molecular weights, and is soluble in water and most organic solvents. PEG is effective at excluding other polymers or peptides when present in water, primarily through its high dynamic chain mobility and hydrophobic nature, thus creating a water shell or hydration sphere when attached to other proteins or polymer surfaces. PEG is non-toxic, non-immunogenic, and approved by the Food and Drug Administration for internal consumption.

Proteins or enzymes when conjugated to PEG have demonstrated bioactivity, non-antigenic properties, and decreased clearance rates when administered in animals. F. M. Veronese et al., *Preparatioii and Properties of Monomethonpoly(ethylene glyco.)-modified Enzymes for Therapeutic Applications*, in J. M. Harris ed., Poly(Ethylene Clycol) Chemistry—Biotechnical and Biomedical Applications 127-36, 1992, incorporated herein by reference. This is due to the exclusion properties of PEG in preventing recognition by the immune system. In addition, PEG has been widely used in surface modification procedures to decrease protein adsorption and improve blood compatibility. S. W. Kim et al., *Ann. N.Y. Acad. Sci.* 516: 116-30 1987; Jacobs et al., Artif. Organs 12: 500-501, 1988; Park et al., *J. Poly. Sci, Part A* 29:1725-31, 1991, incorporated herein by reference. Hydrophobic polymer surfaces, such as polyurethanes and polystyrene were modified by the grafting of PEG (MW 3,400) and employed as non-thrombogenic surfaces. In these studies, surface properties (contact angle) were more consistent with hydrophilic surfaces, due to the hydrating effect of PEG. More importantly, protein (albumin and other plasma proteins) adsorption was greatly reduced, resulting from the high chain motility, hydration sphere, and protein exclusion properties of PEG.

PEG (MW 3,4000) was determined as an optimal size in surface immobilization studies, Park et al., *J. Biomed. Alat. Res.* 26:739-45, 1992, while PEG (MW 5,000) was most beneficial in decreasing protein antigenicity. (F. M. Veronese et al., In J. M. Harris et., *Poly(Ethylene Glycol) Chemistry—Biotechnical and Biomedical Applications* 127-36, supra., incorporated herein by reference)

In general, chemical derivatization may be performed under any suitable conditions used to react a biologically active substance with an activated polymer molecule. Methods for preparing pegylated Fhm polypeptides will generally comprise the steps of (a) reacting the polypeptide with polyethylene glycol (such as a reactive ester or aldehyde derivative of PEG) under conditions whereby Fhm polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

In a preferred embodiment, the Fhm polypeptide derivative will have a single PEG moiety at the N terminus. See U.S. Pat. No. 8,234,784, herein incorporated by reference.

Generally, conditions which may be alleviated or modulated by administration of the present Fhm polypeptide derivative include those described herein for Fhm polypeptides. However, the Fhm polypeptide derivative disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents, rabbits, goats, or sheep, or other farm animals, in which the gene (or genes) encoding the native Fhm polypeptide has (have) been disrupted ("knocked out") such that the level of expression of this gene or genes is(are) significantly decreased or completely abolished. Such animals may be prepared using techniques and methods such as those described in U.S. Pat. No. 5,557,032.

The present invention further includes non-human animals such as mice, rats, or other rodents, rabbits, goats, sheep, or other farm animals, in which either the native form of the Fhm gene(s) for that animal or a heterologous Fhm gene(s) is (are) over-expressed by the animal, thereby creating a "transgenic" animal. Such transgenic animals may be prepared using well-known methods such as those described in U.S. Pat. No. 5,489,743 and PCT application No. WO94/28122.Application No. WO 94/28122.

The present invention further includes non-human animals in which the promoter for one or more of the Fhm polypeptides of the present invention is either activated or inactivated (e.g., by using homologous recombination methods) to alter the level of expression of one or more of the native Fhm polypeptides.

These non-human animals may be used for drug candidate screening. In such screening, the impact of a drug candidate on the animal may be measured; for example, drug candidates may decrease or increase the expression of the Fhm gene. In certain embodiments, the amount of Fhm polypeptide, that is produced may be measured after the exposure of the animal to the drug candidate. Additionally, in certain embodiments, one may detect the actual impact of the drug candidate on the animal. For example, the overexpression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Microarray

It will be appreciated that DNA microarray technology can be utilized in accordance with the present invention. DNA microarrays are miniature, high density arrays of nucleic acids positioned on a solid support, such as glass. Each cell or element within the array has numerous copies of a single species of DNA which acts as a target for hybridization for its cognate mRNA. In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA which is specifically bound to each target DNA. In this way, the expression of thousands of genes can be quantitated in a high throughput, parallel manner from a single sample of biological material.

This high throughput expression profiling has a broad range of applications with respect to the Fhm molecules of the invention, including, but not limited to: the identification and validation of Fhm disease-related genes as targets for therapeutics; molecular toxicology of Fhm molecules and inhibitors thereof; stratification of populations and generation of surrogate markers for clinical trials; and enhancing Fhm-related small molecule drug discovery by aiding in the identification of selective compounds in high throughput screens (HTS).

Selective Binding Agents

As used herein, the term "selective binding agent" refers to a molecule which has specificity for one or more Fhm polypeptides. Suitable selective binding agents include, but are not limited to, antibodies and derivatives thereof, polypeptides, and small molecules. Suitable selective binding agents may be prepared using methods known in the art. An exemplary Fhm polypeptide selective binding agent of the present invention is capable of binding a certain portion of the Fhm polypeptide thereby inhibiting the binding of the polypeptide to the Fhm polypeptide receptor(s).

Selective binding agents such as antibodies and antibody fragments that bind Fhm polypeptides are within the scope of the present invention. The antibodies may be polyclonal including monospecific polyclonal, monoclonal (mAbs), recombinant, chimeric, humanized such as CDR-grafted, human, single chain, and/or bispecific, as well as fragments, variants or derivatives thereof. Antibody fragments include those portions of the antibody which bind to an epitope on the Fhm polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a Fhm polypeptide generally are produce in animals (e.g. rabbits or mice) by means of multiple subcutaneous or intraperitoneal injections of Fhm and an adjuvant. It may be useful to conjugate a Fhm polypeptide, or a variant, fragment or derivative thereof to a carrier protein that is immunogenic in the species to be immunized, such as keyhole limpet heocyanin, serum, albumin, bovine thyroglobulin, or soybean trypsin inhibitor. Also, aggregating agents such as alum are used to enhance the immune response. After immunization, the animals are bled and the serum is assayed for anti-Fhm antibody titer.

Monoclonal antibodies directed toward Fhm are produced using any method which provides for the production of antibody molecules by continuous cell lines in culture. Examples of suitable methods for preparing monoclonal antibodies include the hybridoma method of Kohler et al., *Nature* 256: 495-497, 1975, and the human B-cell hybridoma method, Kozbor, *J. Immunol.* 133: 3001, 1984; Brodeur et al., *Monoclonal Antibody Production Techniques and Applications*, pp. 51-63 (Marcel Dekker, Inc., New York, 1987).

Also provided by the invention are hybridoma cell lines which produce monoclonal antibodies reactive with Fhm polypeptides.

Monoclonal antibodies of the invention may be modified for use as therapeutics. One embodiment is a "chimeric" antibody in which a portion of the heavy and/or light chain is identical with or homologous to corresponding sequence in antibodies derived from a particular species or belonging to a particular antibody class or subclass, while the remainder of the chain(s) is/are identical with or a homologous to corresponding sequence in antibodies derived from another species or belonging to another antibody class or subclass. Also included are fragments of such antibodies, so long as they exhibit the desired biological activity (see U.S. Pat. No. 4,816,567; Morrison, et al., *Proc. Natl. Acad. Sci. U.S.A.* 81: 6851-6855, 1985; incorporated herein by reference).

In another embodiment, a monoclonal antibody of the invention is a "humanized" antibody. Methods for humanizing non-human antibodies are well known in the art (see U.S. Pat. Nos. 5,585,089 and 5,693,762). Generally, a humanized antibody has one or more amino acid residues introduced into it from a source which is non-human. Humanization can be performed, for example, methods described in the art (Jones et al., *Nature* 321: 522-525, 1986; Riechmann et al., *Nature*, 332: 323-327, 1988; Verhoeyen et al., *Science* 239: 1534-1536, 1988), by substituting at least a portion of a rodent complementarity-determining region (CDR) for the corresponding regions of a human antibody.

Also encompassed by the invention are fully human antibodies which bind Fhm polypeptides, fragments, variants and/or derivatives. Such antibodies are produced by immunization with a Fhm antigen optionally conjugated to a carrier (i.e., at least having 6 contiguous amino acids). Using transgenic animals (e.g., mice) that are capable of producing a repertoire of human antibodies in the absence of endogenous immunoglobulin production. See, for example, Jakobovits, et al., *Proc. Natl. Acad. Sci. U.S.A.* 90: 2551-2555, 1993; Jakobovits, et al., *Nature* 362: 255-258, 1993; Bruggermann, et al., *Year in Immuno.* 7:33, 1993. In one method, such transgenic animals are produced by incapacitating the endogenous loci encoding the heavy and light immunoglobulin chains therein, and inserting loci encoding human heavy and light chain proteins into the genome thereof. Partially modified animals, that is those having less than the full complement of modifications, are then cross-bred to obtain an animal having all of the desired immune system modifications. When administered an immunogen, these transgenic animals produce antibodies with human (rather than e.g., murine) amino acid sequences, including variable regions which are immunospecific for these antigens. See PCT Application Nos. PCT/US96/05928 and PCT/US93/06926. Additional methods are described in U.S. Pat. No. 5,545,807, PCT application nos. PCT/US91/245, PCT/GB89/01207, and in EP 546073B1 and EP 546073A1. Human antibodies may also be produced by the expression of recombinant DNA in host cells or by expression in hybridoma cells as described herein.

In an alternative embodiment, human antibodies can be produced in phage-display libraries (Hoogenboom, et al., *J. Mol. Biol.* 227:381, 1991; Marks. et al. *J. Mol. Biol.* 222:581, 1991. These processes mimic immune selection through the display of antibody repertoires on the surface of filamentous bacteriophage, and subsequent selection of phage by their binding to an antigen of choice. One such technique is described in PCT Application No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-Fhm antibodies of the invention may be employed in any known assay method, such as competitive binding assays, direct and indirect sandwich assays, and immunoprecipitation assays (Sola, *Monoclonal Anitibodies: A Manual of Techniques*, pp. 147-158 (CRC Press, Inc., 1987)) for the detection and quantitation of Fhm polypeptides. The antibodies will bind Fhm polypeptides with an affinity which is appropriate for the assay method being employed.

For diagnostic applications, in certain embodiments anti-Fhm antibodies typically may be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase, or horseradish peroxidase. See Bayer, et al., *Meth. Enz.* 184: 138-163, 1990.

The anti-Fhm antibodies of the invention may be employed in any known assay method, such as competitive binding assays, direct and indirect sandwich assays, and immunoprecipitation assays (Sola, *Monoclonal Antibodies: A Manaul of Techniques*, pp. 147-158 (CRC Press, Inc., 1987)) for detection and quantitation of Fhm polypeptides. The antibodies will bind Fhm polypeptides with an affinity which is appropriate for the assay method being employed.

The activity of the cell lysate or purified Fhm protein variant is then screened in a suitable screening assay for the desired characteristic. For example, a change in the binding affinity for a ligand or immunological character of the Fhm protein, such as affinity for a given antibody, is measured by a competitive type immunoassay. Changes in immunomodulation activity are measured by the appropriate assay. Modifications of such protein properties as redox or thermal stability hydrophobicity, susceptibility to proteolytic degradation or the tendency to aggregate with carriers or into multimers are assayed by methods well known to the ordinarily skilled artisan. Competitive binding assays rely on the ability of a labeled standard (e.g., a Fhm polypeptide, or an immunologically reactive portion thereof) to compete with the test sample analyte (a Fhm polypeptide) for binding with a limited amount of antibody. The amount of a Fhm polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich immuno-assays typically involve the use of two antibodies, each capable of binding to a different immunogenic portion, or epitope, of the protein to be detected and/or quantitated. In a sandwich assay, the test sample analyte typically is bound by a first antibody which is immobilized on a solid support, and thereafter a second antibody binds to the analyte, thus forming an insoluble three-part complex. See e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme linked immunosorbant assay (ELISA), in which case the detectable moiety is an enzyme.

The selective binding agents, including anti-Fhm antibodies, are also useful for in vivo imaging. An antibody labeled with a detectable moiety may be administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

Selective binding agents, including antibodies of the invention, may be used as therapeutics. These therapeutic antibodies are generally agonists or antagonists, in that they either enhance or reduce, respectively, at least one of the biological activities of a Fhm polypeptide. In one embodiment, antagonist antibodies of the invention are antibodies or binding fragments thereof which are capable of specifically binding to a Fhm polypeptide, fragment, variant and/or derivative, and which are capable of inhibiting or eliminating the functional activity of a Fhm polypeptide in vivo or in vitro. In preferred embodiments, an antagonist antibody will inhibit the functional activity of a Fhm polypeptide at least about 50%, preferably at least about 80%, more preferably 90%, and most preferably 100%. In another embodiment, the selective binding agent may be an antibody that is capable of interacting with an Fhm binding partner (e.g., receptor) thereby inhibiting or eliminating Fhm activity in vitro or in vivo. Selective binding agents, including agonist and antagonist anti-Fhm antibodies, are identified by screening assays which are well known in the art.

The invention also relates to a kit comprising Fhm selective binding agents (such as antibodies) and other reagents useful for detecting Fhm polypeptide levels in biological samples. Such reagents may include, a detectable label, blocking serum, positive and negative control samples, and detection reagents.

The Fhm polypeptides of the present invention can be used to clone Fhm receptors, using an expression cloning strategy. Radiolabeled ($^{125}$Iodine) Fhm polypeptide or affinity/activity-tagged Fhm polypeptide (such as an Fc fusion or an alkaline phosphatase fusion) can be used in binding assays to identify a cell type or cell line or tissue that expresses Fhm receptor(s). RNA isolated from such cells or tissues can be converted to cDNA, cloned into a mammalian expression vector, and transfected into mammalian cells (such as COS or 293 cells) to create an expression library. A radiolabeled or tagged Fhm polypeptide can then be used as an affinity ligand to identify and isolate from this library the subset of cells which express the Fhm receptor(s) on their surface. DNA can then be isolated from these cells and transfected into mammalian cells to create a secondary expression library in which the fraction of cells expressing Fhm receptor(s) is many-fold higher than in the original library. This enrichment process can be repeated iteratively until a single recombinant clone containing an Fhm receptor is isolated. Isolation of the Fhm receptor(s) is useful for identifying or developing novel agonists and antagonists of the Fhm polypeptide signaling pathway. Such agonists and antagonists include soluble Fhm receptor(s), anti-Fhm receptor antibodies, small molecules, or antisense oligonucleotides, and they may be used for treating, preventing, or diagnosing one or more disease or disorder, including those described herein.

Diagnostic Kits and Reagents

This invention also contemplates use of Fhm proteins, fragments thereof, peptides, binding compositions, and their fusion products in a variety of diagnostic kits and methods for detecting the presence of receptors and/or antibodies. Typically the kit will have a compartment containing a Fhm peptide or gene segment or a reagent which recognizes one or the other, e.g., binding reagents.

A kit for determining the binding affinity of a binding partner or a test compound to the Fhm would typically comprise a binding partner test compound; a labeled compound, for example an antibody having known binding affinity for the protein; or a source of binding partner (naturally occurring or recombinant), and a means for separating bound from free labeled compound, such as a solid phase for immobilizing the ligand or its binding partner. Once compounds are screened, those having suitable binding affinity to the ligand or its binding partner can be evaluated in suitable biological assays, as are well known in the art, to determine whether they act as agonists or antagonists of Fhm activity. The availability of recombinant Fhm and/or receptor polypeptides also provide well defined standards for calibrating such assays or as positive control samples.

A preferred kit for determining the concentration of, for example. Fhm-ligand and/or its cognate binding partner in a sample would typically comprise a labeled compound, e.g., antibody, having known binding affinity for the target, a source of ligand or receptor (naturally occurring or recombinant), and a means for separating the bound from free labeled compound, for example, a solid phase for immobilizing the ligand or receptor. Compartments containing reagents, and instructions for use or disposal, will normally be provided.

Antibodies, including antigen binding fragments, specific for the ligand or receptor, or fragments are useful in diagnostic applications to detect the presence of elevated levels of ligand, receptor, and/or its fragments. Such diagnostic assays can employ lysates, live cells, fixed cells, immunofluorescence, cell cultures, body fluids, and further can involve the detection of antigens related to the ligand or receptor in serum, or the like. Diagnostic assays may be homogeneous (without a separation step between free reagent and antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, unlabeled antibodies can be employed by using a second antibody which is labeled and which recognizes the primary antibody to a ligand or receptor or to a particular fragment thereof. Similar assays have also been extensively discussed in the literature. (See, e.g., Harlow and Lane (1988) *Antibodies: A Laboratory Manual*, Cold Spring Harbor Laboratory Press.)

Anti-idiotypic antibodies may have similar uses to diagnose presence of antibodies against a ligand or receptor, as such may be diagnostic of various abnormal states. For example, overproduction of a ligand or receptor may result in production of various immunological reactions which may be diagnostic of abnormal physiological states, particularly in various inflammatory or allergic conditions.

Frequently, the reagents for diagnostic assays are supplied in kits, so as to optimize the sensitivity of the assay. For the subject invention, depending upon the nature of the assay, the protocol, and the label, either labeled or unlabeled antibody or labeled ligand or receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments or containers for each useful reagent. Desirably, the reagents are provided as a dry lyophilized powder, where the reagents may be reconstituted in an aqueous medium providing appropriate concentrations of reagents for performing the assay.

The aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, receptor, or antibodies thereto can be labeled either directly or indirectly. Possibilities for direct labeling include label groups: radio labels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating bound from the free ligand, or alternatively bound from free test compound. The ligand or receptor can be immobilized on various matrixes, perhaps with detergents or associated lipids, followed by washing. Suitable matrixes include plastic such as an ELISA plate, filters, and beads. Methods of immobilizing the ligand or receptor to a matrix include, without limitation, direct adhesion to plastic, use of a capture antibody, chemical coupling, and biotin-avidin. The last step in this approach may involve the precipitation of antigen/antibody complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle et al. *Clin. Chem.*, 30:1457-1461, 1984, and the double antibody magnetic particle separation as described in U.S. Pat. No. 4,659,6178, incorporated herein by reference.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Nucleic acid molecules of the invention may be used to map the locations of the Fhm gene and related genes on chromosomes. Mapping may be done by techniques known in the art, such as PCR amplification, in situ hybridization, and FISH.

This invention is also related to the use of the Fhm gene as part of a diagnostic assay for detecting diseases or susceptibility to diseases related to the presence of mutated Fhm gene. Such diseases are related to an abnormal expression of Fhm, for example, abnormal cellular proliferation such as tumors and cancers.

Individuals carrying mutations in the human Fhm gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., *Nature*, 324:163-166, 1986) prior to analysis. RNA or cDNA may also be used for the same purpose. As an example, PCR primers complementary to the nucleic acid encoding Fhm polypeptide can be used to identify and analyze Fhm mutations. For example, deletions and insertions can be detected by a change in size of the amplified product in comparison to the normal genotype. Point mutations can be identified by hybridizing amplified DNA to radiolabeled Fhm RNA or alternatively radiolabeled Fhm antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing, formamide gradient gels in which the mobilities of different DNA fragments are retarded in the gel at different positions according to their specific melting or partial melting temperatures (see, e.g., Myers et al., *Science*, 230:1242, 1985).

Sequence changes at specific locations may also be revealed by nuclease protection assays, such as RNase and S1 protection or the chemical cleavage method (e.g., Cotton et al., Proc. Natl. Acad. Sci., USA, 85:4397-4401, 1985).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The present invention also relates to a diagnostic assay for detecting altered levels of Fhm protein in various tissues since an over-expression of the proteins compared to normal control tissue samples may detect the presence of a disease or susceptibility to a disease, for example, tumors, cerebral malaria and hereditary periodic fever syndromes. Assays used to detect levels of Fhm protein in a sample derived from a host are well-known to those of skill in the art and include radioimmunoassays, competitive-binding assays, Western Blot analysis, ELISA assays and "sandwich" assay. An ELISA assay (Coligan, et al., Current Protocols in Immunology, 1(2), Chapter 6, 1991) partially comprises preparing an antibody specific to the Fhm antigen, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g., a polystyrene dish, that binds the proteins in the sample. Any free protein binding sites on the dish are then covered by incubating with a non-specific protein like bovine serum albumin (BSA). Next, the monoclonal antibody is incubated in the dish during which time the monoclonal antibodies attach to any Fhm proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to Fhm. Unattached reporter antibody is then washed out. Peroxidase substrates are then added to the dish and the amount of color developed in a given time period is a measurement of the amount of Fhm protein present in a given volume of patient sample when compared against a standard curve.

A competition assay may be employed wherein antibodies specific to Fhm are attached to a solid support and labeled Fhm and a sample derived from the host are passed over the solid support and the amount of label detected, for example, by liquid scintillation chromotagraphy, can be correlated to a quantity of Fhm in the sample. In addition, a sandwich immuno-assay as described above may also be carried out to quantify the amount of Fhm in a biological sample.

The sequences of the present invention are also valuable for chromosome identification and mapping. The sequence can be specifically targeted to and can hybridize with a particular location on an individual human chromosome. Moreover, there is a current need for identifying particular sites on the chromosome wherein a gene can be localized. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15-25 bp) from the cDNA. Computer analysis of the 3'-untranslated region of the sequence is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map Fhm to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 500 or 600 bases; however, clones larger than 2,000 bp have a higher likelihood of binding to a unique chromosomal location with sufficient signal intensity for simple detection. FISH requires use of genomic clones or clones from which the express sequence tag (EST) was derived, and the longer the better. For example, 2,000 bp is good, 4,000 is better, and more than 4,000 is probably not necessary to get good results a reasonable percentage of the time. For a review of this technique see Verma et al., Human Chromosomes: A Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The nucleic acid molecule(s) of the present invention are also useful as anti-sense inhibitors of Fhm expression. Such inhibition may be effected by nucleic acid molecules which are complementary to and hybridize to expression control sequences (triple helix formation) or to Fhm mRNA. Anti-sense probes may be designed by available techniques using the sequence of Fhm disclosed herein. Anti-sense inhibitors provide information relating to the decrease or absence of a Fhm polypeptide in a cell or organism.

The nucleic acid molecules of the invention may be used for gene therapy. Nucleic acid molecules which express Fhm in vivo provide information relating to the effects of the polypeptide in cells or organisms. Fhm nucleic acid molecules, fragments, and/or derivatives that do not themselves encode biologically active polypeptides may be useful as hybridization probes in diagnostic assays to test, either qualitatively or quantitatively, for the presence of Fhm DNA or corresponding RNA in mammalian tissue or bodily fluid samples.

Fhm polypeptide fragments, variants, and/or derivatives, whether biologically active or not, are useful for preparing antibodies that bind to an Fhm polypeptide. The antibodies may be used for in vivo and in vitro diagnostic purposes, such as in labeled form to detect the presence of Fhm polypeptide in a body fluid or cell sample. The antibodies may bind to an Fhm polypeptide so as to diminish or block at least one activity characteristic of an Fhm polypeptide, or may bind to a polypeptide to increase an activity.

Assaying for Modulators of Fhm Polypeptide Activity:

In some situations, it may be desirable to identify molecules that are modulators, i.e., agonists or antagonists, of the activity of Fhm polypeptide. Natural or synthetic molecules that modulate Fhm polypeptide can be identified using one or more of the screening assays, such as those described herein. Such molecules may be administered either in an ex vivo manner, or in an in vivo manner by local or intravenous (iv) injection, or by oral delivery, implantation device, or the like.

"Test molecule(s)" refers to the molecule(s) that is/are under evaluation for the ability to modulate (i.e., increase or decrease) the activity of an Fhm polypeptide. Most commonly, a test molecule will interact directly with an Fhm polypeptide. However, it is also contemplated that a test molecule may also modulate Fhm polypeptide activity indirectly, such as by affecting Fhm gene expression, or by binding to an Fhm binding partner (e.g., receptor). In one embodiment, a test molecule will bind to an Fhm polypeptide with an affinity constant of at least about $10^{-6}$ M, preferably about $10^{-8}$ M, more preferably about $10^{-9}$ M, and even more preferably about $10^{-10}$ M.

Methods for identifying compounds which interact with Fhm receptor polypeptides are encompassed by the invention. In certain embodiments, a Fhm receptor polypeptide is incubated with a test molecule under conditions which permit interaction of the test molecule to the receptor polypeptide, in the presence or absence of bioactive Fhm, and the extent of the interaction can be measured. The test molecules can be screened in a substantially purified form or in a crude mixture.

In certain embodiments, a Fhm polypeptide agonist or antagonist may be a protein, peptide, carbohydrate, lipid, or small molecular weight molecule which interacts with Fhm polypeptide to regulate its activity. Molecules which regulate Fhm polypeptide expression include nucleic acids which are complementary to nucleic acids encoding an Fhm polypeptide, or are complementary to nucleic acids acid sequences which direct or control the expression of Fhm polypeptide, and which act as anti-sense regulators of expression.

The measurement of the interaction of test molecules with putative Fhm receptor polypeptide(s) in the presence or absence of Fhm ligand may be carried out in several formats, including cell-based binding assays, membrane binding assays, solution-phase assays and immunoassays. In general, test molecules are incubated with a putative Fhm receptor polypeptide for a specified period of time and Fhm polypeptide activity is determined by one or more assays measuring biological activity.

The interaction of test molecules with Fhm polypeptides may also be assayed directly using polyclonal or monoclonal antibodies in an immunoassay. Alternatively, modified forms of Fhm polypeptides containing epitope tags as described herein may be used in immunoassays.

Homogeneous assay technologies for radioactivity (SPA; Amersham) and time resolved fluorescence (HTRF, Packard) can also be implemented. Binding can be detected by labeling with radioactive isotopes ($^{125}$I, $^{35}$S, $^{3}$H), fluorescent dyes (fluorescein), lanthanides such as Europeum (Eu$^{3+}$) chelates or cryptates, orbipyridyl-ruthenium (Ru$^{2-}$) complexes. It is understood that the choice of a labeled probe will depend upon the detection system used. Alternatively, Fhm or putative Fhm agonists or antagonists may be modified with an unlabeled epitope tag (e.g., biotin, peptides, His6, myc, Fc) and bound to proteins such as streptavidin, anti-peptide or anti-protein antibodies which have a detectable label as described above.

Binding of test molecules to putative Fhm receptor polypeptides may also be assayed directly using polyclonal or monoclonal antibodies in an immunoassay. Alternatively, modified forms of putative Fhm-receptor polypeptide(s) containing epitope tags as described above may be used in solution and immunoassays.

In one embodiment, modulators of the Fhm-ligand may be a protein, peptide, carbohydrate, lipid or small molecular weight molecule. Potential protein antagonists of Fhm include antibodies which bind to active regions of the polypeptide and inhibit or eliminate binding of Fhm to its putative receptor. Molecules which regulate Fhm polypeptide expression may include nucleic acids which are complementary to nucleic acids encoding a Fhm polypeptide, or are complementary to nucleic acids sequences which direct or control expression of polypeptide, and which act as anti-sense regulators of expression.

In the event that Fhm polypeptides display biological activity through an interaction with a binding partner (e.g., a receptor), a variety of in vitro assays may be used to measure binding of Fhm polypeptide to a corresponding binding partner (such as a selective binding agent or lignad). These assays may be used to screen test molecules for their ability to increase or decrease the rate and/or the extent of binding of a Fhm polypeptide to its binding partner. In one assay, Fhm polypeptide is immobilized in the wells of a microtiter plate. Radiolabeled Fhm binding partner (for example, iodinated Fhm binding partner) and the test molecule(s) can then be added either one at a time (in either order) or simultaneously to the wells. After incubation, the wells can be washed and counted (using a scintillation counter) for radioactivity to determine the extent of binding to which the binding partner bound to Fhm polypeptide. Typically, the molecules will be tested over a range of concentrations, and a series of control wells lacking one or more elements of the test assays can be used for accuracy in the evaluation of the results. An alternative to this method involves reversing the "positions" of the proteins. i.e., immobilizing Fhm binding partner to the microtiter plate wells, incubating with the test molecule and radiolabeled Fhm and determining the extent of Fhm binding (see, for example, Chapter 18 of *Current Protocols in Molecular Biology*, Ausubel et al., eds., John Wiley & Sons, New York, N.Y., 1995).

As an alternative to radiolabeling, a Fhm polypeptide or its binding partner may be conjugated to biotin and the presence of biotinylated protein can then be detected using streptavidin linked to an enzyme, such as horseradish peroxidase (HRP) or alkaline phosphatase (AP), that can be detected colorometrically, or by fluorescent tagging of streptavidin. An antibody directed to an Fhm polypeptide or to an Fhm binding partner and is conjugated to biotin may also be used and can be detected after incubation with enzyme-linked streptavidin linked to AP or HRP A Fhm polypeptide and a Fhm binding partner can also be immobilized by attachment to agarose beads, acrylic beads or other types of such inert solid phase substrates. The substrate-protein complex can be placed in a solution containing the complementary protein and the test compound. After incubation, the beads can be precipitated by centrifugation, and the amount of binding between an Fhm polypeptide and its binding partner can be assessed using the methods described above. Alternatively, the substrate-protein complex can be immobilized in a column and the test molecule and complementary protein passed over the column. Formation of a complex between an Fhm polypeptide and its binding partner can then be assessed using any of the techniques described herein, i.e., radiolabeling, antibody binding, or the like.

Another in vitro assay that is useful for identifying a test molecule which increases or decreases the formation of a complex between a Fhm binding protein and a Fhm binding partner is a surface plasmon resonance detector system such as the BIAcore assay system (Pharmacia, Piscataway, N.J.). The BIAcore system may be carried out using the manufacturer's protocol. This assay essentially involves the covalent binding of either Fhm or a Fhm binding partner to a dextran-coated sensor chip which is located in a detector. The test compound and the other complementary protein can then be injected either simultaneously or sequentially into the chamber containing the sensor chip. The amount of complementary protein binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease the formation of a complex between a Fhm polypeptide and a Fhm binding partner complex. In these cases, the assays described herein can be readily modified by adding such additional test compound(s) either simultaneous with, or subsequent to, the first test compound. The remainder of the steps in the assay are as set forth herein.

In vitro assays such as those described herein may be used advantageously to screen rapidly large numbers of compounds for effects on complex formation by Fhm and Fhm binding partner. The assays may be automated to screen compounds generated in phage display, synthetic peptide and chemical synthesis libraries.

Compounds which increase or decrease the formation of a complex between a Fhm polypeptide and a Fhm binding partner may also be screened in cell culture using cells and cell lines expressing either Fhm or Fhm binding partner. Cells and cell lines may be obtained from any mammal, but preferably will be from human or other primate, canine, or rodent sources. The binding of an Fhm polypeptide to cells expressing Fhm binding partner at the surface is evaluated in the presence or absence of test molecules and the extent of binding may be determined by, for example, flow cytometry using a biotinylated antibody to an Fhm binding partner. Cell culture assays may be used advantageously to further evaluate compounds that score positive in protein binding assays described herein.

Cell cultures can also be used to screen the impact of a drug candidate. For example, drug candidates may decrease or increase the expression of the Fhm gene. In certain embodiments, the amount of Fhm polypeptide that is produced may be measured after exposure of the cell culture to the drug candidate. In certain embodiments, one may detect the actual impact of the drug candidate on the cell culture. For example, the overexpression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

P38 Inhibitors

A new approach to intervention between the extracellular stimulus and the secretion of IL-1 and TNFα from the cell involves blocking signal transduction through inhibition of a kinase which lies on the signal pathway. One example is through inhibition of P-38 (also called "RK" or "SAPK-2", Lee et al., Nature, 372:739, 1994), a known ser/thr kinase (clone reported in Han et al., Biochimica Biophysica Acta, 1265:224-227, 1995). A linear relationship has been shown for effectiveness in a competitive binding assay to P-38, and the same inhibitor diminishing the levels of IL-1 secretion from monocytes following LPS stimulation. Following LPS stimulation of monocytes, the levels of messenger RNA for TNF-α have been shown to increase 100 fold, but the protein levels of TNF-α are increased 10,000 fold. Thus, a considerable amplification of the TNF signaling occurs at the translational level. Following LPS stimulation of monocytes in the presence of a P-38 inhibitor, the levels of mRNA are not affected, but the levels of final TNF protein are dramatically reduced (up to 80-90% depending on the effectiveness of the P-38 inhibitor). Thus, the above experiments lend strong support to the conclusion that inhibition of P-38 leads to diminished translational efficiency. Further evidence that TNFa is under translational control is found in the deletion experiments of Beutler et al. and Lee, wherein segments of 3' untranslated mRNA (3' UTR) are removed resulting in high translational efficiency for TNFα. More importantly, the P-38 inhibitors did not have an effect on the level of TNFα (i.e., translational efficiency) when the appropriate segments of TNFα mRNA are deleted. Thus, the correlative data between the level of binding of inhibitors to P-38 and the diminished IL-1 and TNFα levels following LPS stimulation with the same inhibitors, plus the above biochemical evidence regarding the effect of P-38 inhibitors on translational efficiency of both TNFα and IL-1 make a strong cause and effect relationship. The role of P-38 in the cell is still being delineated; so therefore, other beneficial effects regarding inflammatory diseases or other disease states obtained from its inhibition maybe forthcoming.

Elevated levels of TNFα and/or IL-1 may contribute to the onset, etiology, or exacerbate a number of disease states, including, but not limited to: rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; antiviral therapy including those viruses sensitive to TNFα: inhibition —HIV-1, HIV-2, HIV-3, cytomegalovirus (CMV), influenza, adenovirus, and the herpes viruses including HSV-1, HSV-2, and herpes zoster; muscle degeneration; cachexia; Reiter's syndrome; type II diabetes; bone resorption diseases; graft vs. host reaction; ischemia reperfusion injury; atherosclerosis; brain trauma; Alzheimer's disease; multiple sclerosis; cerebral malaria; sepsis; septic shock; toxic shock syndrome; fever and mylagias due to infection.

Substituted imidazole, pyrrole, pyridine, pyrimidine and the like compounds have been described for use in the treatment of cytokine mediated diseases by inhibition of proinflammatory cytokines, such as IL-1, IL-6, IL-8 and TNF. Substituted imidazoles for use in the treatment of cytokine mediated diseases have been described in U.S. Pat. No. 5,593, 992; WO 93/14081; WO 97/18626; WO 96/21452; WO 96/21654; WO 96/40143; WO 97/05878; WO 97/05878; (each of which is incorporated herein by reference in its entirety). Substituted imidazoles for use in the treatment of inflammation has been described in U.S. Pat. No. 3,929,807 (which is incorporated herein by reference in its entirety). Substituted pyrrole compounds for use in the treatment of cytokine mediated diseases have been described in WO 97/05877; WO 97/05878; WO 97/16426; WO 97/16441; and WO 97/16442 (each of which is incorporated herein by reference in its entirety). Substituted aryl and heteroaryl fused pyrrole compounds for use in the treatment of cytokine mediated diseases have been described in WO 98/22457 (which is incorporated herein by reference in its entirety). Substituted pyridine, pyrimidine, pyrimidinone and pyridazine compounds for use in the treatment of cytokine mediated diseases have been described in WO 98/24780; WO 98/24782; WO 99/24404; and WO 99/32448 (each of which is incorporated herein by reference in its entirety).

Internalizing Proteins

The TAT protein sequence (from HIV) can be used to internalize proteins into a cell by targeting the lipid bi-layer component of the cell membrane. See e.g., Falwell et al., *Proc. Natl. Acad. Sci.*, 91: 664-668, 1994. For example, an 11 amino acid sequence (YGRKKRRQRRR; SEQ ID NO: 22) of the HIV TAT protein (termed the "protein transduction domain", or TAT PDT) has been shown to mediate delivery of large bioactive proteins such as β-galactosidase and p27Kip across the cytoplasmic membrane and the nuclear membrane of a cell. See Schwarze et al., *Science,* 285: 1569-1572, 1999; and Nagahara et al., *Nature Medicine,* 4: 1449-1452, 1998. Schwartze et al. (*Science,* 285: 1569-72, 1999) demonstrated that cultured cells acquired β-gal activity when exposed to a fusion of the TAT PDT and β-galactosidase. Injection of mice with the TAT-β-gal fusion proteins resulted in β-gal expression in a number of tissues, including liver, kidney, lung, heart, and brain tissue.

It will thus be appreciated that the TAT protein sequence may be used to internalize a desired protein or polypeptide into a cell. In the context of the present invention, the TAT protein sequence can be fused to another molecule such as a Fhm antagonist (i.e.: anti-Fhm selective binding agent or small molecule) and administered intracellularly to inhibit the activity of the Fhm molecule. Where desired, the Fhm protein itself, or a peptide fragment or modified form of Fhm, may be fused to such a protein transducer for administrating to cells using the procedures, described above.

Therapeutic Uses

Members of the TNF ligand family have been implicated in mediation of a number of diseases. The pleiotropic nature of TNF and related ligand family members prevents generalization about whether a particular polypeptide is beneficial or injurious. It is clear that in some instances, the local effects of TNF and other members of the TNF-ligand family of cytokines improve host defense mechanisms by mobilizing substrate, increasing immune cell function, stimulating inflammation, and in killing cancer cells. However, in other cases the toxicity of TNF and related cytokines may cause disease by mediating shock, tissue injury, or catabolic injury. There are many diseases wherein injury that is mediated by members of the TNF ligand family may be treated or ameliorated by the administration of soluble forms of members of the TNF-receptor gene family or TNF-like ligand molecules. These diseases include acquired-immunodeficiency syndrome (AIDS), anemia, autoimmune diseases, cachexia, cancer, cerebral malaria, diabetes mellitus, disseminated intravascular coagulopathy, erythryoid sick syndrome, hemorrhagic shock, hepatitis, insulin resistance, leprosy, leukemia, lymphoma, meningitis, multiple sclerosis, myocardial ischaemia, obesity, rejection of transplanted organs, rheumatoid arthritis, septic shock syndrome, stroke, adult respiratory distress syndrome (ARDS), tuberculosis, and a number of viral diseases.

Fhm Compositions and Administration

Pharmaceutical compositions of Fhm polypeptides are within the scope of the present invention for prophylactic and therapeutic treatment of humans and animals for indications resulting from abnormal expression of Fhm or where it is determined that administration of Fhm polypeptide will result in the amelioration or cure of the indications. Such compositions may comprise a therapeutically effective amount of a Fhm polypeptide and/or its binding partner, or therapeutically active fragment(s), variant(s), or derivative(s) thereof in admixture with a pharmaceutically acceptable additives and/or carriers. Suitable formulation materials or pharmaceutically acceptable agents include, but are not limited to, antioxidants, preservatives, colors, flavoring, and diluting agents, emulsifying agents, suspending agents, solvents, fillers, bulking agents, buffers, delivery vehicles, diluents, excipients, and/or pharmaceutical adjuvants. Typically, a therapeutic compound containing Fhm polypeptide(s) will be administered in the form of a composition comprising purified polypeptide, fragment(s), variant(s), or derivative(s) in conjunction with one or more physiologically acceptable carriers, excipients, or diluents. For example, a suitable vehicle may be water for injection, physiological solution, or artificial cerebrospinal fluid possibly supplemented with other materials common in compositions for parenteral delivery.

Neutral buffered saline or saline mixed with serum albumin are exemplary appropriate carriers. Preferably, the product is formulated as a lyophilizate using appropriate excipients (e.g., sucrose). Other standard carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor. The pH of the solution should also be selected based on the relative solubility of Fhm at various pHs.

The primary solvent in a composition may be either aqueous or non-aqueous in nature. In addition, the vehicle may contain other formulation materials for modifying or maintaining the pH, osmolarity, viscosity, clarity, color, sterility, stability, isotonicity, rate of dissolution, or odor of the formulation. Similarly, the composition may contain additional formulation materials for modifying or maintaining the rate of release of Fhm protein, or for promoting the absorption or penetration of Fhm protein.

Compositions comprising the Fhm polypeptide compositions can be administered parentally. Alternatively, the compositions may be administered intravenously or subcutaneously. When systemically administered, the therapeutic compositions for use in this invention may be in the form of a pyrogen-free, parentally acceptable aqueous solution. The preparation of such pharmaceutically acceptable protein solutions, with due regard to pH, isotonicity, stability and the like, is within the skill of the art.

Therapeutic formulations of Fhm polypeptide compositions useful for practicing the present invention may be prepared for storage by mixing the selected composition having the desired degree of purity with optional physiologically acceptable carriers, excipients, or stabilizers (*Remington's Pharmaceutical Sciences,* 18th Edition, A. R. Gennaro, ed., Mack Publishing Company, 1990) in the form of a lyophilized cake or an aqueous solution.

Acceptable carriers, excipients or stabilizers are nontoxic to recipients and are preferably inert at the dosages and concentrations employed, and include buffers such as phosphate, citrate, or other organic acids; antioxidants such as ascorbic acid; low molecular weight polypeptides; proteins, such as serum, albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

An effective amount of the Fhm polypeptide(s) composition to be employed therapeutically will depend, for example, upon the therapeutic objectives such as the indication for which the composition is being used, the route of administration (e.g., whether it is administered locally or systemically), and the condition of the patient (e.g., patient's general health, anaureuesis, age, weight, sex). It is essential, when determining the therapeutically effective dose, to take into account the quantity of Fhm or other members of the TNF family that are responsible for the disease. Basically, it can be assumed that for effective treatment of a disease triggered by the over expression of cytokine(s) such as Fhm, at least the same molar amount of the Fhm polypeptide(s) is required, and possibly a multiple excess might be needed, although less may be needed depending on the nature of the receptor and the nature of its interaction with Fhm. Accordingly, it will be necessary for the therapist to titer the dosage and/or in vivo modify the route of administration as required to obtain the optimal therapeutic effect. A typical daily dosage may range from about 0.1 mg/kg to up to 100 mg/kg or more, depending on the factors mentioned above. Typically, a clinician will administer the composition until a dosage is reached that achieves the desired effect. The composition may therefore be administered as a single dose, or as two or more doses (which may or may not contain the same amount of Fhm polypeptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The Fhm polypeptide composition to be used for in vivo administration must be sterile. This is readily accomplished by filtration through sterile filtration membranes. Where the composition is lyophilized, sterilization using thes method may be conducted either prior to or following lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle. Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

Effective administration forms, such as (1) slow-release formulations, (2) inhalant mists, or (3) orally active formulations are also envisioned. Pharmaceutical compositions comprising therapeutically effective dose of the Fhm polypeptide also may be formulated for parenteral administration. Such parenterally administered therapeutic compositions are typically in the form of a pyrogen-free, parenterally acceptable aqueous solution comprising Fhm in a pharmaceutically acceptable vehicle. The Fhm pharmaceutical compositions also may include particulate preparations of polymeric compounds such as polylactic acid, polyglycolic acid, etc. or the introduction of Fhm into liposomes. Hyaluronic acid may also be used, and this may have the effect of promoting sustained duration in the circulation.

A particularly suitable vehicle for parenteral injection is sterile distilled water in which Fhm is formulated as a sterile, isotonic solution, properly preserved. Yet another preparation may involve the formulation of Fhm with an agent, such as injectable microspheres, bio-erodible particles or beads, or liposomes, that provides for the controlled or sustained release of the protein product which may then be delivered as a depot injection. Other suitable means for the introduction of Fhm include implantable drug delivery devices which contain the Fhm and/or its binding partner.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol and polyethylene glycol. Suitable complexing agents are for example caffeine, polyvinylpyrrolidone, beta-cyclodextrin or hydroxypropyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as borate, citrate, phosphate, bicarbonate, or Tris-HCl.

The formulation components are present in concentration that are acceptable to the site of administration. For example, buffers are used to maintain the composition at physiological pH or at slightly lower pH, typically within a pH range of from about 5 to about 8.

When parenteral administration is contemplated, the therapeutic compositions for use in this invention may be in the form of a pyrogen-free, parenterally acceptable aqueous solution comprising the desired Fhm molecule in a pharmaceutically acceptable vehicle. A particularly suitable vehicle for parenteral injection is sterile distilled water in which an Fhm molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), or beads or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

A pharmaceutical composition may be formulated for inhalation. For example, Fhm may be formulated as a dry powder for inhalation. Fhm polypeptides or Fhm nucleic acid molecule inhalation solutions may also be formulated with a d propellant for aerosol delivery. In yet another embodiment, solutions may be nebulized. Pulmonary administration is further described in PCT Application No. PCT/US94/01875, which describes pulmonary delivery of chemically modified proteins.

It is also contemplated that certain formulations containing Fhm polypeptide(s) may be administered orally. In one embodiment, the Fhm ligand which is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the Fhm polypeptide. Diluents, flavorings, low melting point waxes, vegetable oils, lubricants, suspending agents, tablet disintegrating agents, and binders may also be employed.

Another pharmaceutical composition may involve an effective quantity of Fhm polypeptide in a mixture with non-toxic excipients which are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional Fhm-polypeptide pharmaceutical compositions will be evident to those skilled in the art, including formulations involving Fhm-polypeptide in sustained or controlled delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829 which describes the controlled release porous polymeric microparticles for the delivery of pharmaceutical compositions. Additional examples include semipermeable polymer matrices in the form of shaped articles e.g., films or microspheres.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of an Fhm pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the Fhm molecule is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

The frequency of dosing will depend upon the pharmacokinetic parameters of the Fhm molecule in the formulation used. Typically, a clinician will administer the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes, orroutes; by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

One may further administer the present pharmaceutical compositions by pulmonary administration, see, e.g., International Publication No: WO 94/20069, which discloses pulmonary delivery of chemically modified proteins, herein incorporated by reference. For pulmonary delivery, the particle size should be suitable for delivery to the distal lung. For example, the particle size may be from 1 mm to 5 mm, however, larger particles may be used, for example, if each particle is fairly porous. Alternatively or additionally, the composition may be administered locally via implantation into the affected area of a membrane, sponge, or other appropriate material on to which receptor polypeptide has been absorbed or encapsulated. Where an implantation device is used, the device may be implanted into any suitable tissue or organ, and delivery may be directly through the device via bolus, or via continuous administration, or via catheter using continuous infusion.

Fhm-ligand polypeptide(s) and/or its binding partner may also be administered in a sustained release formulation or preparation. Suitable polymer compositions preferably have intrinsic and controllable biodegradability so that they persist for about a week to about six months; are non-toxic containing no significant toxic monomers and degrading into non-toxic components; are biocompatible, are chemically compatible with substances to be delivered, and tend not to denature the active substance; are sufficiently porous to allow the incorporation of biologically active molecules and their subsequent liberation from the polymer by diffusion, erosion or a combination thereof; are able to remain at the site of the application by adherence or by geometric factions, such as being formed in place or softened and subsequently molded or formed into microparticles which are trapped at a desired location; are capable of being delivered by techniques of minimum invasivity such as by catheter, laparoscope or endoscope. Sustained release matrices include polyesters, hydrogels, polylactides (U.S. Pat. No. 3,773,919, EP 58,481), copolymers of L-glutamic acid and gamma ethyl-L-glutamate (Sidman et al, *Biopolymers,* 22: 547-556, 1983), poly (2-hydroxyethyl-methacrylate) (Langer et al., *J.*

*Biomed. Mater. Res.*, 15: 167-277, 1981 and Langer, *Chem. Tech.*, 12: 98-105, 1982), ethylene vinyl acetate (Langer et al., supra) or poly-D(-)-3-hydroxybutyric acid (EP 133,988). Sustained-release compositions also may include liposomes, which can be prepared by any of several methods known in the art (e.g., Eppstein et al., *Proc. Natl. Acad. Sci. USA*, 82: 3688-3692, 1985; EP 36,676; EP 88,046; EP 143,949, incorporated herein by reference).

The Fhm polypeptides, variants, derivatives or fragments thereof, may be employed alone, together, or in combination with other pharmaceutical compositions. The Fhm polypeptides, fragments, variants, and derivatives may be used in combination with cytokines, cytokine inhibitors, growth factors, antibiotics, anti-inflammatories, and/or chemotherapeutic agents as is appropriate for the indication being treated.

In some cases, it may be desirable to use Fhm polypeptide pharmaceutical compositions in an ex vivo manner. In such instances, cells, tissues, or organs that have been removed from the patient are exposed to Fhm polypeptide pharmaceutical compositions after which the cells, tissues and/or organs are subsequently implanted back into the patient.

In other cases, a Fhm polypeptide can be delivered by implanting into patients certain cells that have been genetically engineered, using methods such as those described herein, to express and secrete the polypeptides, fragments, variants, or derivatives. Such cells may be animal or human cells, and may autologous, heterologous or xenogeneic. Optionally, the cells may be immortalized. In order to decrease the chance of an immunological response, it is preferred that the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627, incorporated herein by reference. A system for encapsulating living cells is described in International Publication No: WO 91/10425. Techniques for formulating a variety of other sustained or controlled delivery means, such as liposome carriers, bio-erodible particles or beads, are also known to those in the art, and are described, for example, in U.S. Pat. No. 5,653,975, incorporated herein by reference. The cells, with or without encapsulation, may be implanted into suitable body tissues or organs of the patient.

As discussed herein, it may be desirable to treat isolated cell populations such as stem cells, lymphocytes, red blood cells, chondrocytes, neurons, and the like; add as appropriate with one or more Fhm polypeptides, variants, derivatives and/or fragments. This can be accomplished by exposing the isolated cells to the polypeptide, variant, derivative, or fragment directly, where it is in a form that is permeable to the cell membrane.

The present invention relates to improved methods for both the in vitro production of therapeutic proteins and for the production and delivery of therapeutic proteins by gene therapy.

Homologous Recombination

It is further envisioned that Fhm protein may be produced by homologous recombination, or with recombinant production methods utilizing control elements introduced into cells already containing DNA encoding Fhm. For example, homologous recombination methods may be used to modify a cell that contains a normally transcriptionally silent Fhm gene, or under expressed gene, and thereby produce a cell which expresses therapeutically efficacious amounts of Fhm. Homologous recombination is a technique originally developed for targeting genes to induce or correct mutations in transcriptionally active genes (Kucherlapati, *Prog. in Nucl. Acid Res. and Mol. Biol.*, 36:301, 1989). The basic technique was developed as a method for introducing specific mutations into specific regions of the mammalian genome (Thomas et al., *Cell*, 44:419-428, 1986; Thomas and Capecchi, *Cell*, 51:503-512, 1987; Doetschman et al., *Proc. Natl. Acad. Sci.*, 85:8583-8587, 1988) or to correct specific mutations within defective genes (Doetschman et al., *Nature*, 330:576-578, 1987). Exemplary homologous recombination techniques are described in U.S. Pat. No. 5,272,071; EP Publication No: 91 90 3051, EP Publication No. 505 500; PCT/US90/07642, International Publication No: WO 91/09955. incorporated herein by reference.

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA, into which insertion of the sequence is sought. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA which may interact with or control the expression of a Fhm polypeptide, e.g. flanking sequences. For example, a promoter/enhancer element, a suppresser, or an exogenous transcription modulatory element is inserted in the genome of the intended host cell in proximity and orientation sufficient to influence the transcription of DNA encoding the desired Fhm polypeptide. The control element controls a portion of the DNA present in the host cell genome. Thus, the expression of Fhm protein may be achieved not by transfection of DNA that encodes the Fhm gene itself, but rather by the use of targeting DNA (containing regions of homology with the endogenous gene of interest) coupled with DNA regulatory segments that provide the endogenous gene sequence with recognizable signals for transcription of a Fhm protein.

In an exemplary method, expression of a desired targeted gene in a cell (i.e., a desired endogenous cellular gene) is altered by the introduction, by homologous recombination into the cellular genome at a preselected site, by the introduction of DNA which includes at least a regulatory sequence, an exon and a splice donor site. These components are introduced into the chromosomal (genomic) DNA in such a manner that this, in effect, results in the production of a new transcription unit (in which the regulatory sequence, the exon and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) expression of a gene which is expressed in the cell as obtained.

One method by which homologous recombination can be used to increase, or cause, Fhm polypeptide production from a cell's endogenous Fhm gene involves first using homologous recombination to place a recombination sequence from a site-specific recombination system (e.g., Cre/loxP, FLP/FRT) (see, Sauer, *Current Opinion In Biotechnology*, 5:521-527, 1994; and Sauer, *Methods In Enzymology*, 225:890-900, 1993) upstream (that is, 5' to) of the cell's endogenous genomic Fhm polypeptide coding region. A plasmid containing a recombination site homologous to the site that was placed just upstream of the genomic Fhm polypeptide coding region is introduced into the modified cell line along with the appropriate recombinase enzyme. This recombinase enzyme causes the plasmid to integrate, via the plasmid's recombination site, into the recombination site located just upstream of the genomic Fhm polypeptide coding region in the cell line (Baubonis and Sauer, *Nucleic Acids Res.*, 21:2025-2029, 1993; and O'Gorman et al., *Science*, 251:1351-1355, 1991). Any flanking sequences known to increase transcription (e.g., enhancer/promoter, intron, or translational enhancer), if properly positioned in this plasmid, would integrate in such a manner as to create a new or modified transcriptional unit resulting in de novo or increased Fhm polypeptide production from the cell's endogenous Fhm gene.

A further method to use the cell line in which the site-specific recombination sequence has been placed just upstream of the cell's endogenous genomic Fhm polypeptide coding region is to use homologous recombination to introduce a second recombination site elsewhere in the cell line's genome. The appropriate recombinase enzyme is then introduced into the two-recombination-site cell line, causing a recombination event (deletion, inversion, or translocation) (Sauer, *Current Opinion In Biotechnology*, supra, 1994; and Sauer, *Methods In Enzymology*, supra, 1993) that would create a new or modified transcriptional unit resulting in de novo or increased Fhm polypeptide production from the cell's endogenous Fhm gene.

An additional approach for increasing, or causing, the expression of Fhm polypeptide from a cell's endogenous Fhm gene involves increasing, or causing, the expression of a gene or genes (e.g., transcription factors) and/or decreasing the expression of a gene or genes (e.g., transcriptional repressors) in a manner which results in de novo or increased Fhm polypeptide production from the cell's endogenous Fhm gene. This method includes the introduction of a non-naturally occurring polypeptide (e.g., a polypeptide comprising a site specific site-specific DNA binding domain fused to a transcriptional factor domain) into the cell such that de novo or increased Fhm polypeptide production from the cell's endogenous Fhm gene results.

The present invention further relates to DNA constructs useful in the method of altering expression of a target gene. In certain embodiments, the exemplary DNA constructs comprise: (a) on or more targeting sequence; (b) a regulatory sequence; (c) an exon; and (d) an unpaired splice-donor site.

The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequence, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of Fhm presented herein, a piece of DNA that is complementary to a selected region of the gene can be synthesized or otherwise obtained, such as by appropriate restriction of the native DNA at specific recognition sites bounding the region of interest. This piece serves as a targeting sequence(s) upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding Fhm-polypeptide(s), which nucleotides may be used as targeting sequences.

Alternatively, gene therapy can be employed as described below.

Fhm Cell Therapy and Gene Therapy

Fhm cell therapy, e.g., the implantation of cells producing Fhm, is also encompassed by the present invention. This embodiment involves implanting cells capable of synthesizing and secreting a biologically active form of the soluble Fhm. Such soluble Fhm polypeptide producing cells may be cells that are natural producers of Fhm or may be recombinant cells whose ability to produce Fhm has been augmented by transformation with a gene encoding the desired Fhm molecule or with a gene augmenting the expression of Fhm, polypeptide. Such a modification may be accomplished by means of a vector suitable for delivering the gene as well as promoting its expression and secretion. In order to minimize a potential immunological reaction in patients being administered a Fhm polypeptide as may occur with the administration of a polypeptide of a foreign species, it is preferred that the natural cells producing Fhm be of human origin and produce human Fhm. Likewise, it is preferred that the recombinant cells producing Fhm be transformed with an expression vector containing a gene encoding a human Fhm polypeptide.

Implanted cells may be encapsulated to avoid the infiltration of surrounding tissue. Human or non-human animal cells may be implanted in patients in biocompatible, semipermeable polymeric enclosures or membranes that allow release of Fhm polypeptide but that prevent the destruction of the cells by the patient's immune system or by other detrimental factors from the surrounding tissue. Alternatively, the patient's own cells, transformed to produce Fhm polypeptides ex vivo, may be implanted directly into the patient without such encapsulation.

Techniques for the encapsulation of living cells are known in the art, and the preparation of the encapsulated cells and their implantation in patients may be accomplished without undue experimentation. For example, Baetge et al. (WO 95105452 and PCT/US94/09299) describe membrane capsules containing genetically engineered cells for the effective delivery of biologically active molecules. The capsules are biocompatible and are easily retrievable. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538, 5,011,472, and 5,106,627, incorporated herein by reference. A system for encapsulating living cells is described in International Application WO 91/10425 of Aebischer et al., International Application No. WO 91/10470 of Aebischer et al.; Winn et al., *Exper. Neurol.*, 113:322-329, 1991, Aebischer et al., *Exper. Neurol.*, 111:269-275, 1991; and Tresco et al., *ASAIO*, 38:17-23, 1992, incorporated herein by reference.

In vivo and in vitro gene therapy delivery of Fhm is also encompassed by the present invention. In vivo gene therapy may be accomplished by introducing the gene encoding Fhm into cells via local injection of a polynucleotide molecule or other appropriate delivery vectors. (Hefti, *J. Neurobiology,* 25:1418-1435, 1994). For example, a polynucleotide molecule encoding Fhm may be contained in an adeno-associated virus vector for delivery to the targeted cells (See for e.g., International Publication No. WO 95/34670; International Application No. PCT/US95/07178). The recombinant adeno-associated virus (AAV) genome typically contains AAV inverted terminal repeats flanking a DNA sequence encoding Fhm operably linked to functional promoter and polyadenylation sequences.

Alternative viral vectors include, but are not limited to, retrovirus, adenovirus, herpes simplex virus and papilloma virus vectors. U.S. Pat. No. 5,672,344 (issued Sep. 30, 1997, Kelley et al., University of Michigan) describes an in vivo viral-mediated gene transfer system involving a recombinant neurotrophic HSV-1 vector. U.S. Pat. No. 5,399,346 (issued Mar. 21, 1995, Anderson et al., Department of Health and human Services) provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (issued May 20, 1997, Woo et al., Baylor College of Medicine) involving adenoviral vectors; U.S. Pat. No. 5,672,510 (issued Sep. 30, 1997, Eglitis et al., *Genetic Therapy*, Inc.) involving retroviral vectors; and U.S. Pat. No. 5,635,399 (issued Jun. 3, 1997, Kriegler et al., *Chiron Corporation*) involving retroviral vectors expressing cytokines.

Nonviral delivery methods include liposome-mediated transfer, naked DNA delivery (direct injection), receptor-mediated transfer (ligand-DNA complex), electroporation, calcium phosphate precipitation and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, transcription factors to enhance expression by a vector as well as methods of vector manufacture. Such additional methods and materials for the practice of gene therapy techniques are described in U.S. Pat. No. 4,970,154 (issued Nov. 13, 1990, D.C. Chang, Baylor College of Medicine) electroporation techniques; International Application No. WO 9640958 (published 961219, Smith et al., *Baylor College of Medicine*) nuclear ligands; U.S. Pat. No. 5,679,559 (issued Oct. 21, 1997, Kim et al., *University of Utah Research Foundation*) concerning a lipoprotein-containing system for gene delivery; U.S. Pat. No. 5,676,954 (issued Oct. 14, 1997, K. L. Brigham, Vanderbilt University involving liposome carriers; U.S. Pat. No. 5,593,875 (issued Jan. 14, 1997, Wurm et al., *Genentech, Inc.*) concerning methods for calcium phosphate transfection; and U.S. Pat. No. 4,945,050 (issued Jul. 31, 1990, Sanford et al., *Cornell Research Foundation*) wherein biologically active particles are propelled at cells at a speed whereby the particles penetrate the surface of the cells and become incorporated into the interior of the cells. Expression control techniques include chemical induced regulation (e.g., International Application Nos. WO 9641865 and WO 9731899), the use of a progesterone antagonist in a modified steroid hormone receptor system (e.g., U.S. Pat. No. 5,364,791), ecdysone control systems (e.g., International Application No. WO 9637609), and positive tetracycline-controllable transactivators (e.g., U.S. Pat. Nos. 5,589,362; 5,650,298; and 5,654,168).

It is also contemplated that Fhm gene therapy or cell therapy can further include the delivery of a second protein. For example, the host cell may be modified to express and release soluble forms of both Fhm and TNF-$\alpha$, or Fhm and IL-1. Alternatively, the Fhm and TNF-$\alpha$, or Fhm and IL-1, may be expressed in and released from separate cells. Such cells may be separately introduced into the patient or the cells may be contained in a single implantable device, such as the encapsulating membrane described above.

One manner in which gene therapy can be applied is to use the Fhm gene (either genomic DNA, cDNA, and/or synthetic DNA encoding a Fhm polypeptide, or a fragment, variant, or derivative thereof) which may be operably linked to a constitutive or inducible promoter to form a "gene therapy DNA construct". The promoter may be homologous or heterologous to the endogenous Fhm gene, provided that it is active in the cell or tissue type into which the construct will be inserted. Other components of the gene therapy DNA construct may optionally include, as required, DNA molecules designed for site-specific integration (e.g., endogenous flanking sequences useful for homologous recombination), tissue-specific promoter, enhancer(s) or silencer(s), DNA molecules capable of providing a selective advantage over the parent cell, DNA molecules useful as labels to identify transformed cells, negative selection systems, cell specific binding agents (for example, for cell targeting) cell-specific internalization factors, and transcription factors to enhance expression by a vector as well as factors to enable vector manufacture.

A gene therapy DNA construct can then be introduced into the patient's cells (either ex vivo or in vivo) using viral or non-viral vectors. One means for introducing the gene therapy DNA construct. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm. The use of gene therapy vectors is described, for example, in U.S. Pat. Nos. 5,672,344; 5,399,346; 5,631,236; and 5,635,399, incorporated herein by reference.

In yet other embodiments, regulatory elements can be included for the controlled expression of the Fhm gene in the target cell. Such elements are turned on in response to an appropriate effector. In this way, a therapeutic polypeptide can be expressed when desired. One conventional control means involves the use of small molecule dimerizers or rapalogs (as described in WO 9641865 (PCT/US96/099486); WO 9731898 (PCT/US97/03137) and WO9731899 (PCT/US95/ 03157) WO 9731899 (PCT/US95/03157)) used to dimerize chimeric proteins which contain a small molecule-binding domain and a domain capable of initiating biological process, such as a DNA-binding protein or a transcriptional activation protein. The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain which results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See, *Science* 287:816-817, and 826-830 (2000).

Other suitable control means or gene switches include, but are not limited to, the following systems. Mifepristone (RU486) is used as a progesterone antagonist. The binding of a modified progesterone receptor ligand-binding domain to the progesterone antagonist activates transcription by forming a dimer of two transcription factors which then pass into the nucleus to bind DNA. The ligand bindingligand-binding domain is modified to eliminate the ability of the receptor to bind to the natural ligand. The modified steroid hormone receptor system is further described in U.S. Pat. No. 5,364,791; WO9640911, and WO9710337, WO 9640911 and WO 9710337.

Yet another control system uses ecdysone (a fruit fly steroid hormone) which binds to and activates an ecdysone receptor (cytoplasmic receptor). The receptor then translocates to the nucleus to bind a specific DNA response element (promoter from ecdysone-responsive gene). The ecdysone receptor includes a transactivation domain/DNA-binding domain/ligand-binding domain to initiate transcription. The ecdysone system is further described in U.S. Pat. No. 5,514,578; WO9738117; WO9637609; WO 9738117; WO 9637609 and WO9303162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758; 5,650,298 and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding an Fhm polypeptide into cells via local injection of an Fhm nucleic acid molecule or by other appropriate viral or non-non-viral delivery vectors. (Hefti, Neurobiology, 25:1418-1435, 1994). For example, a nucleic acid molecule encoding an Fhm polypeptide may be contained in an adeno-associated virus (AAV) vector for delivery to the targeted cells (e.g., Johnson, International Publication No. WO95/34670; and International Application No. PCT/US95/07178). The recombinant AAV genome typically contains AAV inverted terminal repeats flanking a DNA sequence encoding an Fhm polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 involving adenoviral vectors; U.S. Pat. No. 5,672,510 involving retroviral vectors; and U.S. Pat. No. 5,635,399 involving retroviral vectors expressing cytokines.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 involving electroporation techniques; WO96/40958 involving nuclear ligands; U.S. Pat. No. 5,679,559 describing a lipoprotein-containing system for gene delivery; U.S. Pat. No. 5,676,954 involving liposome carriers; U.S. Pat. No. 5,593,875 concerning methods for calcium phosphate transfection; and U.S. Pat. No. 4,945,050 wherein biologically active particles are propelled at cells at a speed whereby the particles penetrate the surface of the cells and become incorporated into the interior of the cells.

A means to increase endogenous Fhm polypeptide expression in a cell via gene therapy is to insert one or more enhancer elements into the Fhm polypeptide promoter, where the enhancer element(s) can serve to increase transcriptional activity of the Fhm polypeptides gene. The enhancer element(s) used will be selected based on the tissue in which one desires to activate the gene(s); enhancer elements known to confer promoter activation in that tissue will be selected. For example, if a Fhm gene encoding a Fhm polypeptide is to be "turned on" in T-cells, the lck promoter enhancer element may be used. Here, the functional portion of the transcriptional element to be added may be inserted into a fragment of DNA containing the Fhm polypeptide promoter (and optionally, inserted into a vector, 5' and/or 3' flanking sequence(s), etc.) using standard cloning techniques. This construct, known as a "homologous recombination construct", can then be introduced into the desired cells either ex vivo or in vivo.

Gene therapy also can be used to decrease Fhm polypeptide expression where desired by modifying the nucleotide sequence of the endogenous promoter(s). Such modification is typically accomplished via homologous recombination methods. For example, a DNA molecule containing all or a portion of the promoter of the Fhm gene(s) selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding Fhm gene. The deletion of the TATA box or the transcription activator binding site in the promoter may be accomplished by generating a DNA construct comprising all or the relevant portion of the Fhm polypeptide promoter(s) (from the same or a related species as the Fhm gene(s) to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. The construct, which also will typically contain at least about 500 bases of DNA that correspond to the native (endogenous) 5' and 3' DNA sequences adjacent to the promoter segment that has been modified. The construct may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Additional Uses of Fhm Nucleic Acids and Polypeptides

Nucleic acid molecules of the present invention (including those that do not themselves encode biologically active polypeptides) may be used to map the locations of the Fhm gene and related genes on chromosomes. Mapping may be done by techniques known in the art, such as PCR amplification and in situ hybridization.

Fhm nucleic acid molecules (including those that do not themselves encode biologically active polypeptides), may be useful as hybridization probes in diagnostic assays to test, either qualitatively or quantitatively, for the presence of an Fhm DNA or corresponding RNA in mammalian tissue or bodily fluid samples.

The Fhm polypeptides may be used (simultaneously or sequentially) in combination with one or more cytokines, growth factors, antibiotics, anti-inflammatories, and/or chemotherapeutic agents as is appropriate for the indication being treated.

Other methods may also be employed where it is desirable to inhibit the activity of one or more Fhm polypeptides. Such inhibition may be effected by nucleic acid molecules which are complementary to and which hybridize to expression control sequences (triple helix formation) or to Fhm mRNA. For example, antisense DNA or RNA molecules, which have a sequence that is complementary to at least a portion of the selected Fhm gene(s) can be introduced into the cell. Antisense probes may be designed by available techniques using the sequence of Fhm polypeptide disclosed herein. Typically, each such antisense molecule will be complementary to the start site (5' end) of each selected Fhm gene. When the antisense molecule then hybridizes to the corresponding Fhm mRNA, translation of this mRNA is prevented or reduced. Anti-sense inhibitors provide information relating to the decrease or absence of an Fhm polypeptide in a cell or organism.

Alternatively, gene therapy may be employed to create a dominant-negative inhibitor of one or more Fhm polypeptides. In this situation, the DNA encoding a mutant polypeptide of each selected Fhm polypeptide can be prepared and introduced into the cells of a patient using, either viral or non-viral methods as described herein. Each such mutant is typically designed to compete with endogenous polypeptide in its biological role.

In addition, an Fhm polypeptide, whether biologically active or not, may be used as an immunogen, that is, the polypeptide contains at least one epitope to which antibodies may be raised. Selective binding agents that bind to an Fhm polypeptide (as described herein) may be used for in vivo and in vitro diagnostic purposes, including, but not limited to, use in labeled form to detect the presence of Fhm polypeptide in a body fluid or cell sample. The antibodies may also be used to prevent, treat, or diagnose a number of diseases and disorders, including those recited herein. The antibodies may bind to an Fhm polypeptide so as to diminish or block at least one activity characteristic of an Fhm polypeptide, or may bind to a polypeptide to increase at least one activity characteristic of an Fhm polypeptide (including by increasing the pharmacokinetics of the Fhm polypeptide).

The following examples are intended for illustration purposes only, and should not be construed as limiting the scope of the invention in any way

EXAMPLE 1

Isolation of DNA Encoding Human Fhm

A TNF family profile search of the Amgen expressed sequence tag (EST) database identified an EST clone designated Fhm1-00016-g12 from a human macrophage cDNA library encoding a potential TNF ligand family member. A full-length cDNA encoding Fhm was obtained by PCR of first strand cDNA prepared from the 5637 cell line (ATCC # HTB-9) using the following primers:

1406-53: 5' GCCGAGGATCTGGGA CTGA (SEQ ID NO:1)

1468-66 5' TCGCCAATCCTCCAACCCATCTTA (SEQ ID NO:2)

The Fhm cDNA comprises 819 nucleotides (SEQ ID NO: 3) and encodes a polypeptide comprising 251 amino acids (SEQ ID NO: 4). Fasta search of the SwissProt database with the predicted Fhm protein sequence indicated that it is mostly related to TNFa with 28% identity in the C-terminal 162 amino acid overlap. Like other TNF ligand family members. Fhm is a type II transmembrane protein, containing a short N-terminal intracellular domain (amino acids 1-36), a hydrophobic transmembrane region (amino acids 37-56) and a long C-terminal extracellular domain (amino acids 57-251). The C-terminal extracellular domain of Fhm contained most of the conserved region of the TNF ligand family (Smith et al., *Cell* 76:952-62, 1994).

EXAMPLE 2

Tissue Specific Expression of Fhm

Tissue specific expression patterns of Fhm gene may be investigated by Northern blot analysis using a $^{32}$P labeled PCR product as a probe to detect the presence of Fhm transcript in various tissues.

Cytoplasmic and poly-A+ RNA is isolated from placenta, developing embryos, and various adult tissues using standard techniques Sambrook, J. et al, *Molecular Cloning*, Cold Spring Harbor Laboratory Press, New York (1989). Cells/tissues are lysed with 20 ml of TRIzol reagent (BRL), homogenized for 30 seconds, and extracted with 4 ml of chloroform. The tubes were centrifuged at 4000 rpm for 30 minutes and the aqueous phase was transferred to new tubes. RNA was precipitated by adding 10 ml isopropanol, mixing, and centrifuging for 30 minutes at 4200 rpm. The RNA pellet was washed with 10 ml of 70% ethanol, dried briefly, and resuspended in 0.5 ml TE buffer. Poly A$^+$ RNA is prepared by using a commercially available mRNA purification kit (Pharmacia). After elution of poly A$^-$ RNA from the column in 750 μl of TE buffer, the sample was then ethanol precipitated by adding 40 μl sample buffer and 1 ml ethanol and maintaining at −70° C. overnight. Poly A$^-$ RNA was then fractionated using a formaldehyde/agarose gel electrophoresis system. Following electrophoresis, the gel is processed and the RNA transferred to a nylon membrane. See Sambrook et al. Supra. Northern blots are then prehybridized in 20 ml of prehybridization solution containing 5×SSPE, 50% formamide, 5×Denhardt's solution, 0.5% SDS and 100 μg/ml denatured salmon sperm DNA for 2-4 hours at 42° C. The blots were then hybridized in 20 ml of hybridization solution containing 6×SSPE, 50% formamide, 5×Denhardt's solution, 0.5% SDS, 100 ug/ml denatured salmon sperm DNA. Approximately 5 ng/ml of random primed, $^{32}$P-labeled (RadPrime Kit, GEBCO) Fhm full length cDNA was used as a probe. The blots were hybridized for 18-24 hours at 42° C. The blots were then washed in 0.1×SSC. 0.1% SDS at 55° C. The blots were then exposed to x-ray films for three days at 80° C. A weak expression of Fhm was detected in the kidneys.

EXAMPLE 3

Production of Fhm Polypeptides

A. Expression of Fhm Polypeptide in Bacteria

PCR are used to amplify template DNA sequences encoding an Fhm polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC No. 98113) containing the lux promoter and a gene encoding kanamycin resistance is digested with BamHI and NdeI for directional cloning of inserted DNA. The ligated mixture is transformed into E. coli host strain 393 by electroporation and transformants selected for kanamycin resistance. Plasmid DNA from selected colonies is isolated and subjected to DNA sequencing to confirm the presence of the insert.

Transformed host cells are incubated in 2XYT medium containing 30 μg/ml kanamycin at 30° C. prior to induction. Gene expression can then be induced by addition of N-(3-oxohexanoyl)-dl-homoserine lactone to a final concentration of 30 ng/ml followed by incubation at either 30° C. or 37° C. for six hours. Expression of Fhm polypeptide is evaluated by centrifugation of the culture, resuspension and lysis of the bacterial pellets, and analysis of host cell proteins by SDS-polyacrylamide gel electrophoresis.

Inclusion bodies containing Fhm polypeptide are purified as follows: Bacterial cells are pelleted by centrifugation and resuspended in water. The cell suspension is lysed by sonication and pelleted by centrifugation at 195,000×g for 5 to 10 minutes. The supernatant is discarded and the pellet washed and transferred to a homogenizer. The pellet is homogenized in 5 ml. of a Percoll solution (75% liquid Percoll. 0.15M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE. Recombinant Fhm protein was purified as previously described (WO 98/46751)

EXAMPLE 4

Production of Anti-Fhm Antibodies

Antibodies to Fhm polypeptides may be obtained by immunization with purified Fhm protein or with Fhm peptides produced by biological or chemical synthesis. Substantially pure Fhm protein or polypeptide may be isolated from transfected cells as described in Example 3. Concentration of protein in the final preparation may be adjusted, for example, by concentration on an amicon filter device, to the level of a few micrograms/ml. Monoclonal or polyclonal antibodies to the protein can then be prepared by any of the procedures known in the art for generating antibodies such as those described in Hudson and Bay, "Practical Immunology, Second Edition", Blackwell Scientific Publications, incorporated herein by reference.

Polyclonal antiserum containing antibodies to heterogenous epitopes of a single protein can be prepared by immunizing suitable animals with the expressed protein described above, which can be unmodified or modified to enhance immunogenicity. Effective polyclonal antibody production is affected by many factors related both to the antigen and the host species. For example, small molecules tend to be less immunogenic than large molecules and may require the use of carriers or adjuvants. Also, host animals vary in response to site of inoculations and dose, with both inadequate or excessive doses of antigen resulting in low titer antisera. Small doses (ng levels) of antigen administered at multiple intradermal sites appear to be most reliable. An effective immunization protocol for rabbits can be found in Vaitukaitis, J. et al. *J. Clin. Endocrinol. Metab.* 33: 988-991, 1971.

Booster injections can be given at regular intervals, and antiserum harvested when antibody titer thereof, as determined semi-quantitatively, for example, by double immunodiffusion in agar against known concentrations of the antigen, begin to fall. See, for example, Ouchterlony, O. et al., Chap. 19 in: *Handbook of Experimental Immunology* ed. D. Weir, Blackwell, 1973. Plateau concentration of antibody is usually in the range of 0.1 to 0.2 mg/ml of serum (about 12 um). Affinity of the antisera for the antigen is determined by preparing competitive binding curves, as described, for example, by Fisher, D., Chapt. 42 in; *Manual of Clinical Immunology*, 2d Ed. (Rose and Friedman, eds.) Amer. Soc. For Microbiol., Washington, D.C., 1980.

Alternative procedures for obtaining anti-Fhm antibodies may also be employed, such as immunization of transgenic mice harboring human Ig loci for production of fully human antibodies, and screening of synthetic antibody libraries, such as those generated by mutagenesis of an antibody variable domain.

EXAMPLE 5

Functional Analysis of the Role of Fhm

To determine the functional role of Fhm in vivo, the Fhm gene is either over expressed in the germ line of animals or inactivated in the germ line of mammals by homologous recombination. See, e.g, U.S. Pat. No. 5,489,743 and International Patent Publication No. WO 94/28122, incorporated herein by reference. Animals in which the gene is over expressed under the regulatory control of exogenous or endogenous promoter elements are known as transgenic animals. Animals in which an endogenous gene has been inactivated by homologous recombination are also known as "knockout" animals. Exemplary mammals include rabbits and rodent species such as mice.

Transgenic animals allow for the determination of the effect(s) of over expression or inappropriate expression of the Fhm on development and disease processes. Fhm transgenic animals can also serve as a model system to test compounds that can modulate receptor mediated Fhm activity.

The "knockout" animals allow for the determination of the role of Fhm in embryonic development, and in immune and proliferative responses. The role of Fhm in development, and in immune and proliferative response is determined by analysis the effect(s) of gene knockout on the development of the embryo as well as on the development and differentiation of various organs and tissues such as the immune system in these animals. (as determined by FACS analysis of cell populations at different stages of development).

EXAMPLE 6

Specific Recognition of Fhm by Soluble TNF-receptor Family Member NTR3

For receptor binding assay, $2 \times 10^5$ COS-7 cells were seeded in 6-well plate. The next day, cells were transfected with expression plasmid for Fhm by lipofectamin methods according to the manufacturer's instructions (Gibco BRL). The eukaryotic expression vector PCEP4 (Invitrogen) was used to generate the cDNA construct. After 48 hours of transfection, the tissue culture medium was replaced with tissue culture medium containing TNF-receptor family member(s) fused with human IgG Fc portion. After 1 hour incubation at room temperature (RT), cells were washed three times with 5 ml PBS. Cells were then incubated in DMEM medium containing 5% BSA and 1:500 dilution of goat anti-human IgG Fc conjugated with alkaline phosphatase (Sigma) for another hour at RT. After three washes with 5 ml TBS buffer, cells were stained with Fast Red TR/AS-MX Substrate Kit (Pierce). Positive staining was determined by visual examination under microscope. Fhm transfected COS-7 cells were specifically recognized by NTR3Fc fusion protein. The NTR3 protein, a member of the TNF receptor supergene family, is described in detail in co-owned, co-filed U.S. Provisional Patent Application No. 60/147,297, filed Aug. 4, 1999, incorporated herein by reference in its entirety.

The term "NTR3 nucleic acid molecule" refers to a nucleic acid molecule comprising or consisting essentially of a nucleotide sequence as set forth in SEQ ID NO: 22, comprising or consisting essentially of a nucleotide sequence encoding the polypeptide as set forth in SEQ ID NO: 23, or nucleic acid molecules related thereto. "Related" nucleic acid molecules comprise or consist essentially of a nucleotide sequence that is about 70 percent identical to the nucleotide sequence as shown in SEQ ID NO: 22, or comprise or consist essentially of a nucleotide sequence encoding a polypeptide having an amino acid sequence that is about 70 percent identical to the amino acid sequence as set forth in SEQ ID NO: 23. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 22, or the nucleotide sequences encode a polypeptide that is about 75 percent, or about 80 percent, or about 85 percent, or about 90 percent, or about 95, 96, 97, 98, or 99 percent identical to the polypeptide sequence as set forth in SEQ ID NO: 23. Related nucleic acid molecules also include fragments of the above NTR3 nucleic acid molecules which are at least about 10 contiguous nucleotides, or about 15, or about 20, or about 25, or about 50, or about 75, or about 100, or greater than about 100 contiguous nucleotides. Related nucleic acid molecules also include fragments of the above NTR3 nucleic acid molecules which encode a polypeptide of at least about 25 amino acid residues, or about 50, or about 75, or about 100, or greater than about 100 amino acid residues. Related nucleic acid molecules also include a nucleotide sequence encoding a polypeptide comprising or consisting essentially of a substitution and/or a deletion of one or more of amino acids 1-300 with reference to the polypeptide in SEQ ID NO: 23. Related NTR3 nucleic acid molecules include those molecules which comprise nucleotide sequences which hybridize under moderate or highly stringent conditions as defined herein with any of the above nucleic acid molecules. In preferred embodiments, the related nucleic acid molecules comprise sequences which hybridize under moderate or highly stringent conditions with the sequence as shown in SEQ ID NO: 22, or with a molecule encoding a polypeptide, which polypeptide comprises the sequence as shown in SEQ ID NO: 23, or with a nucleic acid fragment as defined above, or with a nucleic acid fragment encoding a polypeptide as defined above. It is also understood that related nucleic acid molecules include allelic or splice variants of any of the above nucleic acids, and include sequences which are complementary to any of the above nucleotide sequences.

The term "NTR3 polypeptide" refers to a polypeptide comprising the amino acid sequence of SEQ ID NO: 23 and related polypeptides described herein. "Related polypeptides" includes allelic variants, splice variants, fragments, derivatives, substitution, deletion, and/or insertion variants, fusion polypeptides, and orthologs. NTR3 polypeptides may be mature polypeptides, as defined herein, and may or may not have an amino terminal methionine residue, depending on the method by which they are prepared. The term "NTR3 polypeptide fragment" refers to a peptide or polypeptide that comprises less than the full length amino acid sequence of a NTR3 polypeptide as set forth in SEQ ID NO: 23. Such a fragment may arise, for example, from a truncation at the amino terminus, a truncation at the carboxy terminus, and/or an internal deletion of the amino acid sequence. NTR3 fragments may result from alternative RNA splicing or from in vivo protease activity. For transmembrane or membrane-bound forms of a NTR3 polypeptide, preferred fragments include soluble forms such as those lacking a transmembrane or membrane-binding domain. The term "NTR3 polypeptide variants" refers to NTR3 polypeptides comprising amino acid sequences which contain one or more amino acid sequence substitutions, deletions, and/or additions as compared to the NTR3 polypeptide amino acid sequence set forth in SEQ ID NO: 23. Variants may be naturally occurring or artificially constructed using recombinant DNA technology.

While the present invention has been described in terms of the preferred embodiments, it is understood that variations and modifications will occur to those skilled in the art. Therefore, it is intended that the appended claims cover all such equivalent variations which come within the scope of the invention as claimed.

The invention claimed is:

1. A method for identifying a compound that modulates the binding of a first polypeptide to a second polypeptide, the method comprising:
   (a) incubating the first and second polypeptides in the presence or absence of a test molecule, wherein the first polypeptide comprises the amino acid sequence set forth in SEQ ID NO: 4;
   wherein the first polypeptide binds to NTR3 and binds to the second polypeptide;
   wherein the second polypeptide comprises the amino acid sequence of NTR3 (SEQ ID NO: 23); and
   (b) measuring binding between the first and second polypeptides in the presence and absence of the test molecule, wherein differential binding in the presence versus the absence of the test molecule identifies the test molecule as a compound that modulates the binding.

2. The method of claim 1, wherein at least one of the first and second polypeptides is detectably-labeled.

3. The method of claim 2, further comprising a washing step prior to the measuring step to remove at least one of unbound first polypeptide and unbound second polypeptide.

4. The method of claim 1, wherein at least one of the first and second polypeptides is attached to a substrate.

5. The method of claim 1, wherein the first polypeptide is expressed on the surface of cells.

6. The method of claim 1, wherein at least one of the first and second polypeptides is fused to a heterologous peptide.

7. The method of claim 6, wherein the heterologous peptide is a Fc fragment.

8. The method of claim 1, wherein the test molecule is an antibody.

9. The method of claim 1, wherein the test molecule is a polypeptide comprising an antigen binding fragment of an antibody that specifically binds the first or second polypeptide.

10. The method of claim 1, wherein the test molecule is a monoclonal antibody.

11. The method of claim 1, wherein the test molecule is a humanized antibody.

12. The method of claim 1, wherein the test molecule is a fully human antibody.

13. The method of claim 1, wherein the test molecule is an antibody that binds to the first polypeptide.

14. The method of claim 1, wherein the test molecule is an antibody that binds to the second polypeptide.

15. The method of claim 1, wherein the test molecule is a fragment of the first polypeptide that binds the second polypeptide.

16. The method of claim 1, wherein the test molecule is a fragment of the second polypeptide that binds the first polypeptide.

17. The method according to claim 1 for identifying an antagonist of the binding between the first polypeptide and the second polypeptide, comprising selecting as an antagonist a test molecule that reduces the binding between the first polypeptide and the second polypeptide.

18. The method according to claim 1 for identifying an agonist of the binding between the first polypeptide and the second polypeptide, comprising selecting as an agonist a test molecule that increases the binding between the first polypeptide and the second polypeptide.

19. A method for identifying a compound that modulates the binding of a first polypeptide to a second polypeptide, the method comprising:
   (a) incubating the first and second polypeptides in the presence or absence of a test molecule, wherein the first polypeptide comprises an amino acid sequence at least 95% identical to an extracellular domain comprising amino acid residues 57 to 251 of SEQ ID NO: 4, wherein the second polypeptide comprises an amino acid sequence at least 95% identical to the amino acid sequence of NTR3 (SEQ ID NO: 23),
   wherein the first polypeptide binds to NTR3 and binds to the second polypeptide, and wherein the second polypeptide binds to a polypeptide that comprises the amino acid sequence of SEQ ID NO: 4 and binds to the first polypeptide; and
   (b) measuring binding between the first and second polypeptides in the presence and absence of the test molecule, wherein differential binding in the presence versus the absence of the test molecule identifies the test molecule as a compound that modulates the binding.

20. The method according to claim 19, wherein the first polypeptide comprises amino acid residues 57 to 251 of SEQ ID NO: 4.

21. The method of claim 19, wherein at least one of the first and second polypeptides is fused to a heterologous peptide.

22. The method of claim 21, wherein the heterologous peptide is a Fc fragment.

23. A method for identifying a compound that modulates the binding of a first polypeptide to a second polypeptide, the method comprising:
 (a) incubating the first and second polypeptides in the presence or absence of a test molecule, wherein the second polypeptide comprises an amino acid sequence at least 95% identical to the amino acid sequence of NTR3 (SEQ ID NO: 23), wherein the first polypeptide comprises the amino acid sequence set forth in SEQ ID NO: 4;
 wherein the first polypeptide binds to NTR3 and binds to the second polypeptide; and
 (b) measuring binding between the first and second polypeptides in the presence and absence of the test molecule, wherein differential binding in the presence versus the absence of the test molecule identifies the test molecule as a compound that modulates the binding.

24. A method for identifying a compound that modulates the binding of a first polypeptide to a second polypeptide, the method comprising:
 (a) incubating the first and second polypeptides in the presence or absence of a test molecule; wherein the first polypeptide comprises an amino acid sequence at least 95% identical to the amino acid sequence set forth in SEQ ID NO: 4,
 wherein the second polypeptide comprises the amino acid sequence of NTR3 (SEQ ID NO: 23);
 wherein the first polypeptide binds to NTR3, and wherein the second polypeptide binds to a polypeptide that comprises the amino acid sequence of SEQ ID NO: 4; and
 (b) measuring binding between the first and second polypeptides in the presence and absence of the test molecule, wherein differential binding in the presence versus the absence of the test molecule identifies the test molecule as a compound that modulates the binding.

25. A method for identifying a compound that modulates the binding of a first polypeptide to a second polypeptide, the method comprising:
 (a) incubating the first and second polypeptides in the presence or absence of a test molecule, wherein the first polypeptide comprises an amino acid sequence at least 95% identical to the amino acid sequence set forth in SEQ ID NO: 4, wherein the second polypeptide comprises an amino acid sequence at least 95% identical to the amino acid sequence of NTR3 (SEQ ID NO: 23),
 wherein the first polypeptide binds to NTR3 and binds to the second polypeptide, and wherein the second polypeptide binds to a polypeptide that comprises the amino acid sequence of SEQ ID NO: 4 and binds to the first polypeptide; and
 (b) measuring binding between the first and second polypeptides in the presence and absence of the test molecule, wherein differential binding in the presence versus the absence of the test molecule identifies the test molecule as a compound that modulates the binding.

\* \* \* \* \*

SEQUENCE LISTING

<160> NUMBER OF SEQ ID NOS: 24

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: PCR Primer for human FHM

<400> SEQUENCE: 1
gccgaggatc tgggactga                                              19

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: PCR Primer for human FHM

<400> SEQUENCE: 2
tcgccaatcc tccacccat ctta                                         24

<210> SEQ ID NO 3
<211> LENGTH: 819
<212> TYPE: DNA
<213> ORGANISM: Homo sapiens
<220> FEATURE:
<221> NAME/KEY: CDS
<222> LOCATION: (37)..(789)
<220> FEATURE:
<223> OTHER INFORMATION: Hu-Fhm

<400> SEQUENCE: 3

```
aagctgggta cagctgctag caagctctag accacc atg gcc gag gat ctg gga      54
                                       Met Ala Glu Asp Leu Gly
                                        1               5 ctg agc ttt ggg gaa aca gcc agt gtg gaa atg ctg cca gag cac ggc     102
Leu Ser Phe Gly Glu Thr Ala Ser Val Glu Met Leu Pro Glu His Gly
           10                  15                  20 agc tgc agg ccc aag gcc agg agc agc agc gca cgc tgg gct ctc acc    150
Ser Cys Arg Pro Lys Ala Arg Ser Ser Ser Ala Arg Trp Ala Leu Thr
         25                  30                  35 tgc tgc ctg gtg ttg ctc ccc ttc ctt gca gga ctc acc aca tac ctg    198
Cys Cys Leu Val Leu Leu Pro Phe Leu Ala Gly Leu Thr Thr Tyr Leu
 40                  45                  50 ctt gtc agc cag ctc cgg gcc cag gga gag gcc tgt gtg cag ttc cag    246
Leu Val Ser Gln Leu Arg Ala Gln Gly Glu Ala Cys Val Gln Phe Gln
 55                  60                  65                  70 gct cta aaa gga cag gag ttt gca cct tca cat cag caa gtt tat gca    294
Ala Leu Lys Gly Gln Glu Phe Ala Pro Ser His Gln Gln Val Tyr Ala
                 75                  80                  85 cct ctt aga gca gac gga gat aag cca agg gca cac ctg aca gtt gtg    342
Pro Leu Arg Ala Asp Gly Asp Lys Pro Arg Ala His Leu Thr Val Val
             90                  95                 100 aga caa act ccc aca cag cac ttt aaa aat cag ttc cca gct ctg cac    390
Arg Gln Thr Pro Thr Gln His Phe Lys Asn Gln Phe Pro Ala Leu His
        105                 110                 115 tgg gaa cat gaa cta ggc ctg gcc ttc acc aag aac cga atg aac tat    438
Trp Glu His Glu Leu Gly Leu Ala Phe Thr Lys Asn Arg Met Asn Tyr
    120                 125                 130
```

```
acc aac aaa ttc ctg ctg atc cca gag tcg gga gac tac ttc att tac    486
Thr Asn Lys Phe Leu Leu Ile Pro Glu Ser Gly Asp Tyr Phe Ile Tyr
135                 140                 145                 150 tcc cag gtc aca ttc cgt ggg atg acc tct gag tgc agt gaa atc aga    534
Ser Gln Val Thr Phe Arg Gly Met Thr Ser Glu Cys Ser Glu Ile Arg
                155                 160                 165 cga gca ggc cga cca aac aag cca gac tcc atc act gtg gtc atc acc    582
Arg Ala Gly Arg Pro Asn Lys Pro Asp Ser Ile Thr Val Val Ile Thr
        170                 175                 180 aag gta aca gac agc tac cct gag cca acc cag ctc ctc atg ggg acc    630
Lys Val Thr Asp Ser Tyr Pro Glu Pro Thr Gln Leu Leu Met Gly Thr
    185                 190                 195 aag tct gta tgc gaa gta ggt agc aac tgg ttc cag ccc atc tac ctc    678
Lys Ser Val Cys Glu Val Gly Ser Asn Trp Phe Gln Pro Ile Tyr Leu
200                 205                 210 gga gcc atg ttc tcc ttg caa gaa ggg gac aag cta atg gtg aac gtc    726
Gly Ala Met Phe Ser Leu Gln Glu Gly Asp Lys Leu Met Val Asn Val
215                 220                 225                 230 agt gac atc tct ttg gtg gat tac aca aaa gaa gat aaa acc ttc ttt    774
Ser Asp Ile Ser Leu Val Asp Tyr Thr Lys Glu Asp Lys Thr Phe Phe
                235                 240                 245 gga gcc ttc tta cta tagtaggtcg aggccggcaa ggccggatcc                819
Gly Ala Phe Leu Leu
            250

<210> SEQ ID NO 4
<211> LENGTH: 251
<212> TYPE: PRT
<213> ORGANISM: Homo sapiens

<400> SEQUENCE: 4

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Arg Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205
```

```
Phe Gln Pro Ile Tyr Leu Gly Ala Met Phe Ser Leu Gln Glu Gly Asp
        210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 5
<211> LENGTH: 69
<212> TYPE: PRT
<213> ORGANISM: Homo sapiens

<400> SEQUENCE: 5

Glu Lys Lys Glu Leu Arg Lys Val Ala His Leu Thr Gly Lys Ser Asn
1               5                   10                  15

Ser Arg Ser Met Pro Leu Glu Trp Glu Asp Thr Tyr Gly Ile Val Leu
            20                  25                  30

Leu Ser Gly Val Lys Tyr Lys Lys Gly Gly Leu Val Ile Asn Glu Thr
        35                  40                  45

Gly Leu Tyr Phe Val Tyr Ser Lys Val Tyr Phe Arg Gly Gln Ser Cys
    50                  55                  60

Asn Asn Leu Pro Leu
65

<210> SEQ ID NO 6
<211> LENGTH: 66
<212> TYPE: PRT
<213> ORGANISM: Mouse

<400> SEQUENCE: 6

Glu Lys Lys Glu Pro Arg Ser Val Ala His Leu Thr Gly Asn Pro His
1               5                   10                  15

Ser Arg Ser Ile Pro Leu Glu Trp Glu Asp Thr Tyr Gly Thr Ala Leu
            20                  25                  30

Ile Ser Gly Val Lys Tyr Lys Lys Gly Gly Leu Val Ile Asn Glu Thr
        35                  40                  45

Phe Val Tyr Ser Lys Val Tyr Phe Arg Gly Gln Ser Cys Asn Asn Gln
    50                  55                  60

Pro Leu
65

<210> SEQ ID NO 7
<211> LENGTH: 66
<212> TYPE: PRT
<213> ORGANISM: Rat

<400> SEQUENCE: 7

Glu Thr Lys Lys Pro Arg Ser Val Ala His Leu Thr Gly Asn Pro Arg
1               5                   10                  15

Ser Arg Ser Ile Pro Leu Glu Trp Glu Asp Thr Tyr Gly Thr Ala Leu
            20                  25                  30

Ile Ser Gly Val Lys Tyr Lys Lys Gly Gly Leu Val Ile Asn Glu Ala
        35                  40                  45

Phe Val Tyr Ser Lys Val Tyr Phe Arg Gly Gln Ser Cys Asn Ser Gln
    50                  55                  60

Pro Leu
65
```

```
<210> SEQ ID NO 8
<211> LENGTH: 71
<212> TYPE: PRT
<213> ORGANISM: Homo sapiens

<400> SEQUENCE: 8

Gly Asp Gln Asn Pro Gln Ile Ala Ala His Val Ile Ser Glu Ala Ser
1               5                   10                  15

Ser Lys Thr Thr Ser Val Leu Gln Trp Ala Glu Lys Gly Tyr Tyr Thr
            20                  25                  30

Met Ser Asn Asn Leu Val Thr Leu Glu Asn Gly Lys Gln Leu Thr Val
        35                  40                  45

Lys Arg Gln Tyr Ile Tyr Ala Gln Val Thr Phe Cys Ser Asn Arg Glu
    50                  55                  60

Ala Ser Ser Gln Ala Pro Phe
65                  70

<210> SEQ ID NO 9
<211> LENGTH: 74
<212> TYPE: PRT
<213> ORGANISM: Mouse

<400> SEQUENCE: 9

Gly Asp Glu Asp Pro Gln Ile Ala Ala His Val Val Ser Glu Ala Asn
1               5                   10                  15

Ser Asn Ala Ala Ser Val Leu Gln Trp Ala Lys Lys Gly Tyr Tyr Thr
            20                  25                  30

Met Lys Ser Asn Leu Val Met Leu Glu Asn Gly Lys Gln Leu Thr Val
        35                  40                  45

Lys Arg Glu Gly Leu Tyr Tyr Val Tyr Thr Gln Val Thr Phe Cys Ser
    50                  55                  60

Asn Arg Glu Pro Ser Ser Gln Arg Pro Phe
65                  70

<210> SEQ ID NO 10
<211> LENGTH: 77
<212> TYPE: PRT
<213> ORGANISM: Mouse

<400> SEQUENCE: 10

Gly Lys Pro Glu Ala Gln Pro Phe Ala His Leu Thr Ile Asn Ala Ala
1               5                   10                  15

Ser Ile Pro Ser Gly Ser His Lys Val Thr Leu Ser Ser Trp Tyr His
            20                  25                  30

Asp Arg Gly Trp Ala Lys Ile Ser Asn Met Thr Leu Ser Asn Gly Lys
        35                  40                  45

Leu Arg Val Asn Gln Asp Gly Phe Tyr Tyr Leu Tyr Ala Asn Ile Cys
    50                  55                  60

Phe Arg His His Glu Thr Ser Gly Ser Val Pro Thr Asp
65                  70                  75

<210> SEQ ID NO 11
<211> LENGTH: 77
<212> TYPE: PRT
<213> ORGANISM: Homo sapiens

<400> SEQUENCE: 11

Ser Lys Leu Glu Ala Gln Pro Phe Ala His Leu Thr Ile Asn Ala Thr
1               5                   10                  15
```

-continued

Asp Ile Pro Ser Gly Ser His Lys Val Ser Leu Ser Ser Trp Tyr His
                20                  25                  30

Asp Arg Gly Trp Ala Lys Ile Ser Asn Met Thr Phe Ser Asn Gly Lys
            35                  40                  45

Leu Ile Val Asn Gln Asp Gly Phe Tyr Tyr Leu Tyr Ala Asn Ile Cys
        50                  55                  60

Phe Arg His His Glu Thr Ser Gly Asp Leu Ala Thr Glu
65                  70                  75

<210> SEQ ID NO 12
<211> LENGTH: 85
<212> TYPE: PRT
<213> ORGANISM: Homo sapiens

<400> SEQUENCE: 12

Glu Arg Gly Pro Gln Arg Val Ala Ala His Ile Thr Gly Thr Arg Gly
1               5                   10                  15

Arg Ser Asn Thr Leu Ser Ser Pro Asn Ser Lys Asn Glu Lys Ala Leu
                20                  25                  30

Gly Arg Lys Ile Asn Ser Trp Glu Ser Ser Arg Ser Gly His Ser Phe
            35                  40                  45

Leu Ser Asn Leu His Leu Arg Asn Gly Glu Leu Val Ile His Glu Lys
        50                  55                  60

Gly Phe Tyr Tyr Ile Tyr Ser Gln Thr Tyr Phe Arg Phe Gln Glu Glu
65                  70                  75                  80

Ile Lys Glu Asn Thr
                85

<210> SEQ ID NO 13
<211> LENGTH: 87
<212> TYPE: PRT
<213> ORGANISM: Mouse

<400> SEQUENCE: 13

Gly Gly Arg Pro Gln Lys Val Ala Ala His Ile Thr Gly Ile Thr Arg
1               5                   10                  15

Arg Ser Asn Ser Ala Leu Ile Pro Ile Ser Lys Asp Gly Lys Thr Leu
                20                  25                  30

Gly Gln Lys Ile Glu Ser Trp Glu Ser Ser Arg Lys Gly His Ser Phe
            35                  40                  45

Leu Asn His Val Leu Phe Arg Asn Gly Glu Leu Val Ile Glu Gln Glu
        50                  55                  60

Tyr Ile Tyr Ser Gln Thr Tyr Phe Arg Phe Gln Glu Ala Glu Asp Ala
65                  70                  75                  80

Ser Lys Met Val Ser Lys Asp
                85

<210> SEQ ID NO 14
<211> LENGTH: 64
<212> TYPE: PRT
<213> ORGANISM: Homo sapiens

<400> SEQUENCE: 14

Arg Ala Pro Phe Lys Lys Ser Trp Ala Tyr Leu Gln Val Ala Lys His
1               5                   10                  15

Leu Asn Lys Thr Lys Leu Ser Trp Asn Lys Asp Gly Ile Leu His Gly
                20                  25                  30

Val Arg Tyr Gln Asp Gly Asn Leu Val Ile Gln Phe Pro Phe Ile Ile

```
                  35                  40                  45

Cys Gln Leu Gln Phe Leu Val Gln Cys Pro Asn Asn Ser Val Asp Leu
         50                  55                  60

<210> SEQ ID NO 15
<211> LENGTH: 64
<212> TYPE: PRT
<213> ORGANISM: Mouse

<400> SEQUENCE: 15

Ser Thr Pro Ser Lys Lys Ser Trp Ala Tyr Leu Gln Val Ser Lys His
  1               5                  10                  15

Leu Asn Asn Thr Lys Leu Ser Trp Asn Glu Asp Gly Thr Ile His Gly
                 20                  25                  30

Leu Ile Tyr Gln Asp Gly Asn Leu Ile Val Gln Phe Pro Phe Ile Val
              35                  40                  45

Cys Gln Leu Gln Phe Leu Val Gln Cys Ser Asn His Ser Val Asp Leu
         50                  55                  60

<210> SEQ ID NO 16
<211> LENGTH: 73
<212> TYPE: PRT
<213> ORGANISM: Homo sapiens

<400> SEQUENCE: 16

Asp Leu Ser Pro Gly Leu Pro Ala Ala His Leu Ile Gly Ala Pro Leu
  1               5                  10                  15

Lys Gly Gln Gly Leu Gly Trp Glu Thr Thr Lys Glu Gln Ala Phe Leu
                 20                  25                  30

Thr Ser Gly Thr Gln Phe Ser Asp Ala Glu Gly Leu Ala Leu Pro Gln
              35                  40                  45

Asp Tyr Leu Tyr Cys Leu Val Gly Tyr Arg Gly Arg Ala Pro Pro Gly
         50                  55                  60

Gly Gly Asp Pro Gln Gly Arg Ser Val
 65                  70

<210> SEQ ID NO 17
<211> LENGTH: 75
<212> TYPE: PRT
<213> ORGANISM: Mouse

<400> SEQUENCE: 17

Asp Leu Asn Pro Glu Leu Pro Ala Ala His Leu Ile Gly Ala Trp Met
  1               5                  10                  15

Ser Gly Gln Gly Leu Ser Trp Glu Ala Ser Gln Glu Glu Ala Phe Leu
                 20                  25                  30

Arg Ser Gly Ala Gln Phe Ser Pro Thr His Gly Leu Ala Leu Pro Gln
              35                  40                  45

Asp Gly Val Tyr Tyr Leu Tyr Cys His Val Gly Tyr Arg Gly Arg Thr
         50                  55                  60

Pro Pro Ala Gly Arg Ser Arg Ala Arg Ser Leu
 65                  70                  75

<210> SEQ ID NO 18
<211> LENGTH: 75
<212> TYPE: PRT
<213> ORGANISM: Homo sapiens

<400> SEQUENCE: 18
```

```
Ala His Ser Thr Leu Lys Pro Ala Ala His Leu Ile Gly Asp Pro Ser
 1               5                  10                  15

Lys Gln Asn Ser Leu Leu Trp Arg Ala Asn Thr Asp Arg Ala Phe Leu
                 20                  25                  30

Gln Asp Gly Phe Ser Leu Ser Asn Asn Ser Leu Leu Val Pro Thr Ser
             35                  40                  45

Gly Ile Tyr Phe Val Tyr Ser Gln Val Val Phe Ser Gly Lys Ala Tyr
         50                  55                  60

Ser Pro Lys Ala Thr Ser Ser Pro Leu Tyr Leu
 65                  70                  75

<210> SEQ ID NO 19
<211> LENGTH: 72
<212> TYPE: PRT
<213> ORGANISM: Mouse

<400> SEQUENCE: 19

Thr His Gly Ile Leu Lys Pro Ala Ala His Leu Val Gly Tyr Pro Ser
 1               5                  10                  15

Lys Gln Asn Ser Leu Leu Trp Arg Ala Ser Thr Asp Arg Ala Phe Leu
                 20                  25                  30

Arg His Gly Phe Ser Leu Ser Asn Asn Ser Leu Leu Ile Pro Thr Ser
             35                  40                  45

Phe Val Tyr Ser Gln Val Val Phe Ser Gly Glu Ser Cys Ser Pro Arg
         50                  55                  60

Ala Ile Pro Thr Pro Ile Tyr Leu
 65                  70

<210> SEQ ID NO 20
<211> LENGTH: 71
<212> TYPE: PRT
<213> ORGANISM: Homo sapiens

<400> SEQUENCE: 20

Arg Thr Pro Ser Asp Lys Pro Val Ala His Val Val Ala Asn Pro Gln
 1               5                  10                  15

Ala Glu Gly Gln Leu Gln Trp Leu Asn Arg Arg Ala Asn Ala Leu Leu
                 20                  25                  30

Ala Asn Gly Val Glu Leu Arg Asp Asn Gln Leu Val Val Pro Ser Glu
             35                  40                  45

Gly Leu Tyr Leu Ile Tyr Ser Gln Val Leu Phe Lys Gly Gln Gly Cys
         50                  55                  60

Pro Ser Thr His Val Leu Leu
 65                  70

<210> SEQ ID NO 21
<211> LENGTH: 70
<212> TYPE: PRT
<213> ORGANISM: Mouse

<400> SEQUENCE: 21

Gln Asn Ser Ser Asp Lys Pro Val Ala His Val Val Ala Asn His Gln
 1               5                  10                  15

Val Glu Glu Gln Leu Glu Trp Leu Ser Gln Arg Ala Asn Ala Leu Leu
                 20                  25                  30

Ala Asn Gly Met Asp Leu Lys Asp Asn Gln Leu Val Val Pro Ala Asp
             35                  40                  45

Gly Leu Tyr Leu Val Tyr Ser Gln Val Leu Phe Lys Gly Gln Gly Cys
```

```
                 50                  55                  60
Pro Asp Tyr Val Leu Leu
 65                  70

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Peptide
      from the HIV TAT protein

<400> SEQUENCE: 22

Tyr Gly Arg Lys Lys Arg Arg Gln Arg Arg Arg
 1               5                  10

<210> SEQ ID NO 23
<211> LENGTH: 1055
<212> TYPE: DNA
<213> ORGANISM: Homo sapiens
<220> FEATURE:
<221> NAME/KEY: CDS
<222> LOCATION: (67)..(966)
<220> FEATURE:
<223> OTHER INFORMATION: Human NTR3

<400> SEQUENCE: 23
gaattcggca cgaggcaggg tcctgtgtcc gcgctgagcc gcgctctccc tgctccagca      60 aggacc atg agg gcg ctg gag ggg cca ggc ctg tcg ctg ctg tgc ctg       108
       Met Arg Ala Leu Glu Gly Pro Gly Leu Ser Leu Leu Cys Leu
        1               5                  10 gtg ttg gcg ctg cct gcc ctg ctg ccg gtg ccg gct gta cgc gga gtg      156
Val Leu Ala Leu Pro Ala Leu Leu Pro Val Pro Ala Val Arg Gly Val
 15                  20                  25                  30 gca gaa aca ccc acc tac ccc tgg cgg gac gca gag aca ggg gag cgg      204
Ala Glu Thr Pro Thr Tyr Pro Trp Arg Asp Ala Glu Thr Gly Glu Arg
                 35                  40                  45 ctg gtg tgc gcc cag tgc ccc cca ggc acc ttt gtg cag cgg ccg tgc      252
Leu Val Cys Ala Gln Cys Pro Pro Gly Thr Phe Val Gln Arg Pro Cys
             50                  55                  60 cgc cga gac agc ccc acg acg tgt ggc ccg tgt cca ccg cgc cac tac      300
Arg Arg Asp Ser Pro Thr Thr Cys Gly Pro Cys Pro Pro Arg His Tyr
         65                  70                  75 acg cag ttc tgg aac tac ctg gag cgc tgc cgc tac tgc aac gtc ctc      348
Thr Gln Phe Trp Asn Tyr Leu Glu Arg Cys Arg Tyr Cys Asn Val Leu
     80                  85                  90 tgc ggg gag cgt gag gag gag gca cgg gct tgc cac gcc acc cac aac      396
Cys Gly Glu Arg Glu Glu Glu Ala Arg Ala Cys His Ala Thr His Asn
 95                  100                 105                 110 cgt gcc tgc cgc tgc cgc acc ggc ttc ttc gcg cac gct ggt ttc tgc      444
Arg Ala Cys Arg Cys Arg Thr Gly Phe Phe Ala His Ala Gly Phe Cys
                 115                 120                 125 ttg gag cac gca tcg tgt cca cct ggt gcc ggc gtg att gcc ccg ggc      492
Leu Glu His Ala Ser Cys Pro Pro Gly Ala Gly Val Ile Ala Pro Gly
             130                 135                 140 acc ccc agc cag aac acg cag tgc cag ccg tgc ccc cca ggc acc ttc      540
Thr Pro Ser Gln Asn Thr Gln Cys Gln Pro Cys Pro Pro Gly Thr Phe
         145                 150                 155 tca gcc agc agc tcc agc tca gag cag tgc cag ccc cac cgc aac tgc      588
Ser Ala Ser Ser Ser Ser Glu Gln Cys Gln Pro His Arg Asn Cys
     160                 165                 170 acg gcc ctg ggc ctg gcc ctc aat gtg cca ggc tct tcc tcc cat gac      636
```

-continued

```
                Thr Ala Leu Gly Leu Ala Leu Asn Val Pro Gly Ser Ser His Asp
                175                 180                 185                 190 acc ctg tgc acc agc tgc act ggc ttc ccc ctc agc acc agg gta cca           684
Thr Leu Cys Thr Ser Cys Thr Gly Phe Pro Leu Ser Thr Arg Val Pro
            195                 200                 205 gga gct gag gag tgt gag cgt gcc gtc atc gac ttt gtg gct ttc cag           732
Gly Ala Glu Glu Cys Glu Arg Ala Val Ile Asp Phe Val Ala Phe Gln
        210                 215                 220 gac atc tcc atc aag agg ctg cag cgg ctg ctg cag gcc ctc gag gcc           780
Asp Ile Ser Ile Lys Arg Leu Gln Arg Leu Leu Gln Ala Leu Glu Ala
            225                 230                 235 ccg gag ggc tgg ggt ccg aca cca agg gcg ggc cgc gcg gcc ttg cag           828
Pro Glu Gly Trp Gly Pro Thr Pro Arg Ala Gly Arg Ala Ala Leu Gln
        240                 245                 250 ctg aag ctg cgt cgg cgg ctc acg gag ctc ctg ggg gcg cag gac ggg           876
Leu Lys Leu Arg Arg Arg Leu Thr Glu Leu Leu Gly Ala Gln Asp Gly
255                 260                 265                 270 gcg ctg ctg gtg cgg ctg ctg cag gcg ctg cgc gtg gcc agg atg ccc           924
Ala Leu Leu Val Arg Leu Leu Gln Ala Leu Arg Val Ala Arg Met Pro
                275                 280                 285 ggg ctg gag cgg agc gtc cgt gag cgc ttc ctc cct gtg cac                   966
Gly Leu Glu Arg Ser Val Arg Glu Arg Phe Leu Pro Val His
            290                 295                 300 tgatcctggc cccctcttat ttattctaca tccttggcac cccacttgca ctgaaagagg        1026
ctttttttta aatagaagaa atgaggttt                                          1055
```

<210> SEQ ID NO 24
<211> LENGTH: 300
<212> TYPE: PRT
<213> ORGANISM: Homo sapiens

<400> SEQUENCE: 24

```
Met Arg Ala Leu Glu Gly Pro Gly Leu Ser Leu Leu Cys Leu Val Leu
 1               5                  10                  15

Ala Leu Pro Ala Leu Pro Val Pro Ala Val Arg Gly Val Ala Glu
            20                  25                  30

Thr Pro Thr Tyr Pro Trp Arg Asp Ala Glu Thr Gly Glu Arg Leu Val
        35                  40                  45

Cys Ala Gln Cys Pro Pro Gly Thr Phe Val Gln Arg Pro Cys Arg Arg
    50                  55                  60

Asp Ser Pro Thr Thr Cys Gly Pro Cys Pro Pro Arg His Tyr Thr Gln
65                  70                  75                  80

Phe Trp Asn Tyr Leu Glu Arg Cys Arg Tyr Cys Asn Val Leu Cys Gly
                85                  90                  95

Glu Arg Glu Glu Glu Ala Arg Ala Cys His Ala Thr His Asn Arg Ala
            100                 105                 110

Cys Arg Cys Arg Thr Gly Phe Phe Ala His Ala Gly Phe Cys Leu Glu
        115                 120                 125

His Ala Ser Cys Pro Pro Gly Ala Gly Val Ile Ala Pro Gly Thr Pro
    130                 135                 140

Ser Gln Asn Thr Gln Cys Gln Pro Cys Pro Pro Gly Thr Phe Ser Ala
145                 150                 155                 160

Ser Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190
```

-continued

```
Cys Thr Ser Cys Thr Gly Phe Pro Leu Ser Thr Arg Val Pro Gly Ala
        195                 200                 205

Glu Glu Cys Glu Arg Ala Val Ile Asp Phe Val Ala Phe Gln Asp Ile
    210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
                260                 265                 270

Leu Val Arg Leu Leu Gln Ala Leu Arg Val Ala Arg Met Pro Gly Leu
        275                 280                 285

Glu Arg Ser Val Arg Glu Arg Phe Leu Pro Val His
    290                 295                 300
```